United States Patent
Ataman-Önal et al.

(10) Patent No.: US 9,062,099 B2
(45) Date of Patent: Jun. 23, 2015

(54) PRODEFENSIN-A6 ASSAY METHOD FOR THE IN VITRO DIAGNOSIS OF COLORECTAL CANCER

(75) Inventors: Yasemin Ataman-Önal, Reyrieux (FR); Corinne Beaulieu, Rillieux la Pape (FR); Sandrine Busseret, Lyons (FR); Jean-Philippe Charrier, Tassin la Demi-lune (FR); Geneviève Choquet-Kastylevsky, Francheville (FR); Dominique Rolland, Saint Genis les Ollieres (FR)

(73) Assignee: BIOMERIEUX, Marcy l'Etoile (FR)

( * ) Notice: Subject to any disclaimer, the term of this patent is extended or adjusted under 35 U.S.C. 154(b) by 279 days.

(21) Appl. No.: 13/260,854

(22) PCT Filed: Apr. 1, 2010

(86) PCT No.: PCT/FR2010/050620
§ 371 (c)(1),
(2), (4) Date: Sep. 28, 2011

(87) PCT Pub. No.: WO2010/112777
PCT Pub. Date: Oct. 7, 2010

(65) Prior Publication Data
US 2012/0129200 A1 May 24, 2012

(30) Foreign Application Priority Data
Apr. 3, 2009 (FR) .................................... 09 52192

(51) Int. Cl.
G01N 33/53 (2006.01)
C07K 16/18 (2006.01)
C07K 16/30 (2006.01)
G01N 33/574 (2006.01)

(52) U.S. Cl.
CPC ................. *C07K 16/18* (2013.01); *C07K 16/30* (2013.01); *G01N 33/57419* (2013.01); *G01N 2333/4721* (2013.01)

(58) Field of Classification Search
None
See application file for complete search history.

(56) References Cited

PUBLICATIONS

Nam JBC vol. 280 p. 8260 (2005).*
Harlow, Antibodies, A Laboratory Manual, 1988, pp. 72-76.*
Jones, D. E., et al. "Paneth cells of the human small intestine express an antimicrobial peptide gene". J. Biol. Chem, (1992) 267, 23216-23225.
Bevins, Charles L., et al. "Human enteric defensin genes: chromosomal map position and a model for possible evolutionary relationships." Genomics 31,1 (1996), 95-106.
Lawrance, Ian C., et al., "Ulcerative colitis and Crohn's disease: distinctive gene expression profiles and novel susceptibility candidate genes" Hum Mol Gen (2001), 445-456.
Nam, Myeong J., et al. "Identification of defensin α6 as a potential biomarker in colon adenocarcinoma." Journal of Biological Chemistry 280, 9 (2005), 8260-8265.
Remold-O'Donnell, et al. "Sequence and molecular characterization of human monocyte/neutrophil elastase inhibitor." Proceedings of the National Academy of Sciences 89,12 (1992), 5635-5639.
Cooley, J., et al. "The serpin MNEI inhibits elastase-like and chymotrypsin-like serine proteases through efficient reactions at two active sites" Biochemistry 40, 51 (2001), 15762-15770.
Algrain, M., et al. "Ezrin contains cytoskeleton and membrane binding domains accounting for its proposed role as a membrane-cytoskeletal linker" The Journal of cell biology 120, 1 (1993), 129-139.
Jiang, W. G., et al. "Cytokine regulation of ezrin expression in the human colon cancer cell line HT29." Anticancer research 16, 2 (1995), 861-865.
Hiscox, S., et al. "Exrin regulates cell-cell and cell-matrix adhesion, a possible role with E-cadherin/beta-catenin." Journal of cell science 112,18 (1999), 3081-3090.
Xiao, T., et al. "An approach to studying lung cancer-related proteins in human blood." Molecular & Cellular Proteomics 4,10 (2005), 1480-1486.
Anders, M.W., et al. "Aminoacylases" Advances in Pharmacology, vol. 27, 1994, pp. 431-448.
Lorentz, K., et al. "A new method for the assay of aminoacylase: Elaboration of a fixed-incubation method for routine measurements." Clinica Chimica Acta 63, 3 (1975), 263-269.
Lorentz, K., et al. "Clinical application of a new method for the determination of aminoacylase in human serum." Clinica Chimica Acta 63, 3 (1975), 271-274.
Cook, R. M., et al. "Human aminoacylase-1. Cloning, sequence, and expression analysis of a chromosome 3p21 gene inactivated in small cell lung cancer." Journal of Biological Chemistry 268, 23 (1993), 17010-17017.
Miller, Y. E., et al. "Lack of expression of aminoacylase-1 in small cell lung cancer. Evidence for inactivation of genes encoded by chromosome 3p." Journal of Clinical Investigation 83,6 (1989), 2120-2124.
Balabanov, S., et al. "Tumour related enzyme alterations in the clear cell type of human renal cell carcinoma identified by two-dimensional gel electrophoresis." European Journal of Biochemistry 268, 22 (2001), 5977-5980.
Chan, L., et al. "Human liver fatty acid binding protein cDNA and amino acid sequence. Functional and evolutionary implications." Journal of Biological Chemistry 260, 5 (1985), 2629-2632.
Das, R., et al. "Expression pattern of fatty acid-binding proteins in human normal and cancer prostate cells and tissues." Clinical cancer research 7, 6 (2001), 1706-1715.
Stulik, J., et al. "Proteome study of colorectal carcinogenesis." Electrophoresis 22,14 (2001), 3019-3025.
Yamazaki, Toshiyuki, et al. "Liver fatty acid binding protein is a new prognostic factor for hepatic resection of colorectal cancer metastases." Journal of surgical oncology 72, 2 (1999), 83-87.
Sweetser, D., et al. "The human and rodent intestinal fatty acid binding protein genes. A comparative analysis of their structure, expression, and linkage relationships." Journal of Biological Chemistry 262, 33 (1987), 16060-16071.

(Continued)

*Primary Examiner* — Sheela J Huff
(74) *Attorney, Agent, or Firm* — Oliff PLC

(57) ABSTRACT

The present invention relates to a method for the in vitro diagnosis of colorectal cancer by determining the presence of the Prodefensin-A6 tumour marker in a biological sample taken from a patient suspected of having colorectal cancer, it being possible for said method to be used both in early diagnosis, screening, therapeutic follow-up and prognosis, and in relapse diagnosis in relation to colorectal cancer.

27 Claims, 7 Drawing Sheets

(56) References Cited

PUBLICATIONS

Figure 3:
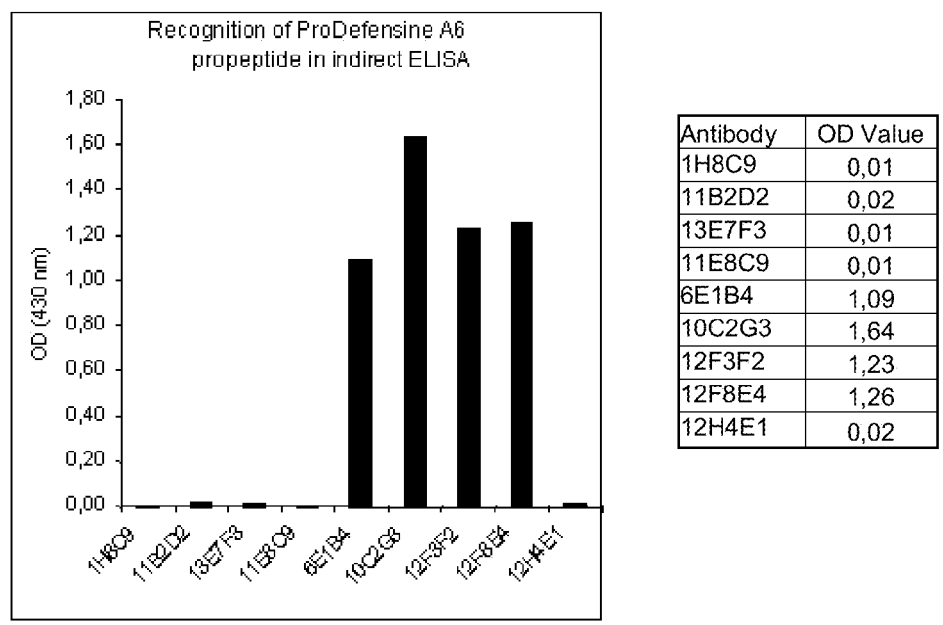

Pelsers, Maurice MAL, et al. "Intestinal-type and liver-type fatty acid-binding protein in the intestine. Tissue distribution and clinical utility." Clinical biochemistry 36, 7 (2003), 529-535.

Xiao, R., et al. "Dietary exposure to soy or whey proteins alters colonic global gene expression profiles during rat colon tumorigenesis." Molecular Cancer 4,1 (2005), 1-17.

Niederkofler, E. E., et al. "Novel mass spectrometric immunoassays for the rapid structural characterization of plasma apolipoproteins." Journal of lipid research 44, 3 (2003), 630-639.

Hortin, G. L. "The MALDI-TOF mass spectrometric view of the plasma proteome and peptidome." Clinical Chemistry 52, 7 (2006), 1223-1237.

Engwegen, J. Y. M. N., et al. "Identification of serum proteins discriminating colorectal cancer patients and healthy controls using surface-enhanced laser desorption ionisation-time of flight mass spectrometry." World Journal of Gastroenterology 12, 10 (2006), 1536-1544.

Zhang, Z., et al. "Three biomarkers identified from serum proteomic analysis for the detection of early stage ovarian cancer." Cancer research 64,16 (2004), 5882-5890.

Hachem, H., et al. "Serum apolipoproteins AI, A-II and B in hepatic metastases comparison with other liver diseases: Hepatomas and cirrhosis." Clinical Chemistry and Laboratory Medicine 24, 3 (1986), 161-166.

Lin, Ching-Shwun, et al. "Human plastin genes. Comparative gene structure, chromosome location, and differential expression in normal and neoplastic cells." Journal of Biological Chemistry 268,4 (1993), 2781-2792.

Delanote, V., et al. "Plastins: versatile modulators of actin organization in (patho) physiological cellular processes" Acta Pharmacologica Sinica 26, 7 (2005), 769-779.

Lavabre Bertrand, Thierry, et al. "Plasma proteasome level is a potential marker in patients with solid tumors and hemopoietic malignancies" Cancer 92, 10 (2001), 2493-2500.

Nakahara, S., et al. "On the role of galectin-3 in cancer apoptosis" Apoptosis 10, 2 (2005), 267-275.

Iurisci, Ida, et al. "Concentrations of galectin-3 in the sera of normal controls and cancer patients." Clinical cancer research 6, 4 (2000), 1389-1393.

Schwartz, Morton K. "Enzymes as prognostic markers and therapeutic indicators in patients with cancer." Clinica chimica acta 206,1 (1992), 77-82.

McCool, Dorothy J., et al. "Roles of calreticulin and calnexin during mucin synthesis in LS180 and HT29/A1 human colonic adenocarcinoma cells." Biochemical Journal 341., Pt 3 (1999), 593-600.

Motoo, Y., et al. "Serum levels of pancreatitis-associated protein in digestive diseases with special reference to gastrointestinal cancers." Digestive diseases and sciences 44, 6 (1999), 1142-1147.

Herlyn, M., et al. "Colorectal carcinoma-specific antigen: detection by means of monoclonal antibodies" Proceedings of the National Academy of Sciences 76, 3 (1979), 1438-1442.

Armstrong, A., et al. "EpCAM: a new therapeutic target for an old cancer antigen" Cancer biology & therapy 2, 4 (2003), 320-325.

Herlyn, D., et al. "IgG2a monoclonal antibodies inhibit human tumor growth through interaction with effector cells" Proceedings of the National Academy of Sciences 79, 15 (1982), 4761-4765.

Abe, Hironori, et al. "Preparation of recombinant MK-1/Ep-CAM and establishment of an ELISA system for determining soluble MK-1/Ep-CAM levels in sera of cancer patients." Journal of immunological methods 270, 2 (2002), 227-233.

Barak, V. et al. "Clinical utility of cytokeratins as tumor markers" Clinical biochemistry 37, 7 (2004), 529-540.

Kim, H., et al. "Rapid fecal cytokeratin-19 test and fecal occult blood test in screening for gastronintestinal diseases" Annals of Clinical & Laboratory Science 36, 3, (2006), 294-298.

Roca, F., et al. "Prognostic value of E cadherin, beta catenin, MMPs (7 and 9), and TIMPs (1 and 2) in patients with colorectal carcinoma" Journal of surgical oncology 93, 2 (2006), 151-160.

Damsky, C. H., et al. "Identification and purification of a cell surface glycoprotein mediating intercellular adhesion in embryonic and adult tissue" Cell 34, 2 (1983), 455-466.

Katayama, M., et al. "Soluble E-cadherin fragments increased in circulation of cancer patients." British journal of cancer 69, 3 (1994), 580-585.

Wilmanns, C., et al. "Soluble serum E-cadherin as a marker of tumour progression in colorectal cancer patients." Clinical & experimental metastasis 21, 1 (2004), 75-78.

Gold, P., et al. "Specific carcinoembryonic antigens of the human digestive system" The Journal of experimental medicine 122, 3 (1965), 467-481.

Duffy, M. J. "Carcinoembryonic antigen as a marker for colorectal cancer: is it clinically useful?." Clinical chemistry 47, 4 (2001), 624-630.

Kim, Yonggoo, et al. "Gastrointestinal tract cancer screening using fecal carcinoembryonic antigen." Annals of Clinical & Laboratory Science 33,1 (2003), 32-38.

Holmgren, J., et al. "Detection by monoclonal antibody of carbohydrate antigen CA 50 in serum of patients with carcinoma." British medical journal (Clinical research ed.) 288, 6429 (1984), 1479-1482.

Klug, T. L., et al. "Monoclonal antibody immunoradiometric assay for an antigenic determinant (CA 72) on a novel pancarcinoma antigen (TAG-72)" International journal of cancer 38, 5 (1986), 661-669.

Kuusela, P., et al. "Comparison of a new tumour marker CA 242 with CA 19-9, CA 50 and carcinoembryonic antigen (CEA) in digestive tract diseases" British journal of cancer 63, 4 (1991), 636-640.

Holland, M., et al. "Testosterona Serica: Posible Marcador En El Cancer Colorrectal" Revista Medicina 53, 2 (1993), 117-123.

Model, F., et al. "Detection of Methylated DNA in Plasma from Colorectal Cancer Patients and Controls by Real-Time Pcr Analysis of Septin-9." Annals of Oncology. vol. 17. Great Clarendon St, Oxford Ox2 6dp, England: Oxford Univ Press, 2006.

Ebert, M., et al. "Aristaless-like Homeobox-4 Gene Methylation Is a Potential Marker for Colorectal Adenocarcinomas" Gastroenterology 131, 5 (2006), 1418-1430.

Bianco, C., et al. "Identification of cripto-1 as a novel serologic marker for breast and colon cancer" Clinical cancer research 12,17 (2006), 5158-5164.

Lee, H., et al. "Macrophage migration inhibitory factor may be used as an early diagnostic marker in colorectal carcinomas" American journal of clinical pathology 129, 5 (2008), 772-779.

Hardt, P. D., et al. "Faecal tumour M2 pyruvate kinase: a new, sensitive screening tool for colorectal cancer" British journal of cancer 91, 5 (2004), 980-984.

Sagiv, E., et al. "Targeting CD24 for treatment of colorectal and pancreatic cancer by monoclonal antibodies or small interfering RNA" Cancer research 68, 8 (2008), 2803-2812.

Leman, E. S., et al. "Initial Analyses of Colon Cancer—Specific Antigen (CCSA-4) as Colorectal Cancer-Associated Serum Markers" Cancer research 67, 12 (2007), 5600-5605.

Jones, D.E., et al. "Defensin-6 mRNA in human Paneth cells: implications for antimicrobia peptides in host defense of the human bowel" FEBS letters 315, 2 (1993), 187-192.

Szyk, A., et al. "Crystal structures of human α-defensins HNP4, HD5, and HD6" Protein science 15,12 (2006), 2749-2760.

Abarzúa, P. et al. "Microinjection of monoclonal antibody PAb421 into human SW480 colorectal carcinoma cells restores the transcription activation function to mutant p53" Cancer research 55,16 (1995), 3490-3494.

Kim, Jin-Ah, et al. "Troglitazone activates p21 Cip/WAF1 through the ERK pathway in HCT15 human colorectal cancer cells" Cancer Letters 179, 2 (2002), 185-195.

Romani, R., et al. "Dose Dependent In Vivo Inhibition of Human Colorectal Cancer (Lovo) by the Gastrin Receptor Antagonist, Ci-988" Clinical and Experimental Pharmacology and Physiology 23, 5 (1996), 438-440.

Goi, Takanori, et al. "Angiogenesis and tumor proliferation/metastasis of human colorectal cancer cell line SW620 transfected with endocrine glands-derived-vascular endothelial growth factor, as a new angiogenic factor" Cancer research 64, 6 (2004), 1906-1910.

(56) References Cited

OTHER PUBLICATIONS

Schmid, K. et al. "Amino acid sequence of human plasma galactoglycoprotein: identity with the extracellular region of CD43 (sialophorin)" Proceedings of the National Academy of Sciences 89, 2 (1992), 663-667.

English Translation of International Search Report for PCT/FR2010/050620 dtd Jul. 10, 2010.

English Translation of Written Opinion for PCT/FR2010/050620 dtd Aug. 11, 2011.

* cited by examiner

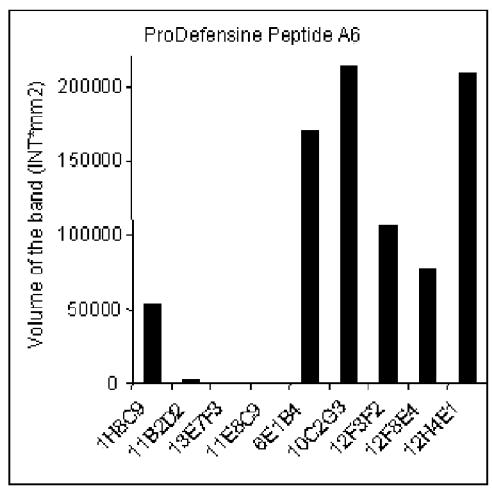
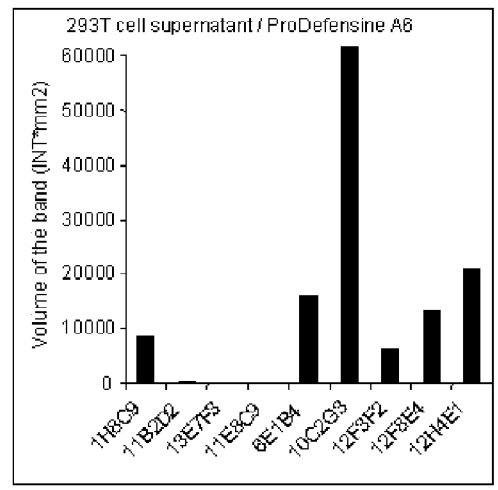
Figure 1A                    Figure 1B
|        | 293T celle supernatant /ProDefensine A6 | ProDefensine A6 Peptide |
|--------|------|--------|
| 1H8C9  | 8604  | 53505  |
| 11B2D2 | 630   | 3255   |
| 13E7F3 | 140   | 805    |
| 11E8C9 | 0     | 489    |
| 6E1B4  | 16158 | 169906 |
| 10C2G3 | 61547 | 214543 |
| 12F3F2 | 6392  | 105809 |
| 12F8E4 | 13402 | 78225  |
| 12H4E1 | 20942 | 208927 |
Figure 1C

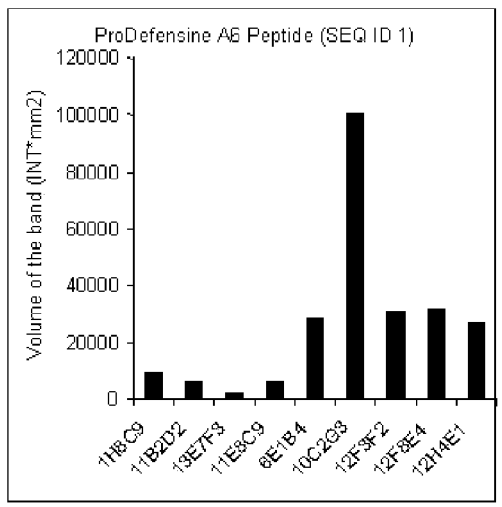
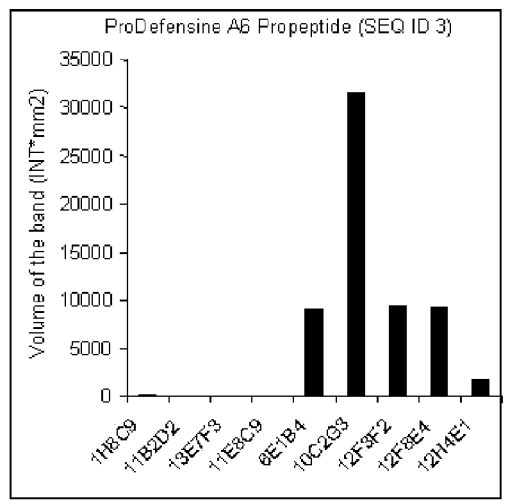
Figure 2A                                    Figure 2B
|        | ProDefensine A6 Peptide (SEQ ID 1) | ProDefensine A6 Propeptide (SEQ ID 3) | Ratio*100 |
|--------|-----------------------------------|---------------------------------------|-----------|
| 1H8C9  | 9554                              | 100                                   | 1         |
| 11B2D2 | 6015                              |                                       |           |
| 13E7F3 | 2078                              |                                       |           |
| 11E8C9 | 6326                              |                                       |           |
| 6E1B4  | 28726                             | 9027                                  | 31        |
| 10C2G3 | 100928                            | 31641                                 | 31        |
| 12F3F2 | 31025                             | 9361                                  | 30        |
| 12F8E4 | 31791                             | 9308                                  | 29        |
| 12H4E1 | 27015                             | 1729                                  | 6         |
Figure 2C

| Antibody and epitope | | Mimotope sequences[a] | | | | | | | | | | | SEQ ID |
|---|---|---|---|---|---|---|---|---|---|---|---|---|---|
| 1H8C9 Epitope 2 | Consensus | | | V/L | T/L | $X_3$ | P/S | T/W | $X_6$ | $X_7$ | $X_8$ | R | | SEQ ID 7 |
| | Immunoreactive Units | | | N | Y | V | T | P | P | W | A | I | F | R | H | | | SEQ ID 8 |
| | | W | T | G | V | L | S | P | T | Q | E | Y | R | | | SEQ ID 9 |
| | | | | S | H | L | T | P | P | W | M | D | Y | R | V | | | SEQ ID 10 |
| | | V | M | A | V | T | C | S | T | C | D | S | R | | | SEQ ID 11 |
| | | | | L | T | P | P | T | E | D | L | R | P | | P | D | SEQ ID 12 |
| 11B2D2 Epitope 3 | Consensus | | | | | S/T | C/- | $X_3$ | H/R | $X_5$ | G/V | H | C/N | | SEQ ID 13 |
| | Immunoreactive Units | | | Y | G | N | H | S | C | T | H | I | G | H | C | | | SEQ ID 14 |
| | | | | G | P | S | Y | T | C | L | H | F | G | H | C | | | SEQ ID 15 |
| | | | | | | T | - | E | R | E | V | H | N | W | | F | P F H | SEQ ID 16 |
| 11E8C9 Epitope 4 | Consensus | | | | | P/W | H | P | E | $X_3$ | $X_4$ | $X_5$ | W/V | V/A | V/I | | SEQ ID 17 |
| | Immunoreactive Units | | | | | Y | P | H | P | W | S | M | H | V | I | R A | SEQ ID 18 |
| | | | T | T | T | P | H | P | W | A | L | F | A | V | | | SEQ ID 19 |
| | | | | | T | P | H | P | W | Q | R | W | V | V | Y S | SEQ ID 20 |
| | | E | D | V | L | R | W | H | P | E | W | P | G | | | | SEQ ID 21 |
| 13E7F3 Epitope 5 | Consensus | | | Y/N | H | $X_2$ | $X_3$ | $X_4$ | P/G | | | | | SEQ ID 22 |
| | Immunoreactive Units | | | Y | H | E | T | W | P | P | K | S | A | Q | L | | SEQ ID 23 |
| | | | | Y | H | D | N | W | P | Q | P | S | R | S | W | | SEQ ID 24 |
| | | Q | H | N | H | Q | R | H | G | A | M | G | A | | | SEQ ID 25 |
| | | | | Y | H | D | M | W | P | M | S | G | R | M | A | | SEQ ID 26 |
| | | | | Y | H | D | N | W | P | P | L | N | G | A | R | | SEQ ID 27 |
| | | | | Y | H | D | M | W | P | A | I | Q | L | S | P | | SEQ ID 28 |
| | | | | Y | H | E | K | F | P | G | P | V | V | L | P | | SEQ ID 29 |

Figure 4

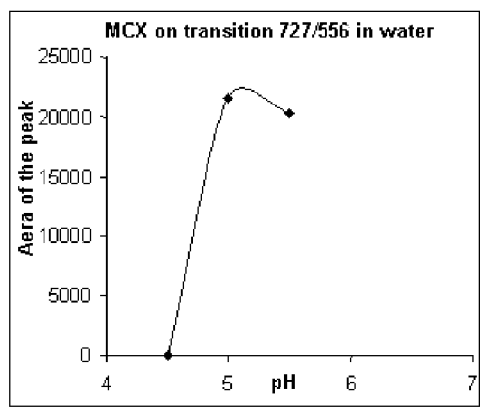
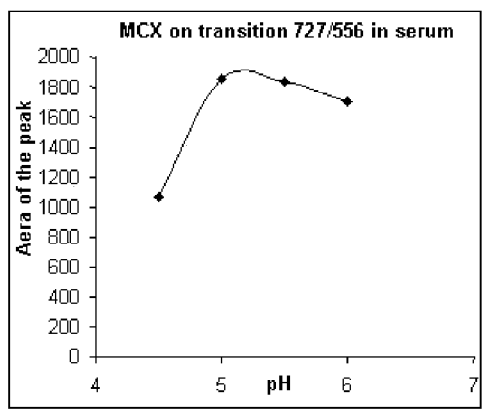
Figure 7A              Figure 7B
Figure 7

PRODEFENSIN-A6 ASSAY METHOD FOR THE IN VITRO DIAGNOSIS OF COLORECTAL CANCER

CROSS REFERENCE TO RELATED APPLICATIONS

This application is the national stage application under 35 USC 371 of International Application No. PCT/FR2010/050620, filed Apr. 1, 2010, which claims the benefit of French Patent Application No. 0952192, filed Apr. 3, 2009, the disclosures of which are hereby incorporated by reference.

The present invention relates to the cancerology field. More particularly, the subject of the present invention is a method for the in vitro diagnosis of colorectal cancer in a human patient, by determining the presence of Prodefensin-A6 in a biological sample taken from this patient, it being possible for said method to be used both in early diagnosis, screening, therapeutic follow-up and prognosis, and in relapse diagnosis in relation to colorectal cancer.

Colorectal cancer (CRC) is a major public health problem. The worldwide incidence thereof was estimated at 875 000 new cases in 1996[1]. Taking into account both sexes, it is the cancer that occurs most frequently in western countries, where it is generally classed among the first 3 most common causes of death due to cancer. The 5-year survival rate, all stages taken into account, is in the region of 60%.

Only early diagnosis offers the hope of a curative treatment. However, at the current time, there is no serological screening test nor specific diagnostic test which is early.

Screening for colorectal cancer is currently carried out in Europe with two distinct approaches: firstly, using a paraclinical test which consists in looking for the presence of blood in the stools (Faecal Occult Blood Test, FOBT, marketed, for example, under the name Hemoccult®). This technique has demonstrated its clinical usefulness. When it is used every 2 years in individuals between the ages of 50 and 74, it can reduce by 15 to 20% mortality due to colorectal cancer[2]. For this, it is necessary for more than half the population concerned to participate regularly in the screening and for a colonoscopy to be carried out in the event of a positive test, optionally followed by an appropriate treatment.

Nevertheless, this screening technique suffers from a certain number of handicaps:

The major drawback of this test is its mediocre sensitivity, most especially for adenomas (precancerous dysplastic lesion) which, if they are large in size or represent severe dysplasia, will result in the development of cancer in 1 case out of 10.
  The test is also not very specific. The appearance of blood in the stools may be related to a nontumour condition: ulcerative colitis, haemorrhoids, fistulae, etc. In this case, an investigation by colonoscopy must be carried out, with the drawbacks described hereinafter.
  Finally, Hemoccult® tests are difficult to interpret; they must therefore be read in specialized centres, by qualified competent personnel.
  Immunological tests specific for human haemoglobin (Feca EIA®, Heme Select®, etc.) have also been described. They probably constitute progress compared with Hemoccult®, but they essentially exhibit the same problems. Thus, InSure™, marketed by Enterix Inc., makes it possible to detect 87% of patients suffering from CRC and 47% of those having precancerous polyps. It is a test for detecting human haemoglobin in the stools, and more particularly the globin portion of this molecule.

A second screening strategy is the systemic performing of a colonoscopy after the age of 50, which makes it possible in theory to reduce mortality due to colorectal cancer. However, the acceptability of this examination in individuals who are in good health is too low for a screening policy using endoscopy to reduce mortality (the level of compliancy for colonoscopy in European countries having set up this screening strategy is around 2%). There is a not insignificant risk (0.1%) of perforation and bleeding of the colon and of death (1/10 000), and it is also very expensive for public health. Furthermore, colonoscopy requires a very restrictive prior colonic preparation, which in large part explains the poor compliance.

Tumour markers that can be assayed by immunoassays have for a long time been described in the context of colorectal cancer. They are in particular the carcinoembryonic antigen (CEA) and CA19-9.

CEA is used for follow-up. It cannot be used for the screening or for the early diagnosis of colorectal cancer because its sensitivity and its specificity are insufficient. This is because this marker is expressed by other types of cancer, and in benign pathologies. Despite everything, it is possible to increase sensitivity without losing specificity by combining, with CEA, another tumour marker such as CA19-9 or CA72-4.

The causes of physiological variations in CA19-9 are rare, but other benign conditions (hepatobiliary conditions, pancreatic conditions), or malignant conditions may induce an increase in CA19-9. This marker, taken alone, is therefore also of no interest for diagnosis. Nevertheless, since its serum concentration is correlated with the size of the tumour and the presence of metastases, it may also enable a therapeutic follow-up or the early demonstration of relapses.

Commercially available tests have, moreover, been proposed, such as:

Colopath®/ColorectAlert$^{MD}$, marketed by Ambrilia, is a rapid and relatively noninvasive screening test for CRC. Colopath® detects a plasmalogen (class of complex lipids which are part of phospholipids) in the rectal mucus of individuals with a colorectal pathological condition, whereas ColorectAlert$^{MD}$ detects T-antigen, a complex sugar in the rectal mucus. The Colopath®/ColorectAlert$^{MD}$ test involves the application of rectal mucus to a test strip, and the positive or negative result is based on a Schiff reaction. Ambrilia has studied 1787 individuals and demonstrated that Colopath®/ColorectAlert$^{MD}$ detects 54% of cases of early-stage colorectal cancer and 49% of all stages combined.
  COLARIS, marketed by Myriad Genetics, is a test for detecting, in the blood, mutations in the MLH1 and MSH2 genes for screening for hereditary nonpolyposis colon cancer (HNPCC syndrome). The result of the test is available in 3 weeks. Myriad uses the most sensitive and most specific sequencing techniques currently available. The test is expensive.
  DR-70®, marketed by AMDL, is a test to screen for various types of cancer (lung, colon, breast, liver, stomach, etc.). It is not therefore specific for CRC. The principle of said test is based on the double sandwich ELISA technique (assaying of the DR-70 antigen). Revealing is carried out by enzymatic reaction (antibodies coupled to biotin and to streptavidin). A coloured reaction indicates the presence of cancer.

The applicant has now surprisingly demonstrated a novel marker for adenocarcinoma, which is released out of the cancerous tissues by the malignant colonic tumours and is characteristic of these tumours, such that it can be detected both in biological samples remote from the malignant tumours, and in the tumours themselves.

Thus, a first subject of the present invention is a method for the in vitro diagnosis of colorectal cancer by determining the presence of Prodefensin-A6 in biological samples taken from patients suspected of having colorectal cancer, and preferably remote from the tumours.

The present invention also relates to the use of this method both in early diagnosis, screening, therapeutic follow-up and prognosis, and in relapse diagnosis in relation to colorectal cancer.

The method of the invention therefore makes it possible to diagnose colorectal cancer specifically and early by means of a simple test consisting in searching for the presence of Prodefensin-A6 in a biological sample taken from a patient, said sample being preferably remote from the potential tumour. Indeed, the applicant has shown, unexpectedly, that colonic tumours not only specifically secrete Prodefensin-A6, but especially release it out of the cancerous tissue, as will be demonstrated in greater detail hereinafter, and that its concentration in the biological sample in which the method of the invention is carried out is increased in comparison with the reference values determined for healthy patients.

The determination of the presence of Prodefensin-A6 in a biological sample which may or may not be remote from the tumour thus makes it possible to conclude with respect to the pathological condition sought. One of the advantages of the method of the invention therefore lies in the possibility of using a sample remote from the potential tumour as a diagnostic sample, thereby enabling a simple and noninvasive diagnosis, whereas a tissue diagnosis requires a biopsy taken invasively. Indeed, the study of tissue markers, for example on a tissue section (immunohistochemistry), may be of prognostic interest, but is of no interest for screening or diagnosing colorectal cancer.

Defensins are a family of antimicrobial peptides involved in the host's defence against microbial attacks. They consist of 30 to 40 amino acids and have the property of selectively disaggregating membranes. Like other eukaryotic proteins, Defensins can be present in the form of a mature protein or in the form of a precursor.

A precursor, also called precursor protein, consists of a propeptide and a mature part. Thus, Prodefensin-A6 is the precursor protein of the mature Defensin-A6 protein, consists of 100 amino acids and comprises a signal peptide (amino acids 1-19), the propeptide (amino acids 20-65) and the mature Defensin-A6 protein (amino acids 66-100).

In general, precursor proteins have for a long time been considered to be only metabolic molecules. However, a certain number of recent examples, in particular in the neuropeptide field, indicate that, in certain situations, precursor proteins have a biological activity that is specific and dissociative from that of the mature peptide that they can generate. Admittedly, the sequence of precursor proteins includes that of the mature proteins, for example the sequence of the Prodefensins includes that of the Defensins, but their isoelectric points and molecular weights are different. Defensins and Prodefensins are therefore to be considered as two different proteins.

Defensins alpha 5[3] and alpha 6[4] are essentially produced by Paneth cells of the small intestine. The mRNAs of Defensins alpha 5 and 6 are overexpressed in colonic tissue in the case of Crohn's disease[5]. Defensin alpha 6 was identified as a potential marker for colon cancer by Nam et al.[6]. Nam et al. developed a competitive ELISA assay which specifically assays Defensin alpha 6. They defined a threshold (30 ng/ml) beyond which patients were diagnosed as having colorectal cancer. During an analysis of 18 sera from healthy donors and 49 cancer sera, they obtained a diagnostic sensitivity of 69.4% for a diagnostic specificity of 83.3%. No mention was made in said document regarding the Defensin alpha 6 precursor, Prodefensin alpha 6.

Thus, the Defensin alpha 6 precursor, Prodefensin-A6 (Swiss Prot No. Q01524), has never been described as possibly being of use as a marker in relation to cancer and in particular to colorectal cancer and as possibly being assayed in a biological sample which may or may not be remote from the malignant tumour.

The expression "determining the presence of the precursor protein" is intended to mean determination of the precursor beyond the reference values determined for healthy patients. The precursor sought may be the intact precursor of 100 amino acids, the precursor protein without the signal peptide (amino acids 20 to 100) or the propeptide alone (amino acids 20 to 65). It may also be fragments of the latter, such as fragments of the propeptide, with the exclusion of the mature protein (amino acids 66-100) and fragments thereof.

According to one particular embodiment of the invention, the presence of the precursor of Prodefensin-A6, without the signal peptide, is determined. The sequence described for this precursor in the Swiss-Prot database is SEQ ID No.1 (EPLQAEDDPLQAKAYEADAQEQRGAN-DQDFAVSFAEDASSSLRALGSTR AFTCHCRRSCYS-TEYSYGTCTVMGINHRFCCL; corresponding to amino acids 20-100). Preferably, the presence of the propeptide itself having at least the sequence SEQ ID No.2 (EPLQAED-DPLQAKAYEADAQEQRG ANDQDFAVSFAEDASSSL-RALG) and at most the sequence SEQ ID No.1 is determined As is well known to those skilled in the art, protein polymorphisms exist, and the sequences given above are merely indicative. They are the consensus sequences indicated in the Swiss-Prot database, but amino acid substitutions may exist in a to percentage that will be evaluated by those skilled in the art in order to consider whether it is the same protein. Likewise, the site for cleavage of the propeptide at amino acid 65 is theoretical and is given only by way of indication.

The expression "release by colonic tumours" is intended to mean the active or passive secretion or the release, whatever the mechanism, of the tumour marker by the tumour cells themselves or by the neighbouring nontumour cells following lesions or modifications of cell phenotype resulting from the tumour development.

The expression "biological sample in which the method of the invention is carried out" is intended to mean any biological sample which is capable of containing the tumour marker of interest. By way of example of a biological sample not remote from the tumour, mention may be made of solid samples such as the tissue originated from the tumour, from biopsies of this tumour, from lymph nodes, from the patient's metastases, and the cells purified from these solid samples. By way of example of the biological sample remote from the tumour, mention may be made of biological fluids such as whole blood or derivatives thereof, for example serum or plasma, urine, saliva and effusions, bone marrow and stools, and the cells purified from these liquid samples. Blood or derivatives thereof and also stools, effusions and cells purified from these liquid samples are preferred.

The method of the invention may be improved by detecting, in addition to the Prodefensin-A6, at least one other tumour marker, where appropriate also released out of the cancerous tissues by the colonic tumours. Thus, the combination of at least two markers makes it possible to improve the specificity and the sensitivity of the diagnostic test for colorectal cancer.

Thus, another subject of the invention also consists in determining the presence of at least one other tumour marker chosen from the group of following markers: leukocyte elastase inhibitor, ezrin, aminoacylase 1, liver fatty acid-binding protein, intestinal fatty acid-binding protein, apolipoprotein AI, apolipoprotein AII, I-plastin, beta2-microglobulin, proteasome 20S, galectin-3, L-lactate dehydrogenase chain B, calreticulin, regenerating islet-derived protein 3 alpha, tumour-associated calcium signal transducer 1, keratin type II cytoskeletal 8, keratin type I cytoskeletal 18, keratin type I cytoskeletal 19, epithelial cadherin, CEA, villin, CA19-9, CA 242, CA 50, CA 72-2, testosterone, TIMP-1, cripto-1, protein disulphide isomerase, intelectin-1, cytokeratin 20, translationally-controlled tumour protein, (Pro)defensin-A5, MIF, pyruvate kinase M2-PK, calgranulin C, CD24, CCSA-3 (colon cancer specific antigen) and CCSA-4, the detection of DNA fragments in the blood having specific alterations to their methylation profile, for instance methylated DNA of the AXL4 gene (aristaless-like homeobox-4 gene methylation) or the methylated DNA of the septin-9 gene, the detection of specific alterations in faecal DNA fragments, such as specific mutations of faecal DNA or specific alterations of the methylation profile of faecal DNA, the detection of human faecal haemoglobin.

The expression "tumour marker other than Prodefensin-A6" is intended to mean the protein, the messenger RNA or specific modifications of the corresponding gene, such as mutations or methylations. In other words, only Prodefensin-A6 is solely sought in the form of a protein, which may be complete or in the form of a fragment.

The leukocyte elastase inhibitor tumour marker (Swiss Prot No. P30740, also known as LEI, serpin B1, monocyte/neutrophil elastase inhibitor, M/NEI or EI) was sequenced in 1992[7]. LEI specifically inhibits proteases having elastase-type or chymotrypsin-type properties by formation of the complex that cannot be dissociated under the action of SDS[8]. LEI thus inhibits three of the major proteases produced by neutrophils: leukocyte elastase, proteinase-3 and cathepsin G. These proteases enable the immune system to defend the organism by proteolysis of extracellular or phagocytosed substrates. However, when these proteases are in excess, they are responsible for inflammatory reactions. LEI could therefore have a role in regulating and limiting the inflammatory action induced by cell proteases. The applicant has shown, for its part, surprisingly, in patent application WO2009/024691, that the concentration of this protein is increased relative to the reference values determined for healthy patients, such that this protein is a good marker in biological samples taken from a patient having colorectal cancer, said samples being possibly remote from the tumour.

The ezrin marker (Swiss Prot No. P15311, also known as p81, cytovillin or villin-2) is a protein which provides binding between the cell membrane and the actin filaments of the cytoskeleton of the cell, in particular in the microvilli of intestinal epithelial cells[9]. W. G. Jiang and S. Hiscox[10] have shown that the interleukins IL-2, IL-8, IL-10, etc., can inhibit the expression of ezrin in the HT29 human colorectal cancer cell line. The same authors[11] have shown that the inhibition of ezrin expression in the HT115 and HRT18 colorectal cancer cell lines reduces the adhesion between cells and increases the mobility and the invasive behaviour of the cells. They have concluded that ezrin regulates cell/cell and cell/matrix adhesions by interacting with the cell adhesion molecules E-cadherin and beta-catenin They have suggested that ezrin could play an important role in controlling the invasive potential of cancer cells. Moreover, T. Xiao et al.[12] have used an ELISA assay to quantify the plasma ezrin of patients with lung cancer. However, they have not observed any differences compared with control individuals. The applicant has shown, for its part, surprisingly, in patent application WO2009/019365, that the concentration of this protein is increased relative to the reference values determined for healthy patients, such that this protein is a good marker in biological samples taken from a patient having colorectal cancer, said samples possibly being remote from the tumour.

The aminoacylase 1 marker (Swiss Prot No. Q03154, also known as EC 3.5.1.14, N-acyl-L-amino acid amidohydrolase or ACY-1) is part of the aminoacylase family. They are enzymes which catalyse the hydrolysis of acylated amino acids so as to give fatty acids and amino acids[13]. An immunochemical assay for aminoacylase enzymatic activity was developed as early as 1975 by K. Lorentz et al.[14] and was used to assay various tissues and sera[15]. The study showed an increase in aminoacylase activity in the case of hepatic pathological conditions but not in the case of colon cancer. Moreover, the aminoacylase 1 gene has been identified on chromosome 3p21.1[16]. The 3p21.1 region is reduced to homozygocity in small cell lung cancer, and in this case, the aminoacylase expression is repressed or undetectable[17]. Similarly, S. Balabanov et al.[18] have shown that the aminoacylase expression is repressed in the case of kidney cancer. The applicant has shown, for its part, surprisingly, in patent application WO2009/019366, that the concentration of this protein is increased relative to the reference values determined for healthy patients, such that this protein is a good marker in biological samples taken from a patient having colorectal cancer, said samples possibly being remote from the tumour.

The liver fatty acid-binding protein marker (Swiss Prot No. P07148, also known as L-FABP, FABP1, FABPL, Z-protein or sterol transporter protein) belongs to the FABP family which comprises nine isoforms. Each isoform is named according to the tissue in which it was first detected. These isoforms have a shared function and similar three-dimensional structures, but their sequence homology is not high. L-FABP was sequenced in 1985[19]. It is a small protein of 15 kDa that is abundant in the cytosol and has the ability to bind to free fatty acids and also to bilirubin. Some recent studies appear to indicate that impairments in expression of the L-FABP protein could induce a tumorigenesis process. For prostate cancer, the level of expression of L-FABP mRNAs in tumour tissue biopsies was ten times higher than in the normal tissue[20]. For colon cancer, several teams have identified a decrease in the expression of L-FABP protein in the tumour tissue compared with normal colonic mucosa, using two-dimensional electrophoresis techniques[21]. This result has also been confirmed by immunohistochemistry techniques. In addition, the L-FABP protein is a prognostic liver resection marker in patients with colorectal cancer having metastasized to the liver[22]. In patent application WO00/33083, it has been suggested that this marker could be detected in biological fluids from patients having colon cancer. The applicant has, for its part, confirmed, in patent application WO2009/019368, that the concentration of this protein is decreased relative to the reference values determined for healthy patients, such that this protein is a good marker in biological samples taken from a patient having colorectal cancer, said samples being remote from the tumour.

The intestinal fatty acid-binding protein marker (Swiss Prot No. P12104, also known as I-FABP, FABP-2 or FABPI) was sequenced in 1987[23]. It is a small protein of 15 kDa that is abundant in the cytosol and that has the ability to bind free fatty acids and also to bilirubin. The I-FABP protein is expressed in the enterocytes of the small intestine and can constitute approximately 2% of the protein content of this cell type. At the tissue level, the duodenum and the jejunum contain significantly higher amounts of I-FABP than the colon (jejunum: 4.8 µg/g, colon: 0.25 µg/g)[24]. I-FABP could not be detected in the plasma samples of healthy individuals. On the other hand, in certain pathological contexts such as intestinal ischaemia, Crohn's disease or primary biliary cirrhosis, it is possible to demonstrate an increase in the plasma I-FABP concentration in certain individuals[24]. For prostate cancer, it has been shown that the level of expression of I-FABP mRNA in biopsies of tumour tissue is seven times higher than in normal tissue[20]. In the model of induction of a colorectal tumour with azoxymethane in rats, the level of expression of I-FABP mRNA is reduced by 2.92 to 3.97 times when the animals have a diet that reduces the incidence of cancer (soya proteins or whey hydrolysate)[25]. The applicant has confirmed, for example in patent application WO2009/019366, that the concentration of this protein is increased relative to the reference values determined for healthy patients, such that this protein is a good marker in biological samples taken from a patient having colorectal cancer, said samples being remote from the tumour.

Apolipoproteins are a family of proteins consisting of polar amino acids enabling the transport of lipids in the blood through the formation of a hydrophilic macromolecular complex called a lipoprotein. For each of the human plasma apolipoproteins there are isoforms derived from genetic polymorphism and/or from post-translational modifications, the presence of which in the blood can be associated with certain pathological conditions[26]. The plasma concentration of apolipoproteins is not insignificant, of the order of 1 mg/ml[27].

The apolipoprotein AI marker (NCBI No. 490098, also known as Apo A-I, Apo AI and Apo A1) is a protein of 243 amino acids and of 28 kDa. It is essentially synthesized by the liver and the intestine. This protein has been shown to be underabundant in the sera of patients suffering from colorectal cancer compared with healthy individuals, by SELDI-TOF[28]. However, it is specified in this article that patients with CRC are distinguished from healthy individuals by combining Apo AI with other protein markers. Moreover, this article specifies that the assaying of Apo AI by turbidimetric immunoassay, carried by another team, does not confirm the underabundance of this protein in the sera of patients having CRC[29]. Hachem et al.[30] have, for their part, assayed Apo AI in sera of patients having had liver cancer following colorectal cancer metastases. The applicant has shown, for its part, surprisingly, that assaying by immunoassay makes it possible to demonstrate a decrease in the concentration of this protein in patients having colorectal cancer, contrary to what was put forward by Engwegen et al.[28], who were able to demonstrate this decrease only by implementing the SELDI-TOF technique. The assaying of Apo AI by immunoassay in biological samples is a good method for the diagnosis of colorectal cancer, said samples being remote from the tumour, insofar as the assaying by immunoassay that is carried out is not turbidimetry as used by the team of Zhang et al.[29].

The apolipoprotein AII marker (Swiss Prot No. P02652, also known as ApoA II, Apo-AII and Apo A2) is a protein of 17 380 Da composed of two polypeptide chains of 77 amino acids each, linked by a disulphide bridge. Like apolipoprotein AI, apolipoprotein AII is essentially synthesized by the liver and the intestine. Hachem et al.[30] have also assayed, in addition to Apo AI, the Apo AII in sera of patients having had liver cancer following colorectal cancer metastases. However, the results are not significant and do not enable a conclusion to be drawn as to the pathological condition sought. The applicant has shown, for its part, surprisingly, in patent application WO2009/019370, that the concentration of this protein is decreased relative to the reference values determined for healthy patients, such that the decrease in the concentration of this protein in patients having colorectal cancer makes it a good marker in biological samples taken from a patient having colorectal cancer, said samples being remote from the tumour.

The I-plastin marker (Swiss Prot No. Q14651, also known as intestine-specific plastin or plastin 1) belongs to the family of human plastins of which three representatives are known: I-plastin, L-plastin and T-plastin. Some authors call plastins "fimbrins", yet other authors reserve the name fimbrin for I-plastin. The plastins are proteins that bind to actin so as to form the cytoskeleton (cell skeleton). They are 70 kDa proteins that are relatively well-conserved throughout eukaryotic evolution. They exhibit strong tissue specificity, only one isoform at a time is present in normal tissues[31]. The use of plastins with respect to cancer has already been described in patent U.S. Pat. No. 5,360,715, which proposes a method for determining whether a cell is haematopoietic or neoplastic, i.e. cancerous. This method claims the assaying of L-plastin and of T-plastin at the cellular level, and more particularly the assaying of the mRNA thereof. However, despite these properties, no prior study has been carried out to evaluate the importance of plastins in relation to the diagnosis of colorectal cancer using a serum or faecal sample. Furthermore, I-plastin has never been envisaged as a potential cancer marker[32]. The applicant has shown, for its part, surprisingly, in patent application WO2009/019369, that the concentration of this protein is increased relative to the reference values determined for healthy patients, such that this protein is a good marker in biological samples taken from a patient having colorectal cancer, said samples possibly being remote from the tumour.

The beta2-microglobulin marker (Swiss Prot No. P61769, also known as β2-microglobulin, β2M) is a low-molecular-weight protein (11 to 12 kDa) found at the surface of most nucleated human cells. The serum β2-microglobulin level increases in certain patients suffering from cancer, without this increase being specific, or correlated with the nature of the tumour, its stage or the severity of the disease. A significant increase is also observed in other diseases, such as lupus erythematosus, rheumatoid arthritis, Sjögren's syndrome, malignant diseases of the lymphoid system (multiple myeloma, B-cell lymphoma), certain viral diseases (hepatitis or AIDS) and in haemophiliac patients. Since β2-microglobulin is filtered by the renal glomeruli and reabsorbed by the proximal convoluted tubules, its concentration in the blood may be modified in the case of renal pathological conditions. The assaying of β2-microglobulin is thus most commonly reserved for the diagnosis of renal pathological conditions, or for the follow-up of infection with the acquired immunodeficiency virus. However, this marker is known as a tumour marker, in particular for colon cancer.

The proteasome 20S marker (also known as prosome) is the central structure of the proteasome, which is itself a molecular complex responsible for the intracellular degradation of ubiquinated proteins[33]. The proteasome is a molecular complex of 700 kDa, consisting of 28 subunits associated in four rings of seven subunits. In humans, seven alpha units ($\alpha 1, \alpha 2, \alpha 3, \alpha 4, \alpha 5, \alpha 6$ and $\alpha 7$) and ten beta units ($\beta 1, \beta 2, \beta 3, \beta 4, \beta 5, \beta 6, \beta 7, \beta 1i, \beta 2i$ and $\beta 5i$) are known. By virtue of its catalytic properties, the proteasome plays a central role in the mechanisms of cell proliferation, growth, regulation and apoptosis, and therefore in the cancerization pathways. Proteasome inhibition with Bortezomib (Velcade) is a recognized treatment for multiple myeloma. Phase II or III therapeutic trials are ongoing for haematological cancers or tumours. Lavabre-Bertrand et al.[34] have shown that the serum level of proteasome can be to elevated on the occasion of certain pathological conditions, in particular in the case of cancers (myeloma, lymphoma and solid tumours).

The galectin-3 marker (Swiss Prot No. P17931, also known as Gal-3, galactose-specific lectin 3, MAC-2 antigen, IgE-binding protein, 35 kDa lectin, carbohydrate binding protein 35, CBP 35, laminin-binding protein, lectin L-29, L-31, galactoside-binding protein or GALBP) is a lectin capable of binding to beta-galactosidase structures of N-acetyllactosamine type. It is a protein with multiple functions involved in various biological functions, including the adhesion of tumour cells, proliferation, differentiation, angiogenesis, apoptosis and metastatic cancer progression[35]. Various studies have shown that Gal-3 can form complexes with numerous molecules: CEA, IgE, laminin, mucin, Mac-2BP, LAMP1, LAMP2, fibronectin, etc. A serum assay of Gal-3 has been described by Iurisci et al.[36]. Gal-3 was captured on microplates coated with Mac-2-binding protein (a Gal-3-binding protein) and then revealed with an anti-Gal-3 rat antibody. This study showed elevated serum Gal-3 levels in the case of gastrointestinal cancer, breast cancer, lung cancer, ovarian cancer, melanomas and non-Hodgkin's lymphomas.

The L-lactate dehydrogenase chain B marker (Swiss Prot No. P07195, also known as LDH-B, LDH heart unit or LDH-H) is a protein that can form complexes in order to form a homotetramer. This protein can also form complexes with the L-lactate dehydrogenase chain A protein (Swiss Prot No. P00338, also known as LDH-A, LDH muscle unit or LDH-M) in the form of heterotetramers. The serum level and/or the serum enzymatic activity of the tetrameric complexes, called LDH, increase(s) in the blood stream proportionally to the tumour mass for many solid tumours. Its use is recommended in combination with human chorionic gonadotrophin (beta-hCG) and placental alkaline phosphatase for the follow-up of seminal vesicle cancers. LDH is considered to be a marker of interest for the prognosis of lymphomas, of leukaemia and of colon cancer[37].

The calreticulin marker (Swiss Prot No. P27797, also known as CRP55, calregulin, HACBP, ERp60 or grp60) is a multifunctional protein. It is a lectin capable of interacting transiently with virtually all the monoglycosylated proteins of the endoplasmic reticulum. McCool et al.[38] have thus shown that calreticulin is involved in maturation of the colonic mucin MUC2. A method for the diagnosis of CRC which uses assaying of calreticulin in a tissue, the stools or a body fluid is described in patent application WO03/065003.

The regenerating islet-derived protein 3 alpha marker (Swiss Prot No. Q06141, also known as Reg III-alpha, pancreatitis-associated protein 1 or pancreatis associated protein I (PAP 1)) is a protein that is weakly expressed in the healthy pancreas. It is overexpressed during the acute phases of pancreatitis and in certain patients suffering from chronic pancreatitis. In this case, it appears in the pancreatic fluid and in the bloodstream[39]. Motoo et al.[40] have shown, by ELISA assay, that the level of PAP 1 in the blood increases in certain patients having colon cancer, stomach cancer, liver cancer or pancreatic cancer, and also in the case of renal insufficiency. To do this, they use the ELISA assay (PANCEPAP) sold by the company Dynabio (La Gaude, France).

The tumour associated calcium signal transducer 1 marker (Swiss Prot No. P16422, also known as major gastrointestinal tumour-associated protein GA733-2, epithelial cell surface antigen, EpCAM, epithelial glycoprotein, EGP, adenocarcinoma-associated antigen, KSA, KS 1/4 antigen, cell surface glycoprotein Trop-1 or CD326 antigen) was characterized in 1979 by virtue of its ability to be recognized by an antibody directed against colorectal cancer cells[41]. This protein is known by various names, as indicated above, but the most common use is to call it EpCAM. It is a transmembrane protein expressed on the basolateral surface of cells, in certain epithelia and many cancers[42]. As early as 1982 Herlyn et al.[43] showed that the injection of an anti-EpCAM monoclonal antibody could inhibit tumour growth in patients having colorectal cancer. These results led to the development of an antitumour treatment based on an anti-EpCAM antibody called Edrecolomab. This treatment is marketed under the name Panorex™. Moreover, Abe et al.[44] have shown, by ELISA assay, that a soluble form of EpCAM, called MK-1, is increased in the blood stream by 10% in the cancer patients studied.

The cytokeratins are part of the proteins that make up the intermediate filaments of the cytoskeleton of epithelial cells. Currently, more than 20 human cytokeratins have been identified. The cytokeratins 8 (Swiss Prot No. $PO_{5787}$, also known as cytokeratin-8, CK-8, keratin-8 or K8), 18 (Swiss Prot No. P05783, also known as cytokeratin-18, CK-18, keratin-18 or K18) and 19 (Swiss Prot No. P08727, also known as cytokeratin-19, CK-19, keratin-19 or K19) are the most abundant in epithelial cells and are useful tools for the diagnosis of cancer pathological conditions[45]. This clinical importance is linked to the release of cytokeratins by epithelial cells in the apoptotic or proliferation phase. In the case of apoptosis, this release occurs in the form of soluble fragments which seem to appear under the proteolytic action of caspases. Undegraded cytokeratin forms have never been described in the bloodstream. The three cytokeratin assays most commonly used clinically are the tissue polypeptide antigen (TPA) assay, the tissue polypeptide specific antigen (TPS) assay and the CYFRA 21-1 assay. TPA is a broad-spectrum test which measures cytokeratins 8, 18 and 19. The TPS and CYFRA 21-1 assays are more specific and measure, specifically, fragments of cytokeratin 18 and of cytokeratin 19. These three assays detect soluble cytokeratin fragments that may be present on their own or in the form of protein complexes. TPA, TPS or CYFRA-21-1 have been used for the therapeutic follow-up of colorectal cancers, breast cancers, lung cancers, bladder cancers, ovarian cancers, pancreatic cancers, prostate cancers and certain ENT cancers. The assaying of soluble cytokeratin fragments in the blood in fact has a clinical value in screening for relapses or evaluating the response to the therapy used (radiotherapy, chemotherapy, hormone treatment). Regular assaying makes it possible in particular to evaluate the progression of the tumour mass. The amount of soluble blood cytokeratins also has a prognostic aspect with respect to the tumour stage and to the formation of metastases. Currently, the blood assay for cytokeratin most commonly used is CYFRA 21-1. It is highly recommended for the follow-up of patients having non-small cell lung cancer. Various commercially available assays exist for TPA (AB Sangtec Medical Co., Byk-Roland, etc.), TPS (IDL Biotech AB, BEKI Diagnostics, etc.) and CYFRA-21-1 (Roche Diagnostics, CIS Bio-International, Fujirebio Diagnostics, etc.). Moreover, Kim et al.[46] have shown that assaying faecal cytokeratin 19 (DiNonA Inc.) may be useful in screening for gastrointestinal diseases, in combination with a faecal occult blood assay.

The epithelial cadherin marker (Swiss Prot No. P12830, also known as E-cadherin, uvomorulin, cadherin-1, CAM 120/80 or CD324 antigen) is a transmembrane protein that mediates calcium-dependent cell adhesion. It is specifically expressed in to epithelial cells, where it is involved in maintaining their phenotype. The cytoplasmic domain of E-cadherin binds to β-catenin, which is itself bound to the actin filament networks of the cytoskeleton. This E-cadherin/β-catenin binding plays an essential role in stabilizing cell/cell adhesions of the epithelial tissue. The loss of E-cadherin can therefore reduce the cell adhesion and increase the invasive capacity of cancer cells. A reduction in expression of E-cadherin or in β-catenin is generally associated with greater aggressiveness and dedifferentiation of the tumour, in particular for gastrointestinal cancers. Roca et al.[47] have thus shown that patients having colorectal cancer and underexpressing E-cadherin have a more unfavourable prognosis than patients having a normal expression level. As early as 1983, Damsky et al.[48] showed that a soluble form of E-Cadherin could be released by the MCF-7 breast cancer cell line. This soluble form corresponds to the cleavage of the extracellular portion of E-cadherin. Later, Katayama et al.[49] showed that the soluble form of E-cadherin could be released into the bloodstream in the case of cancer, and Willmanns et al.[50] showed that the increase in the amount of E-cadherin in the blood was correlated with the tumour stage in colorectal cancers. A commercial kit is, moreover, proposed by the company Takara BioChemicals (Tokyo, Japan).

The assaying of CEA (carinoembryonic antigen) for the diagnosis of colorectal cancer has been proposed since 1965 by Gold and Freedman[51], but a blood assay for this marker has poor sensitivity for the diagnosis of colorectal cancers at a relatively nonadvanced stage. The assaying of serum CEA is thus especially recommended for evaluating the risk of liver metastases[52] and for therapeutic follow-up. In addition, it is a marker that is not very specific for colorectal cancer; it may in fact be increased in many other cancers (lung, breast, etc.). On the other hand, the assaying of faecal CEA appears to be more sensitive and more specific than the assaying of serum CEA or than the assaying of faecal blood[53]. However, this assaying is not yet proposed routinely.

The reactive antigenic determinants 1116-NS-19-9, more commonly called CA19-9 (carbohydrate antigen 19.9), are carried by high-molecular-weight proteins[54]. The assaying of CA 19-9 in the blood is more specific than that of CEA. The CA 19-9 level in the blood increases in the event of colorectal cancer, of pancreatic cancer and of liver cancer (cholangiocarcinoma), but also in the event of noncancerous pathological to conditions (cholangitis, etc.). Its use in combination with CEA is recommended both at the time of diagnosis of a cancer and for follow-up of the pathological condition.

J. Holmgren et al.[55] have shown that the amount of CA 50 antigen in the serum is increased in the case of colorectal cancer. The CA 50 antigen is defined by its ability to be recognized by a specific monoclonal antibody.

As regards the CA 72 marker, T. L. Klug et al.[56] have shown that the amount of CA 72 antigen in the serum is increased in the case of colorectal cancer. The CA 72 antigen is defined by its ability to be recognized by a specific monoclonal antibody.

Similarly, P. Kuusela et al.[57] have shown that the amount of CA 242 antigen in the serum is increased in the case of colorectal cancer. The CA 242 antigen is defined by its ability to be recognized by a specific monoclonal antibody.

The assaying of testosterone for the diagnosis of colorectal cancer has been proposed in men by M. Holland et al.[58]. These authors have shown a fall in the blood testosterone level in the case of colorectal cancer.

As regards the TIMP-1, or tissue inhibitor of matrix metalloproteinase type-1 marker, patent application US 2007/0020707 describes in particular the assaying of TIMP-1 for the diagnosis of colorectal cancer by assaying in a body fluid.

F. Model et al.[59] showed, in July 2006, during the World Congress on Gastrointestinal Cancer, that it was possible to detect methylated forms of the septin-9 gene in the plasma of patients having colorectal cancer.

M. P. Ebert et al.[60] have shown that the ALX4 gene, or aristaless-like homeobox-4 gene, is more often methylated in the sera of patients having colorectal cancer than in control sera (P<0.0001). Using a threshold value of 41.4 pg/ml, they have obtained a sensitivity of 83.3% and a specificity of 70%.

Villin is described as a blood marker for the diagnosis of colorectal cancer in patent application FR2581456.

C. Bianco et al.[61] have shown that the amount of cripto-1 in the serum is increased in the case of colorectal cancer.

The induction of intestinal tumorigenesis by macrophage migration inhibitory factor (MIF) has been described by Wilson et al.[62]. More recently, it has also been shown, by Lee et al.[63], that MIF is a potential blood marker for the early diagnosis of colorectal cancer.

The protein disulphide isomerase marker (Swiss Prot No. P07237, also known as EC 5.3.4.1, PDI, prolyl 4-hydroxylase subunit beta, cellular thyroid hormone-binding protein or p55) is a multifunctional protein which catalyses the formation, the breaking and the rearrangement of intramolecular disulphide bridges. At the surface of cells, it acts as a reductase and cleaves the disulphide bridges of the proteins attached to the cells. Inside these cells, it is a soluble molecule located in the lumen of the endoplastic reticulum, where it forms and rearranges the disulphide bridges of neosynthesized proteins. It comprises two thioredoxin-type catalytic domains having a characteristic CXXC motif. At high concentration, PDI functions as a chaperone protein which inhibits the aggregation of incorrectly folded proteins. At low concentration, it has an antagonistic role and facilitates the aggregation. PDI also forms the structural subunit of various enzymes, such as prolyl hydroxylase which catalyses the hydroxylation of the proline residues of the pro-alpha chains of procollagen. In patent application EP1724586, PDI has been described as a diagnostic marker for certain cancers, such as colon cancer.

The assaying of intelectin-1 (Swiss Prot No. Q8WWA0, also known as intestinal lactoferrin receptor, galactofuranose-binding lectin, endothelial lectin HL-1 or omentin) for the diagnosis of colorectal cancer has been described in patent application US2003/0082533.

The use of translationally-controlled tumour protein (Swiss Prot No. P13693, also known as TCTP, p23, histamine-releasing factor, HRF or fortilin) and of Prodefensin-A5 (Swiss Prot No. Q01523) as markers in colorectal cancer is described, respectively, in patent applications US2003/0172388 and US 2006/0179496. The term "(Pro)defensin" is intended to mean the precursor, namely the Prodefensin before cleavage, the propeptide, namely the N-terminal moiety after cleavage of Prodefensin, and the mature protein, namely the Defensin, corresponding to the C-terminal moiety after cleavage.

M2-PK is an isoenzyme of pyruvate kinase which is found in dimeric or tetrameric form. The dimeric form is predominant in tumour cells and, for this reason, is called tumour M2-PK. Numerous studies have used the assaying of faecal M2-PK by ELISA as a colorectal cancer marker, for instance Hardt et al.[64]

The use of calgranulin C or S100 A12 protein as a marker for colorectal cancer is described in patent application WO2007/134779.

Sagiv et al.[65] have shown an increase in the expression of CD24 in the case of colorectal cancer.

The colon cancer specific antigen (CCSA)-3 and -4 proteins are serum markers which have also been associated with colorectal cancer by Leman et al.[66]

Finally, the assaying of human faecal haemoglobin is known practice and can be implemented as previously described.

The concentration of the tumour marker other than Prodefensin-A6 will, depending on the marker under consideration, be increased or decreased in the biological sample in which the method of the invention is carried out, relative to the reference values determined for healthy patients.

Preferably, the tumour marker(s) other than Prodefensin-A6 is (are) chosen from: leukocyte elastase inhibitor, ezrin, aminoacylase 1, liver fatty acid-binding protein, intestinal fatty acid-binding protein, apolipoprotein AI, apolipoprotein AII I-plastin, protein disulphide isomerase, intelectin-1, cytokeratin 20, translationally-controlled tumour protein, (Pro)defensin-A5, galectin-3, beta2-microglobulin, CEA, CA19-9, TIMP-1, M2-PK and MIF.

More preferably, the tumour marker(s) other than Prodefensin-A6 is (are) chosen from the markers: L-FABP, beta2-microglobulin, galectin-3, CEA, CA19-9, MIF and I-plastin.

According to one particular embodiment, the method of the invention comprises or consists of the detection of the following markers:
Prodefensin-A6 and L-FABP,
Prodefensin-A6, CA19-9 and CEA,
Prodefensin-A6, beta2-microglobulin and CEA,
Prodefensin-A6, beta2-microglobulin, CA19-9 and CEA,
Prodefensin-A6, beta2-microglobulin, L-FABP and CEA,
Prodefensin-A6, L-FABP, CA19-9 and CEA,
Prodefensin-A6, beta2-microglobulin, CA19-9 and CEA,
Prodefensin-A6, beta2-microglobulin, CA19-9, L-FABP and CEA,
Prodefensin-A6, beta2-microglobulin, CA19-9, galectin-3, L-FABP, MIF and CEA,
Prodefensin-A6, beta2-microglobulin, CA19-9, galectin-3, L-FABP, MIF, I-plastin and CEA.

Of course, the method of the invention may also include the detection of any other colorectal cancer marker known to those skilled in the art.

As indicated previously, the tumour marker(s) of interest is (are) detected either in the form of protein, or in the form of messenger RNA, or by modification of the corresponding DNA (mutation or modification of methylations), it being understood that Prodefensin-A6 is detected only in the form of protein, which may be whole protein or in the form of a protein fragment.

The determination of the presence, in the biological sample, of the "protein" tumour marker of interest can be carried out by any method for determining the presence of a protein in a sample, known to those skilled in the art, such as, for example a biochemical test, including an immunoassay, or by mass spectrometry.

The biochemical test may be any test widely known to those skilled in the art involving molecular intereactions, i.e. reactions between said tumour marker and one or more binding partner(s) specific or not specific for said tumour marker.

Preferably, the biochemical test is an immunoassay known to those skilled in the art, involving immunological reactions between the tumour marker, which is the antigen, and one or more specific binding partner(s), namely the antibodies directed against this antigen.

The binding partners specific or not specific for the tumour marker(s) sought in the method of the invention are any partner capable of binding to this or these marker(s). They are said to be specific when they are capable of binding to these markers with a high specificity, or even a specificity of 100%. They are said to be nonspecific when their specificity of binding to these markers is low and they are then capable of binding to other ligands, such as proteins. By way of example, mention may be made of antibodies, antibody fractions, receptors and any other molecule capable of binding to this marker.

The binding-partner antibodies are, for example, either polyclonal antibodies or monoclonal antibodies.

According to one particular embodiment, the method of the invention uses a binding partner specific for Prodefensin-A6, of sequence SEQ ID No.2. Preferably, the binding partner specific for Prodefensin-A6 is a monoclonal antibody which recognizes any linear or conformational epitope included in the sequence SEQ ID No.2.

Preferably, the monoclonal antibody specifically recognizes a linear epitope of at least the sequence DP (SEQ ID No.4), preferably of at least the sequence EDDPLD (SEQ ID No.6) and of at most the sequence SEQ ID No.2, or else it specifically recognizes a conformational epitope chosen from the following epitopes:

an epitope of at least sequence $X_1X_2X_3X_4X_5X_6X_7X_8R$ (SEQ ID No.7), in which $X_1$ is V or L, $X_2$ is T or L, $X_3$ is P, S or C, $X_4$ is P or S, $X_5$ is W or T, $X_6$ is A, Q, M, C or E, $X_7$ is I, E or D and $X_8$ is F, Y, S or L, and of at most the sequence SEQ ID No.8, SEQ ID No.9, SEQ ID No.10, SEQ ID No.11 or SEQ ID No.12, as indicated in FIG. 4, an epitope of at least the sequence $X_1X_2X_3X_4X_5X_6HX_7$ (SEQ ID No.13), in which $X_1$ is S or T, $X_2$ is C or absent, $X_3$ is T, L or E, $X_4$ is H or R, $X_5$ is I, F or E, $X_6$ is G or V and $X_7$ is C or N, and of at most the sequence SEQ ID No.14, SEQ ID No.15 or SEQ ID No.16, as indicated in FIG. 4, an epitope of at least the sequence $X_1HPX_2X_3X_4X_5X_6X_7$ (SEQ ID No.17), in which $X_1$ is P or W, $X_2$ is W or E, $X_3$ is S, A, Q or W, $X_4$ is M, L, R or P, $X_5$ is H, F, W or G, $X_6$ is V or A and $X_7$ is I or V, and of at most the sequence SEQ ID No.18, SEQ ID No.19, SEQ ID No.20 or SEQ ID No.21, as indicated in FIG. 4, an epitope of at least the sequence $X_1HX_2X_3X_4X_5$ (SEQ ID No.22), in which $X_1$ is Y or N, $X_2$ is E, D or Q, $X_3$ is T, N, R, M or K, $X_4$ is W, H or F and $X_5$ is P or G, and of at most the sequence SEQ ID No.23, SEQ ID No.24, SEQ ID No.25, SEQ ID No.26, SEQ ID No.27, SEQ ID No.28 or SEQ ID No.29, as indicated in FIG. 4.

The monoclonal antibodies which specifically recognize the propeptide part of Prodefensin-A6 are novel and constitute another subject of the invention.

According to one embodiment, the monoclonal antibodies of the invention specifically recognize an epitope having at least the sequence SEQ ID No.4, preferably at least the sequence SEQ ID No.6 (epitope 1), and at most the sequence SEQ ID No.2.

According to another embodiment, the anti-Prodefensin-A6 monoclonal antibodies of the invention specifically recognize an epitope chosen from the following epitopes:

an epitope of at least the sequence SEQ ID No.7, in which $X_1$ is V or L, $X_2$ is T or L, $X_3$ is P, S or C, $X_4$ is P or S, $X_5$ is W or T, $X_6$ is A, Q, M, C or E, $X_7$ is I, E or D and $X_8$ is F, Y, S or L, and of at most the sequence SEQ ID No.8, SEQ ID No.9, SEQ ID No.10, SEQ ID No.11 or SEQ ID No.12 (epitope 2), an epitope of at least the sequence SEQ ID No.13, in which $X_1$ is S or T, $X_2$ is C or absent, $X_3$ is T, L or E, $X_4$ is H or R, $X_5$ is I, F or E, $X_6$ is G or V and $X_7$ is C or N, and of at most the sequence SEQ ID No.14, SEQ ID No.15 or SEQ ID No.16 (epitope 3), an epitope of at least the sequence SEQ ID No.17, in which $X_1$ is P or W, $X_2$ is W or E, $X_3$ is S, A, Q or W, $X_4$ is M, L, R or P, $X_5$ is H, F, W or G, $X_6$ is V or A and $X_7$ is I or V, and of at most the sequence SEQ ID No.18, SEQ ID No.19, SEQ ID No.20 or SEQ ID No.21 (epitope 4), an epitope of at least the sequence SEQ ID No.22, in which $X_1$ is Y or N, $X_2$ is E, D or Q, $X_3$ is T, N, R, M or K, $X_4$ is W, H or F and $X_5$ is P or G, and of at most the sequence SEQ ID No.23, SEQ ID No.24, SEQ ID No.25, SEQ ID No.26, SEQ ID No.27, SEQ ID No.28 or SEQ ID No.29 (epitope 5).

According to yet another embodiment, the method of the invention uses a monoclonal antibody specific for an epitope 1 and a monoclonal antibody specific for an epitope 2, 3, 4 or 5. Preferably, the method of the invention uses a monoclonal antibody specific for an epitope 1 and a monoclonal antibody specific for an epitope 2 or 4. More preferably, the method of the invention uses a monoclonal antibody specific for an epitope 1 and a monoclonal antibody specific for an epitope 2.

The term "epitope" is intended to mean a peptide having at least the sequences as defined by the sequences SEQ ID Nos. 1 to 29, and at most 10, 8, 6 or 4 additional amino acids distributed on either side of the sequence under consideration, in a homogeneous or nonhomogeneous manner, or else on just one side, and also the analogues, homologues and structural equivalents thereof.

Generally, the term "analogue" refers to peptides having a sequence and a native polypeptide structure exhibiting one or more amino acid additions, substitutions (generally conservative in terms of nature) and/or deletions, relative to the native molecule, insofar as the modifications do not destroy the antigenic reactivity.

The analogues that are particularly preferred include substitutions that are conservative in nature, i.e. substitutions which take place in an amino acid family. Specifically, amino acids are generally divided up into four families, namely (1) acidic amino acids such as aspartate and glutamate, (2) basic amino acids such as lysine, arginine and histidine, (3) nonpolar amino acids such as alanine, leucine, isoleucine, proline, phenylalanine, methionine and tryptophan, and (4) uncharged polar amino acids such as glycine, asparagine, glutamine, cysteine, serine, threonine and tyrosine. Phenylalanine, tryptophan and tyrosine are sometimes classified as aromatic amino acids. For example, it can be reasonably predicted that an isolated replacement of leucine with isoleucine or valine, of an aspartate with a glutamate, or of a threonine with a serine, or a similar conservative replacement of one amino acid with another amino acid that is structurally related, will have no major effect on the biological activity. Those skilled in the art will readily determine the regions of the peptide molecule of interest that can tolerate a change with reference to Hopp/Woods and Kyte-Doolite plots, well known in the art.

The term "homology" is intended to mean the percentage identity between two peptide molecules. Two amino acid sequences are "substantially homologous" to one another when the sequences exhibit at least 60%, preferably at least 75%, more preferably at least 80-85%, more preferably at least 90% and more preferably at least 95-98% or more sequence identity over a defined length of the peptide molecules.

The term "structural equivalent" is intended to mean any linear or nonlinear peptide sequence included in the protein of interest, having the same three-dimensional structure as the conformational epitope of interest, such as the epitopes of sequences SEQ ID Nos. 7 to 29, while at the same time retaining the antigenic reactivity. Such a to "structural equivalent" can be readily obtained by those skilled in the art from the conformational epitope of interest, using a bioinformatic system which makes it possible to find 3D structural or substructural similarities in proteins, such as the SuMo[67] or Superimposé[68] systems.

The polyclonal antibodies can be obtained by immunization of an animal with the tumour marker concerned, followed by recovery of the desired antibodies in purified form, by taking serum from said animal, and separation of said antibodies from the other serum constituents, in particular by affinity chromatography on a column to which an antigen specifically recognized by the antibodies, in particular said marker, is attached.

The monoclonal antibodies can be obtained by the hydridoma technique, the general principle of which is summarized hereinafter.

Firstly, an animal, generally a mouse, is immunized with the tumour marker of interest, the B lymphocytes of said animal then being capable of producing antibodies against said antigen. These antibody-producing lymphocytes are then fused with "immortal" myeloma cells (murine in the example) so as to produce hybridomas. Using the heterogeneous mixture of cells thus obtained, a selection of cells capable of producing a particular antibody and of multiplying indefinitely is then carried out. Each hybridoma is multiplied in the form of a clone, each resulting in the production of a monoclonal antibody of which the properties of recognition with respect to said tumour marker may be tested, for example, by ELISA, by one-dimensional or two-dimensional Western blotting, by immunofluorescence, or by means of a biosensor. The monoclonal antibodies thus selected are subsequently purified, in particular according to the affinity chromatography technique described above.

The monoclonal antibodies may also be recombinant antibodies obtained by genetic engineering, by means of techniques well known to those skilled in the art.

Examples of anti-defensin-A6 molecules are known and are available in particular in the Alpha Diagnostic International Inc. catalogue, rabbit anti-defensin-A6 polyclonal antibody, Cat. No. HDEFA61-A. No monoclonal antibody directed against Prodefensin-A6 is available to date.

Examples of anti-leukocyte elastase inhibitor antibodies are known and are available in particular in the Abcam catalogue, rabbit anti-LEI polyclonal antibody, Cat. No. Ab47731. An anti-LEI monoclonal antibody, clone ELA-1, has been described in the article by Yasumatsu et al.[69].

Examples of anti-ezrin antibodies are known and are available in particular in the Abcam catalogue, anti-ezrin monoclonal antibody, clone 3C12, Cat. No. Ab4069 and rabbit anti-ezrin polyclonal antibody, Cat. No. Ab47418.

Examples of anti-aminoacylase 1 antibodies are known and are available in particular in the Abnova catalogue, anti-aminoacylase 1 monoclonal antibody, clone 4F1-B7, Cat. No. H00000095-M01, and in the Abcam catalogue, chicken anti-aminoacylase 1 polyclonal antibody, Cat. No. Ab26173.

Examples of anti-liver fatty acid-binding protein antibodies are known and are available in particular in the Abcam catalogue, anti-L-FABP monoclonal antibody, clone 6B6, Cat. No. Ab10059, and rabbit anti-L-FABP polyclonal antibody, Cat. No. Ab7807.

Examples of anti-intestinal fatty acid-binding protein antibodies are known and are available in particular in the R&D Systems catalogue, anti-I-FABP monoclonal antibody, clone 323701, Cat. No. MAB3078, and in the Abcam catalogue, rabbit anti-1-FABP polyclonal antibody, Cat. No. Ab7805.

Examples of anti-apolipoprotein AI antibodies are known and are available in particular in the Biodesign Meridian Life Sciences catalogue, anti-Apo AI monoclonal antibody, clone 4A90, Cat. No. H45402M and goat anti-Apo AI polyclonal antibody, Cat. No. K45252P.

Examples of anti-apolipoprotein AII antibodies are known and are available in particular in the US Biological catalogue, anti-Apo AII monoclonal antibody, clone 1402, Cat. No. A2299-31C and in the Biodesign Meridian Life Sciences catalogue, goat anti-Apo AII polyclonal antibody, Cat. No. K74001P.

Examples of anti-I-plastin polyclonal antibodies are known and are available in particular in the Santa Cruz Biotechnology catalogue. The rabbit polyclonal antibody H-300 (Cat. No. sc-28531) reacts with I-plastin, L-plastin and T-plastin. The applicant has developed monoclonal antibodies directed against I-plastin.

Examples of anti-beta2-microglobulin, anti-CEA, anti-CA19-9 and anti-testosterone antibodies are known and are in particular used in the applicant's assay kits, respectively Vidas® β2-Microglobulin, Vidas® CEA, Vidas® CA19-9™ and Vidas® Testosterone.

Examples of anti-proteasome 20S antibodies are known and are available in particular in the Affinity Research Products catalogue.

Examples of anti-galectin-3, anti-L-lactate dehydrogenase chain B, anti-calreticulin, anti-tumour-associated calcium signal transducer 1, anti-keratin type II cytoskeletal 8, anti-keratin type I cytoskeletal 18, anti-keratin type I cytoskeletal 19, anti-epithelial-cadherin, anti-villin and anti-TIMP-1 antibodies are known and are available in particular in the Abcam catalogue.

Examples of anti-regenerating islet-derived protein 3 alpha antibodies are known and are in particular used in the Dynabio assay kits (La Gaude, France).

Examples of anti-CA 242, anti-CA 50 and anti-CA 72-4 antibodies are known and are available in particular in the Fujirebio catalogue.

Examples of anti-intelectin-1 antibody are known and are available in particular in the Alexis Biochemicals catalogue, anti-intelectin-1 monoclonal antibody, clone Saly-1, Cat. No. ALX-804-850-C100 and rabbit anti-intelectin-1 polyclonal antibody, Cat. No. ALX-210-941.

Examples of anti-cytokeratin 20 antibodies are known and are available in particular in the Abcam catalogue, anti-cytokeratin 20 monoclonal antibody, clone Ks20.8, Cat. No. Ab962 and rabbit anti-cytokeratin 20 polyclonal antibody, Cat. No. Ab36756.

Examples of anti-TCTP antibodies are known and are available in particular in the Abnova catalogue, anti-TCTP monoclonal antibody, clone 3C7, Cat. No. 157H00007178-M01 and anti-TCTP polyclonal antibody, Cat. No. 157H00007178-A01.

Examples of anti-defensin-A5 antibodies are known and are available in particular in the Santa Cruz Biotechnology catalogue, anti-defensin-A5 monoclonal antibody, clone 8C8, Cat. No. sc-53997, and in the Alpha Diagnostic International Inc. catalogue, rabbit anti-defensin-A5 polyclonal antibody, Cat. No. HDEFA51-A.

The binding partners which are specific or not specific for the tumour marker(s) sought in the method of the invention may be used as a capture reagent, as a detection reagent or as capture and detection reagents.

According to one embodiment, the binding partner specific for Prodefensin-A6 is used for the capture of Prodefensin-A6, which makes it possible to improve the specificity of the diagnostic method of the invention.

Preferably, the monoclonal antibody which specifically recognizes an epitope 1 is used in capture and/or the monoclonal antibody which specifically recognizes an epitope 2, 3, 4 or 5, preferably 2, is used in detection.

The visualization of the immunological reactions, i.e. of the tumour marker/binding partner binding, may be carried out by any means of detection, such as direct or indirect means.

In the case of direct detection, i.e. without the involvement of a label, the immunological reactions are observed, for example, by surface plasmon resonance or by cyclic voltametry on an electrode bearing a conductive polymer.

The indirect detection is carried out by means of labelling, either of the "revealing reagent" binding partner, or of the tumour marker of interest itself. In the latter case, this is then described as a competition method.

The term "labelling" is intended to mean the attachment of a label reagent capable of directly or indirectly generating a detectable signal. A nonlimiting list of these label reagents comprises:

enzymes which produce a signal that can be detected, for example, by colorimetry, fluorescence or luminescence, such as horseradish peroxydase, alkaline phosphatase, β-galactosidase or glucose-6-phosphate dehydrogenase, chromophores such as fluorescent or luminescent compounds or dyes, radioactive molecules such as $^{32}P$, $^{35}S$ or $^{125}I$ and fluorescent molecules such as Alexa or phycocyanins Indirect detection systems may also be used, such as, for example, ligands capable of reacting with an antiligand. Ligand/antiligand pairs are well known to those skilled in the art, this being the case, for example, of the following pairs: biotin/streptavidin, hapten/antibody, antigen/antibody, peptide/antibody, sugar/lectin, polynucleotide/sequence complementary to the polynucleotide. In this case, it is the ligand which carries the binding partner. The antiligand may be directly detectable by means of the label reagents described in the previous paragraph, or may itself be detectable by means of a ligand/antiligand.

These indirect detection systems may result, under certain conditions, in an amplification of the signal. This signal amplification technique is well known to those skilled in the art, and reference may be made to the prior patent applications FR98/10084 or WO-A-95/08000 by the applicant or to the article by Chevalier et al.[70].

Depending on the type of labelling used, those skilled in the art will add reagents that make it possible to visualize the labelling.

By way of example of immunoassays as defined above, mention may be made of "sandwich" methods such as ELISA, IRMA and RIA, "competition" methods and direct immunodetection methods such as immunohistochemistry, immunocytochemistry, Western blotting and Dot blotting.

When the binding partner specific for Prodefensin-A6 is used in capture in a "sandwich" assay, for example the antibody specific for epitope 1, either a binding partner specific for the mature part of Prodefensin-A6 (amino acids 66 to 100), or a binding partner which recognizes an epitope of the propeptide part of Prodefensin-A6 (amino acids 20-65), other than that recognized by the binding partner used for the capture, will be used in detection.

Mass spectrometry can also be used for detecting, in the biological fluid, the tumour marker(s) sought in the method of the invention. The principle of spectrometry is widely known to those skilled in the art and is described, for example, in Patterson[71].

To do this, the biological sample, which may or may not have been pretreated, is analysed in a mass spectrometer and the spectrum obtained is compared with that of the tumour marker(s) sought in the method of the invention. An example of pretreatment of the sample consists in passing it over an immunocapture support comprising one of the binding partners for the tumour marker(s) sought in the method of the invention, for example an antibody directed against the tumour marker(s) sought in the method of the invention. Another example of pretreatment of the sample may be prefractionation of the biological sample in order to separate the proteins of the sample from one another. In techniques well known to those skilled in the art, the predominant proteins of the sample may, for example, first of all be depleted.

The determination of the presence, in the biological sample, of the "mRNA" tumour marker of interest may be carried out by any method for determining the presence of mRNA in a sample, namely either direct detection of the mRNA, or indirect detection of the mRNA, or any other method for determining the presence of an RNA in a sample, known to those skilled in the art.

The term "direct detection of the mRNA" is intended to mean the demonstration of the mRNA itself in the biological sample.

The direct detection of the mRNA in the biological sample may be carried out by any means known to those skilled in the art, such as, for example, by hybridization with a binding partner specific for the mRNA, where appropriate after amplification by the PCR or NASBA technique.

The term "hybridization" is intended to mean the process during which, under suitable conditions, two nucleotide fragments bind to one another with stable and specific hydrogen bonds so as to form a double-stranded complex. These hydrogen bonds form between the complementary bases adenine (A) and thymine (T) (or uracil (U)) (referred to as an A-T bond) or between the complementary bases guanine (G) and cytosine (C) (referred to as a G-C bond). The hybridization of two nucleotide fragments may be complete (reference is then made to complementary nucleotide fragments or sequences), i.e. the double-stranded complex obtained during this hybridization comprises only A-T bonds and C-G bonds. This hybridization may be partial (reference is then made to sufficiently complementary nucleotide fragments or sequences), i.e. the double-stranded complex obtained comprises A-T bonds and C-G bonds which make it possible to form the double-stranded complex, but also bases that are not bonded to a complementary base. The hybridization between two nucleotide fragments depends on the operating conditions that are used, and in particular the stringency. The stringency is defined in particular as a function of the base composition of the two nucleotide fragments, and also by the degree of mismatching between two nucleotide fragments. The stringency can also depend on the reaction parameters, such as the concentration and the type of ionic species present in the hybridization solution, the nature and the concentration of denaturing agents and/or the hybridization temperature. All these data are well known and the appropriate conditions can be determined by those skilled in the art. In general, depending on the length of the nucleotide fragments that it is desired to hybridize, the hybridization temperature is between approximately 20 and 70° C., in particular between 35 and 65° C., in a saline solution at a concentration of approximately 0.5 to 1 M. The binding partners which are specific or not specific for the mRNA are any partner capable of binding to this mRNA. By way of example, mention may be made of nucleic probes, amplification primers, and any other molecule capable of binding to this mRNA.

The term "hybridization probe" is intended to mean a nucleotide fragment comprising from 5 to 100 nucleic units, in particular from 10 to 35 nucleic units, having a hybridization specificity under given conditions so as to form a hybridization complex with the material specific for the target gene of interest. The hybridization probe may comprise a label enabling its detection.

For the purpose of the present invention, the term "amplification primer" is intended to mean a nucleotide fragment comprising from 5 to 100 nucleic units, preferably from 15 to 30 nucleic units, enabling the initiation of an enzymatic polymerization, such as, in particular, an enzymatic amplification reaction. The term "enzymatic amplification reaction" is intended to mean a process that generates multiple copies of a nucleotide fragment via the action of at least one enzyme. Such amplification reactions are well known to those skilled in the art and mention may in particular be made of the following techniques:

PCR (polymerase chain reaction), as described in patents U.S. Pat. Nos. 4,683,195, 4,683,202 and 4,800,159, NASBA (nucleic acid sequence-based amplification) with patent application WO 91/02818, and TMA (transcription mediated amplification) with patent U.S. Pat. No. 5,399,491.

The term "detection" is intended to mean either a physical method, or a chemical method with an intercalating dye such as SYBR® Green I or ethidium bromide, or a method of detection using a label. Many detection methods exist for detecting nucleic acids[72]. The appropriate labels are as defined above.

For the purpose of the present invention, the hybridization probe may be a to "detection" probe. In this case, the "detection" probe is labelled by means of a label as defined above. By virtue of the presence of this label, it is possible to detect the presence of a hybridization reaction between a given detection probe and the transcript to be detected.

The detection probe may in particular be a "molecular beacon" detection probe[73]. These "molecular beacons" become fluorescent during hybridization. They have a stem-loop structure and contain a fluorophore and a quencher group. The binding of the specific loop sequence with its complementary target nucleic acid sequence causes unfolding of the stem and the emission of a fluorescent signal during excitation at the appropriate wavelength.

The hybridization probe may also be a "capture" probe. In this case, the "capture" probe is immobilized or can be immobilized on a solid support by any appropriate means, i.e. directly or indirectly, for example by covalence or adsorption. The appropriate solid supports are known to those skilled in the art, and, by way of examples, mention may be made of synthetic materials or natural materials, latices, magnetic particles, metal derivatives, gels, etc. The solid support may be in the form of a microtitration plate, a membrane as described in application WO-A-94/12670 or a particle. It is also possible to immobilize several different capture probes on the support, each capture probe being specific for a target transcript. In particular, it is possible to use, as support, a biochip on which a large number of probes may be immobilized.

The immobilization of the probes on the support is also known to those skilled in the art, and mention may be made of a deposit of probes by direct transfer, microdeposition, in situ synthesis and photolithography.

The demonstration, in the biological sample, of the DNA modifications or anomalies in the gene encoding the tumour marker of interest may be carried out by any method for determining DNA alterations in a sample, namely either the direct detection of mutations, or the demonstration of alterations in the methylation profile of the loci of interest, or any other method for determining DNA alterations in a sample, known to those skilled in the art.

The mutations may include point substitutions of one nucleotide with another, deletions of one or more nucleotides and insertions of one or more nucleotides. The mutations may be located in the coding portion of the gene of the tumour marker of interest, or in the 5' and 3' noncoding portions, such as the transcription promoter region or the transcription termination region.

The strategies for demonstrating a mutation are based on molecular biology techniques and comprise steps of DNA extraction, amplification by PCR or another amplification technique, hybridization and/or sequencing. In the case of colorectal cancer, the following method has been successfully used to detect mutations in faecal DNA: concentration of the DNA by precipitation, enrichment in the target using capture oligonucleotides on magnetic beads, PCR amplification of the genes of interest, solid-phase sequencing for identifying point mutations[74]. The deletions were identified with respect to the difference in size between the expected reference fragment and the mutated fragment. Imperiale et al.[74] have described a panel of 21 mutations located in the K-ras, APC and p53 genes, which makes it possible to detect 16/31 of invasive cancers.

Other DNA markers used are the BAT-26 deletion, which is a marker for instability of microsatellites and highly amplifiable DNA called long DNA (L-DNA), which is not a specific marker but which appears to reflect the disorganized apoptosis of exfoliated tumour cells in the colonic lumen[75]. These markers are not satisfactory, either in terms of their sensitivity or in terms of their specificity.

As previously indicated, the DNA alterations may also correspond to a modification of the methylation profile of the gene corresponding to the tumour marker of interest. The modification of the methylation profile may correspond to a hypomethylation (decrease in the number of methylations) or to a hypermethylation (increase in the number of methylations). The altered units may be located in the coding portion of the gene of the tumour marker of interest, or in the 5' and 3' noncoding portions, such as the transcription promoter region or the transcription termination region.

The analysis of the DNA methylation may be carried out using techniques based on qualitative and/or quantitative PCR, such as MSP (methylation-specific PCR), bisulphite sequencing, digestion with a methylation-sensitive restriction enzyme coupled with PCR, COBRA (combined bisulphite restriction analysis) and Ms-SNuPE (methylation-sensitive single nucleotide primer extension). All these techniques have been reviewed comparatively and in detail in a methodology article[76].

In the literature, several hypermethylated genes have been reported in the case of colorectal cancer. By way of example, mention may be made of the $ALX_4$ (aristaless-like homeobox-4) gene[60], the promoter region of the TPEF/HHP1 (transmembrane protein containing epidermal growth factor and follistatin domain) gene[77] or else the septin-9 gene[78].

When, in the method of the invention, at least two markers are detected, they may be demonstrated separately, for example by means of different immunoassay determinations, or else simultaneously, in a multiplex assay.

When, in the method of the invention, two markers of different nature are detected, for example a protein marker and an mRNA marker, two different detection methods, chosen from those described above, may be used. They may also be detected simultaneously, in the same detection medium and under the same reaction conditions, as described in patent application WO 03/104490. The steps of the detection method described in this patent application, which consists in simultaneously detecting hybridization and immunological reactions in a sample that may contain target analytes constituted of at least one nucleic acid and of at least one other ligand of different nature, consist in:
  (i) depositing a known volume amount of the sample diluted in a reaction buffer, on a capture surface pre-coated with capture partners for said target analytes, said capture partners comprising at least one nucleic probe and at least one antiligand,
  (ii) reacting at a temperature of between 15° C. and 60° C., and
  (iii) visualizing the hybridization and immunological reactions thus obtained.

The biological sample may require a particular treatment because it may contain the tumour marker(s) sought in the method of the invention, as such, or else it may contain circulating tumour cells which contain the markers sought in the method of the invention and/or circulating tumour cells which are capable of secreting the marker(s) sought in the method of the invention.

Thus, according to one embodiment of the invention, the biological sample is pretreated in order to isolate the circulating tumour cells contained in said fluid.

The expression "isolate circulating tumour cells" is intended to mean obtain a cell fraction enriched in circulating tumour cells.

The treatment of the biological sample in order to isolate the circulating tumour cells can be carried out by cell sorting in a flow cytometer, by enrichment on Ficoll, by enrichment with magnetic beads covered with specific antibodies, or by any other method of specific enrichment known to those skilled in the art.

In the case of blood as biological sample, the circulating tumour cells may be isolated by means of a technique of cell separation on Ficoll combined with depletion of the blood cells using anti-CD45 antibodies coupled to magnetic beads (Dynal Biotech ASA, Norway).

The detection of the tumour marker(s) sought in the method of the invention can then be carried out directly using circulating tumour cells isolated from the biological sample, for example by immunocytochemical labelling of these cells with an antibody against tumour marker(s) sought in the method of the invention, after having deposited the circulating tumour cells on a slide by cytospin. The detection of the tumour marker(s) sought in the method of the invention may also be carried out directly in the circulating tumour cells using the flow cytometry method as described in Métézeau et al.[79].

Under these conditions, said circulating cells can be treated under conditions which make it possible to block the tumour marker(s) sought in the method of the invention, inside said cells. Such a treatment is described by Mathieu et al.[80].

The detection of the tumour marker(s) sought in the method of the invention is then carried out after having made the cell membrane permeable so as to allow entry of the binding partners specific for the marker(s) sought in the method of the invention.

The direct detection of the tumour marker(s) used in the method of the invention, based on the circulating cells, may also be carried out by means of an ELISPOT method, for example by means of the method described in patent application WO 03/076942 filed by the applicant. This method is a method for detecting and/or quantifying circulating tumour cells of a biological sample, which are capable of releasing or secreting, in vitro, one or more tumour marker(s), comprising the steps consisting in:

(i) depositing an amount of said cells at the bottom of a culture surface to which at least one binding partner specific for said tumour marker(s) is attached, (ii) culturing said cells under conditions such that they release or secrete said tumour markers, which are immunocaptured at the bottom of the culture surface, (iii) removing the cells by washing, (iv) adding at least one labelled conjugate specific for said tumour markers, and (v) visualizing the labelling thus obtained.

The direct detection of the tumour marker(s) used in the method of the invention in the tumour cells may also be carried out in the culture medium of said cells after having cultured them under conditions such that they secrete tumour marker(s) used in the method of the invention.

The culture conditions for release or the expression of the tumour markers are conventional conditions such as 37° C. under a humid atmosphere and at 5% $CO_2$.

When the biological sample is a solid sample, the presence of the tumour marker(s) may also be shown in vivo, in situ in the tumours.

In order to show the presence of a tumour marker in a tumour in vivo, any imaging method known to those skilled in the art may be used. For this, a binding partner for said tumour marker may be coupled to an imaging tracer.

The term "coupling of the binding partners to an imaging tracer" is intended to mean the attachment of a tracer capable of being detected by any imaging method known to those skilled in the art, and of directly or indirectly generating a detectable signal. Thus, the tracer may be a radioactive tracer such as technetium-99. In this case, the organ which has the primary cancer or the metastases will bind the tumour marker and its tracer. The radiation emitted by the organ can be filmed with a special camera, for example a gamma-camera. The instrument collects the scintillations generated by the radioactive substance and thus makes it possible to visualize the organ.

In another method of the invention, the tracer may comprise a positron-emitting radioactive substance (fluorine 18). The images will then be acquired by a positron emission tomography system.

In another preferred method of the invention, the partner of the tumour marker(s) may be coupled to nanoparticles. By way of example, they may be supramagnetic nanoparticles; for example, anionic magnetic nanoparticles for use in direct cell labelling and in vivo detection by nuclear magnetic resonance imaging. They may also be gold nanoparticles.

By virtue of the methods of the invention which make it possible to detect the tumour marker in vivo, it will be possible to visualize the areas in the body where there has been binding of the tumour marker binding partner, the cancers producing the tumour marker, and in particular colorectal cancer, and also the locations of their remote metastases and the lymph node involvement.

The method of the invention can be used both for early diagnosis, and for screening, therapeutic follow-up, prognosis and relapse diagnosis in relation to colorectal cancer since only the cancer cells secrete Prodefensin-A6 and this production depends on the grade of the cancer, which constitutes another subject of the invention.

Figure 5:
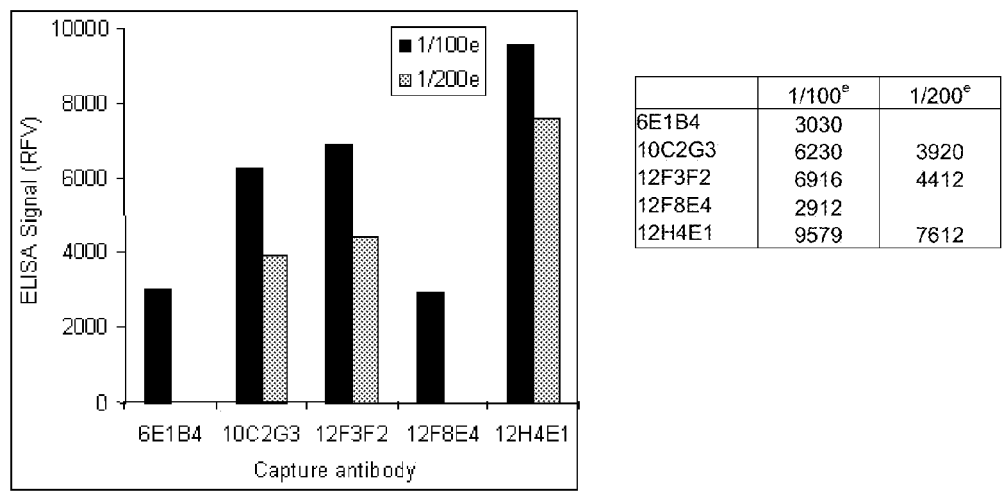
Figure 6:
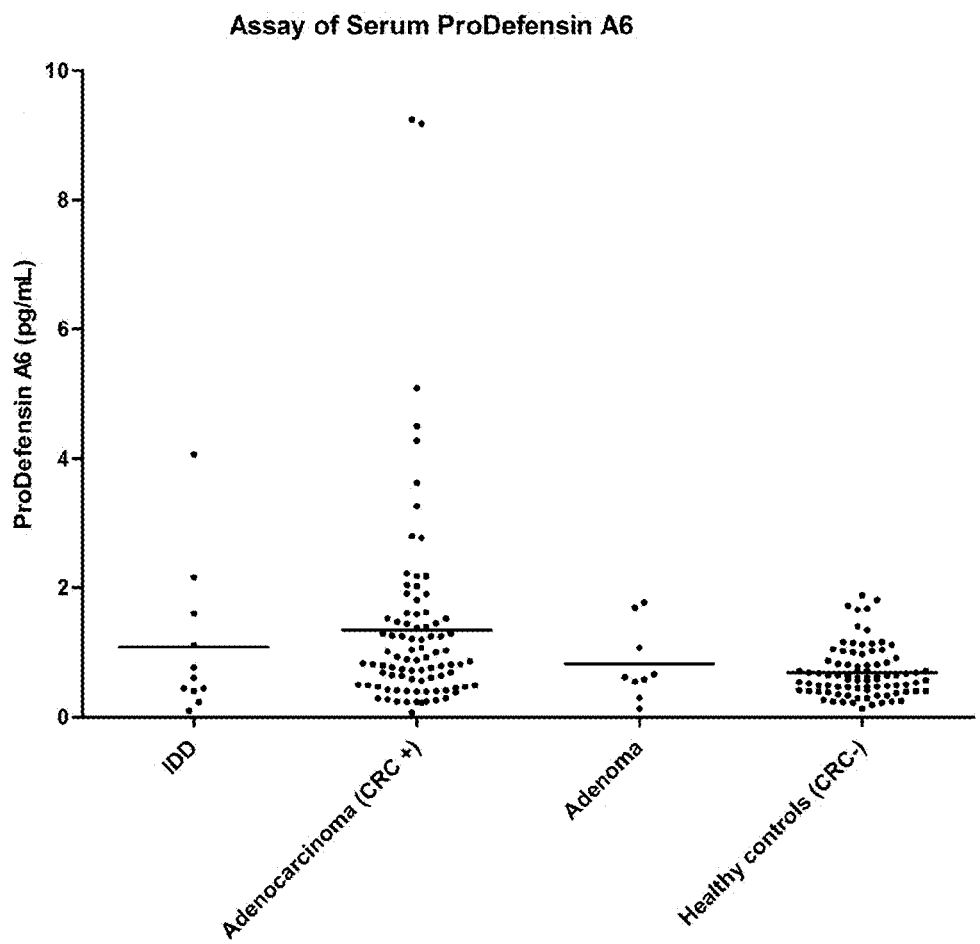

The invention will be understood more clearly by means of the following examples given by way of nonlimiting illustration, and also by means of the appended FIGS. 1 to 6, in which:

FIG. 1 represents the comparison, by the Western blotting technique, of the nine anti-Prodefensin-A6 monoclonal antibodies. The graphs show the signals corresponding to the volume of the band (in intensity*$mm^2$) for the Prodefensin-A6 peptide (SEQ ID No.1, 7 ng/well) (FIG. 1A) and for the Prodefensin-A6 protein secreted into the transfected 293T culture supernatants (FIG. 1B). The exact values of the band volumes are indicated in the table (FIG. 1C);

FIG. 2 represents the comparison, by the dot-blotting technique, of the nine anti-Prodefensin-A6 monoclonal antibodies. The graphs show the signals corresponding to the average volume of two spots (in intensity*$mm^2$) for the Prodefensin-A6 peptide (SEQ ID No.1) (FIG. 2A) and for the Prodefensin-A6 propeptide (SEQ ID No.3) (FIG. 2B). The exact values of the band volumes are indicated in the table (FIG. 2C). The ratio*100 given in this table is calculated according to the formula: Prodefensin-A6 propeptide signal/Prodefensin-A6 peptide signal*100;

FIG. 3 is a graph relating to the analysis of the recognition of the Prodefensin-A6 propeptide by the indirect ELISA technique. The exact values of the ELISA signal in absorbance units are indicated in the table next to the graph;

FIG. 4 recapitulates the sequences recognized by each of the anti-Prodefensin-A6 antibodies $1H_8C9$, 11B2D2, 11E8C9 and 13E7F3. The amino acid sequence of each motif displayed by a phage library and binding to the antibody studied is given in the "immunoreactive motifs" box. For each antibody, these immunoreactive motifs are aligned in order to determine the consensus sequence which is indicated in bold;

FIG. 5 represents the analysis of the reactivity by sandwich ELISA of the five anti-Prodefensin-A6 monclonal antibodies directed against epitope 1 with the 1H8C9 detection antibody. The antigen used is the transfected 293T culture supernatant containing secreted Prodefensin-A6. This supernatant was diluted to 1/100 or 1/200. The exact values of the ELISA signal in RFV are indicated in the table next to the graph;

FIG. 6 is a graph relating to the assaying by ELISA of Prodefensin-A6, in pg/ml, in the serum of patients having a colorectal adenocarcinoma (CRC+), of healthy individuals (CRC−), of patients having an inflammatory digestive disease (IDD) and of patients having a colorectal adenoma;

FIG. 7 represents the optimization of the SPE fractionation on MCX cartridges for the peptide EPLQAEDDPLQAK (SEQ ID No.30) of Prodefensin-A6. The graphs represent the area of the peak corresponding to transition 727/556 of the peptide as a function of the pH of the buffer used to carry out the fractionation on an MCX cartridge. FIG. 7A: Prodefensin-A6 dissolved in water; FIG. 7B: Prodefensin-A6 dissolved in human serum from healthy individuals.

Example 1

Cloning of the Genes Encoding the Tumour Markers and Expression of Recombinant Proteins For the aminoacylase-1, LEI, L-FABP, ezrin, I-plastin, Gal-3, villin, I-FABP and calreticulin tumour markers, the cDNA amplification and cloning, the construction of the expression vectors and also the expression and purification of the recombinant proteins were described in detail in patent application WO2009/024691.

1. Expression of the Prodefensin-A6 Protein in Human Cells by Transfection

An expression vector containing the cDNA of the Prodefensin-A6 gene (pCMV6-XL5 DEFA6) was purchased from the company Origene (Cat. No. SC303095). This vector makes it possible to express the Prodefensin-A6 protein under the control of the CMV promoter after introduction into mammanian cells.

HEK 293T human embryonic kidney cells were maintained in culture in DMEM medium containing 10% FCS, at 37° C. with 5% $CO_2$. The cell layers between 50% and 70% confluence were transfected with the pCMV6-XL5 DEFA6 expression plasmid using one of the following two transfection reagents: Lipofectamine LTX sold by Invitrogen (Cat No. 15338-100) or TransIT LT-1 (Cat No. MIR2300) sold by Euromedex. In both cases, the transfections were carried out according to the procedure provided by the producers of the reagent. After transfection, the cultures were incubated for 48 h in order to allow the production of the Prodefensin-A6 protein. Next, the culture supernatant was harvested, centrifuged, and then filtered so as to remove cell debris. The Prodefensin protein secreted into the culture supernatant underwent all the post-translational modifications necessary for its folding; it is native. It is this supernatant that was used as a source of Prodefensin-A6 protein in the screening of the anti-Prodefensin-A6 monoclonal antibodies and in the characterization of these antibodies.

2. Chemical Synthesis of Peptides

Three peptides corresponding to various parts of the Prodefensin-A6 protein were obtained by chemical synthesis according to procedures well known to those skilled in the art (NeoMPS). The peptide of which the sequence is indicated in SEQ ID No.1 corresponds to the entire sequence of Prodefensin-A6 without the signal peptide which is cleaved during the translocation of the polypeptide chain to the endoplasmic reticulum. This peptide is called Prodefensin-A6 peptide or Prodefensin-A6 precursor. The peptide of which the sequence is indicated in SEQ ID No.2 corresponds to the whole of the propeptide part of the Prodefensin-A6 precursor. This peptide is called Prodefensin-A6 propeptide or propeptide part of Prodefensin-A6. The peptide of which the sequence is indicated in SEQ ID No.3 corresponds to virtually the whole of the propeptide part of the Prodefensin-A6 precursor. Four amino acids of the N-terminal end are not included in the sequence. This peptide is easier to produce in large amounts than the peptide of sequence SED ID No. 2 and was used as a replacement when the presence of the four amino acids is not essential.

```
SEQ ID No. 1:
EPLQAEDDPLQAKAYEADAQEQRGANDQDFAVSFAEDASSSLRALGSTR
AFTCHCRRSCYSTEYSYGTCTVMGINHRFCCL

SEQ ID No. 2:
EPLQAEDDPLQAKAYEADAQEQRGANDQDFAVSFAEDASSSLRALGS

SEQ ID No. 3:
AEDDPLQAKAYEADAQEQRGANDQDFAVSFAEDASSSLRALGS
```

Example 2

Production of Monoclonal Antibodies Directed Against the Tumour Markers

1. Animal Model

The immunization experiments were carried out in female BALB/c ($H-2^d$) mice aged 6 to 8 weeks at the time of the first immunization.

2 Immunogens and Immunizations

In order to increase the immune responses obtained in the mice and to be able to generate monoclonal antibodies, the tumour markers were produced in the form of recombinant proteins or of synthetic peptides produced according to the procedures described in example 1. The LDH protein was obtained from the company SciPac (Cat. No. 103-133). When the synthetic peptides were used as immunogen, they were coupled to carrier proteins such as bovine serum albumin (BSA) or KLH (keyhole limpet haemocyanin). These proteins were mixed volume for volume with Freund's adjuvant (Sigma), prepared in the form of a water-in-oil emulsion and which is known to have a good immunogenic capacity. Three mice were immunized for each tumour marker. The mice received three successive doses of 10 µg of the immunogens at 0, 2 and 4 weeks. All the injections were given subcutaneously. The first injection is given as a mixture of complete Freund's adjuvant, the following two are given as a mixture with incomplete Freund's adjvant. Between D50 and D70 after the first injection, the humoral responses were restimulated with an intravenous injection of 100 µg of the recombinant protein. For Prodefensin-A6, two different series of immunizations were carried out. A first group of mice received the Prodefensin-A6 peptide (SEQ ID No.1) coupled to BSA and to KLH (in alternation according to injections). A second group of mice received the Prodefensin-A6 propeptide (SEQ ID No.2) coupled to BSA and to KLH (in alternation according to injections). Anti-Prodefensin-A6 antibodies were obtained from the animals belonging to each of the two groups.

3. Monitoring the Appearance of the Humoral Response

In order to monitor the appearance of the antibodies, blood samples were taken regularly from the mice. The presence of the anti-tumour marker antibodies is tested using an ELISA. The protein of interest is used for capture (1 µg/well); after saturation, various dilutions of the test sera are reacted with the antigen (incubation at 37° C., for 1 h). The specific antibodies present in the serum are revealed with an AffiniPure goat anti-mouse IgG antibody conjugated to alkaline phosphatase (H+ L, Jackson Immunoresearch, Cat No. 115-055-146), which binds to the antibodies being sought (0.1 µg/well).

4. Production of Monoclonal Antibodies

Three days after the final injection, for each tumour marker, one of the mice immunized was sacrificed; the blood and the spleen were removed. The splenocytes obtained from the spleen were cultured with Sp2/0-Ag14 myeloma cells in order for them to fuse and become immortalized, according to the protocol described by Köhler and Milstein[81,82]. After an incubation period of 12-14 days, the supernatants of the hydridomas obtained were screened in order to determine the presence of anti-tumour marker antibodies, using the ELISA assay described in point 3 of this example. When synthetic peptides coupled to BSA or KLH were used as immunogen, the clones directed against BSA and KLH were eliminated by carrying out an ELISA screening with uncoupled BSA or KLH for capture. The positive hybridoma colonies were subcloned twice according to the limiting dilution technique, which is well known to those skilled in the art.

5. Characterization of the Monoclonal Antibodies by Immunoblotting

The monoclonal antibodies directed against the aminoacylase-1, LEI, ezrin, I-plastin, Gal-3, calreticulin and LDH tumour markers are described in patent application to WO2009/024691.

The 1H8C9, 11B2D2, 13E7F3, 11E8C9, 6E1B4, 10C2G3, 12F3F2, 12F8E4 and 12H4E1 monoclonal antibodies are directed against Prodefensin-A6 and were obtained by carrying out the techniques described in points 1 to 4 of this example.

5.1. Methodology

The transfected 293T line cell culture extracts are prepared by directly lysing the cell pellet with 600 µl of PBS containing 0.5% Triton X-100 and protease inhibitors, and then treated according to the NuPAGE Novex gel sample preparation protocol (Invitrogen). To obtain the tissue extracts, tumour and mucosal biopsies of patient CLSP105 were dissociated with a scalpel, and were then subjected to ten cycles of extraction in the Medimachine system (Becton Dickinson) using 50 μm Medicons with 1 ml of PBS buffer containing 2.5 mM EDTA and protease inhibitors (Roche complete™ tablets). These 10 ml of cell suspension are pooled, made up to 25 ml, and then centrifuged for 15 mM at 600 g. The supernatant corresponds to the tissue extract which is treated according to the NuPAGE Novex gel sample preparation protocol. Reduced samples are used, at a final total protein concentration of 0.4 mg/ml. The deposit volume is 20 μl per well, on a NuPAGE Novex bis-tris 4-12% gel, with MES running buffer. After migration (at 200 V, for 1 hour), and transfer onto a PVDF membrane (at 400 mA, for 45 mM), the quality of the transfer is assessed by staining with amido black.

The membranes are saturated with 5% skimmed milk (Régilait) in a solution of TNT (15 mM Tris, 0.14 M NaCl, 0.5% Tween 20, pH 8) at ambient temperature for 1 hour. After saturation, the membranes are incubated for 1 hour with the various test antibodies diluted to 10 μg/ml in the saturating solution. After rinsing with TNT, the membranes are incubated for 1 hour at ambient temperature with an anti-mouse horseradish peroxidase conjugate diluted to 1:5000 (Cat No. 115-035-062, Jackson Immunoresearch) in the saturating solution. After rinsing, the developing is carried out with the Substrate Supersignal West Dura Extended kit (Cat No. 34076, Pierce) according to the recommended information for use. The exposure time was 2 minutes for the experiment presented in FIG. 1 and 100 seconds for the experiment presented in Table 1.

The chemiluminescence signal on the membranes was measured with the VersaDoc 5000 imaging system from Bio-Rad. Based on the image of the Western blot, the volumes of the bands which correspond to the various tumour markers were evaluated with the QuantityOne software (Bio-Rad). The volume corresponds to the intensity of the chemiluminescence signal multiplied by the surface area of the band.

5.2. Results

The Western blotting results reproduced in FIG. 1 and Table 1 give the volume of the bands corresponding to the tumour marker of interest for the Western blotting analyses, as a function of the various samples tested. The culture supernatant of 293Ts transfected with the pCMX-XL5-Prodefensin-A6 plasmid containing secreted Prodefensin-A6 and the Prodefensin-A6 peptide (7 ng per well) were used to evaluate the reactivity in Western blotting of the nine anti-Prodefensin-A6 antibodies (FIG. 1). All the antibodies recognize the Prodefensin-A6 peptide. All the antibodies, except for the monoclonal 11E8C9, recognize the Prodefensin-A6 secreted into the culture supernatant under the experimental conditions used. However, intensity of the signals obtained is very disparate, showing that not all the antibodies have the same reactivity. The results presented in Table 1 show that the tumour markers tested are well expressed in the tumour tissue obtained from the patients. Prodefensin-A6 is not expressed by the Caco-2 or HT-29 colon cell lines; for this reason, these lysates were not included in the analyses.

The intensity of the signal obtained with an antibody on a sample can be compared to the signals obtained with the other samples and the same antibody. The technique used makes it possible to confirm the presence or the absence of the marker in the tissue (non-remote sample) and the specificity of the antibodies with respect to the markers. This technique has not been used in this example in the remote samples because it would not make it possible to come to a conclusion regarding the presence or absence of the tumour marker in the remote samples, nor to determine whether the concentration of said tumour marker is increased or decreased in said samples. Furthermore, the experimental scheme used does not make it possible to compare the reactivity of one antibody with another.

TABLE 1

| Anti-ProDEFA6 antibody | 293T/ProDEFA6 culture supernatant | CLSP105 mucosal tissue | CLSP105 tumour tissue |
|---|---|---|---|
| 1H8C9 | 2475 | Negative | 457 |
| 11B2D2 | 556 | Negative | 140 |
| 13E7F3 | 134 | Negative | Negative |
| 11E8C9 | Negative | Negative | Negative |

6. Analysis of the Recognition of the Prodefensin-A6 Propeptide by the Monoclonal Antibodies by Dot-Blotting 6.1. Methodology The dot-blotting analysis was carried out using the Prodefensin-A6 peptide (SEQ ID No.1, concentration 0.1 mg/ml) and the Prodefensin-A6 propeptide (SEQ ID No.3, concentration 2.38 mg/ml). A drop of each sample was deposited in duplicate onto nitrocellulose membranes (Transblot transfer medium, Bio-rad) and then dried in the open air.

The immunodeveloping protocol is identical to that described in paragraph 5.1 of this example. The exposure time used for this experiment was 1 minute.

6.2. Results

All the antibodies tested recognize the Prodefensin-A6 peptide (SEQ ID No.1) in dot-blotting (FIG. 2). The most reactive antibody in this technique is the 10C2G3 clone. The 6E1B4, 12F3F2, 12F8E4 and 12H4E1 antibodies form a homogeneous group, less reactive than 10C2G3 but more reactive than the group 1H$_8$C9, 11B2D2, 13E7F3 and 11E8C9, which is more heterogeneous. Moreover, the reactivities in Western blotting and in dot-blotting do not always correlate: the 6E1B4, 12F3F2, 12F8E4 and 12H4E1 antibodies have a similar reactivity in dot-blotting, whereas the intensities of the signals obtained in Western blotting are different (FIGS. 1 and 2). The Western blotting was carried out under denaturing conditions, whereas the peptides are spotted directly without denaturation for the dot-blotting.

Only the 6E1B4, 10C2G3, 12F3F2, 12F8E4 and 12H4E1 antibodies recognize the Prodefensin-A6 propeptide (SEQ ID No.3) in dot-blotting. The 1H$_8$C9, 11B2D2, 13E7F3 and 11E8C9 antibodies do not show any significant reactivity with the Prodefensin-A6 propeptide (SEQ ID No.3), indicating that their epitope is located in the mature defensin-A6 part of the Prodefensin-A6 precursor. Among the five antibodies which react with the Prodefensin-A6 propeptide (SEQ ID No.3), the minimum epitope of which is therefore contained in this sequence, the 6E1B4, 10C2G3, 12F3F2 and 12F8E4 clones all exhibit the same reactivity profile: the ratio of the signals obtained (Prodefensin-A6 propeptide/Prodefensin-A6 peptide*100, FIG. 2) is between 29 and 31 for all these antibodies. The 12H4E1 clone differs from these other anti-Prodefensin-A6 propeptide antibodies because this ratio is 6. It recognizes the propeptide less well than the other four antibodies.

7. Analysis of the Recognition of the Prodefensin-A6 Propeptide by the Monoclonal Antibodies by Indirect ELISA 7.1. Methodology 96-Well plates (of the Nunc, Maxisorp type) were coated with the Prodefensin-A6 propeptide (SEQ ID No.3) diluted in PBS to 2 μg per well, overnight at ambient temperature. The plates are saturated with 10% milk in PBS-0.05% Tween 20 (PBS-T) for 1 h at 37° C. Three washes in PBS-T are carried out, 0.2 µg/well of the biotinylated test antibody, diluted in PBS-T containing 1% BSA, is deposited on the plates and incubation is carried out for 1 h at 37° C. After three PBS-T washes, streptavidin coupled to horseradish peroxidase (Jackson Immunoresearch Cat. No. 016-030-084, dilution 1/20 000 in PBS-T containing 1% BSA, 100 µl/well) is added. After incubation for 1 h at 37° C. and three PBS-T washes, the OPT EIA substrate (BD), 100 µl/well, is added. After 20 min, when the coloration develops, the reaction is stopped with 5 N sulphuric acid and the absorbance at 450 nm is measured. Results presented are the average of two measurements, the average background noise (0.02 optical density units) has not been subtracted.

7.2. Results

The results of the indirect ELISA assay are presented in FIG. 3. Under the experimental conditions used, only the four antibodies 6E1B4, 10C2G3, 12F3F2 and 12F8E4 bind to the Prodefensin-A6 propeptide adsorbed onto the solid phase. The other five antibodies, including 12H4E1, do not bind to the propeptide in this format. This experiment confirms the dot-blotting results (FIG. 2) and definitively establishes that, even though the 12H4E1 monoclonal antibody recognizes the Prodefensin-A6 propeptide, its reactivity is much less in comparison with the other four monoclonals 6E1B4, 10C2G3, 12F3F2 and 12F8E4.

8. Characterization of the Epitopes Recognized by the Monoclonal Antibodies using the Spotscan and Phage Display Peptide Library Screening Techniques 8.1. Methodology The Spotscan technique, adapted according to Frank and Döring[78], makes it possible to simultaneously synthesize a large number of peptides bound to a cellulose membrane. These peptides reproduce the sequence of the target antigen in the form of peptides of 8 to 12 amino acids, overlapping by 1 to 4 residues. These peptides are then brought into contact with the antibody to be studied in a colorimetric test of blot type, and the identification of the immunoreactive peptides makes it possible to deduce the minimum sequence of the antibody epitope and to locate it precisely on the antigen.

The synthesis is carried out on a cellulose membrane uniformly bearing polyethylene glycol (PEG) arms of 8 to 10 units in length, having a free $NH_2$ function at the chain end. It takes place from the C-terminal end to the N-terminal end of the peptides. The amino function of the amino acids is detected with an Fmoc (9-fluoromethyloxycarbonyl) group, and their side chains, capable of reacting during the synthesis, are also protected with trityl, t-butyl or t-butyl ether groups. The stock solutions of amino acids are prepared at a concentration of 0.33 M in MNP (N-methylpyrrolidone) containing 0.5 M of HOBt (hydroxybenzotriazole). The amino acids are deposited using the ASP 222 robot (Abimed, Langenfeld, Germany), controlled by means of the AutoSpot XL software. The use of this robot makes it possible to simultaneously produce up to four membranes of 96 spots. i.e. 384 peptides.

For one amino acid coupling cycle, the robot deposits 0.7 µl of the solution of extemporaneously activated amino acid (one volume of solution of 1.1 M diisopropylcarbodiimide diluted in NMP for three volumes of amino acid stock solution) onto the membranes. This depositing is repeated a second time, and then the membranes are rinsed in DMF (N,N-dimethylformamide). The $NH_2$ groups which have not reacted are then acetylated via 4 to 6 incubations for 10 minutes in a 10% solution of acetic anhydride in DMF, in order to prevent the appearance of abortive or truncated peptides. After three washes of 2 minutes in DMF, the Fmoc groups protecting the amino function of the amino acids are cleaved by incubation for 5 minutes in a 20% piperidine solution in DMF. After four washes in DMF, the spots are coloured using a 1% solution of bromophenol blue in DMF, and then the membrane is rinsed three times in methanol and dried in the open air before the subsequent coupling cycle.

This protocol is repeated for the addition of each new amino acid. After the coupling of the final amino acid, the peptides are acetylated in order to enable the blocking of all the free $NH_2$ groups, thus preventing the addition of another amino acid. The side chains of all the peptides are then deprotected by incubating the membranes in a trifluoroacetic acid/dichloromethane/triisobutylsilane (5:5:0.3) bath for 1 hour. The membranes are then rinsed four times in dichloromethane, three times in DMF and three times in methanol, before being dried in the open air and stored at −20° C. until the immunodeveloping.

In order to immunodevelop the spots with a monoclonal antibody, the membranes are first rinsed in methanol, and then washed in TBS (50 mM Tris-HCl, pH 8.0, 140 mM NaCl, 3 mM KCl), before being incubated overnight at ambient temperature in the saturating solution (casein-based 10× concentrated solution (Western Blocking reagent, Roche) diluted in TBS-0.05% Tween 20 (TBS-T) and containing 5% sucrose). After a wash for 10 minutes in TBS-T, the membranes are incubated for 1 h 30 mM at 37° C. with the monoclonal antibody diluted to 20 µg/ml in saturating solution. The membranes are then washed three times in TBS-T, and then incubated with the alkaline phosphatase-coupled anti-mouse conjugate (Jackson Immunoresearch), diluted to ½000th in saturating solution. After two washes for 10 minutes in TBS-T, and then two washes in CBS (10 mM citric acid, pH 7, 140 mM NaCl, 3 mM KCl), the developer, prepared extemporaneously (600 µM 5-bromo-4-chloro-3-indoyl phosphate, 720 µM thiazolyl blue tetrazolium bromide and 5 mM $MgCl_2$ in CBS), is brought into contact with the membrane for 30 to 45 minutes in the dark. The immunoreactive peptides appear in blue-violet. After three rinses in distilled water, the membranes are scanned and then stored in water until regeneration.

The regeneration makes it possible to remove the antibodies and the conjugates bound to the peptides, which thus makes it possible to carry out a further immunoreactivity test with respect to another antibody. The membranes undergo a series of washes, each of 10 minutes: one wash in distilled water, six washes in DMF, three washes in regenerating buffer A (8 M urea, 35 mM SDS (sodium dodecyl sulphate), 0.1% β-mercaptoethanol), three washes in regenerating buffer B (distilled water/ethanol/acetic acid 4:5:1), and then two washes in methanol. The membranes are then dried in the open air before being stored at −20° C.

The characterization of the epitopes by screening of phage display peptide libraries was carried out using the commercial PhD12 Phage Display Peptide Library Kit (Cat. No. E#8110S) from New England Biolabs, according to the instructions supplied with the kit, version 2.7 of the protocol dated November 2007.

8.2. Results

Table 2 reproduces the epitopes recognized by five anti-Prodefensin-A6 propeptide antibodies, the epitope of which was analysed by the Spotscan technique. All these antibodies recognize the same region of the Prodefensin-A6 precursor, located between amino acids 25 and 30 according to the numbering beginning at the initial methionine (epitope 1). On the other hand, the exact sequence recognized by the various monoclonals is not identical. Thus, the 10C2G3 clone recognizes a minimum sequence of two amino acids (DP), whereas the 12H4E1 and 6E1B4 clones require a minimum sequence of six amino acids (EDDPLQ) in order to bind. The results presented in FIGS. 2 and 3 show that it is the 10C2G3 clone which makes it possible to obtain the highest signal in dot blotting and indirect ELISA for the recognition of the Prodefensin-A6 peptides. Surprisingly, the 12H4E1 clone differs from the other antibodies directed against epitope 1 of Prodefensin-A6 (FIGS. 2 and 3), even though the minimum sequence recognized is identical with the 6E1B4 antibody. The 12H4E1 clone recognizes the EDDPLQ sequence (SEQ ID No.6) better in the context of the total precursor protein (SEQ ID No.1) than in the context of the Prodefensin-A6 propeptide (SEQ ID No.3).

TABLE 2

| Antibodies | Epitope No. | Sequence of the epitope$^a$ (SEQ ID No.) | |
|---|---|---|---|
| 10C2G3 | 1 | DP (27-28) | (SEQ ID No. 4) |
| 12F3F2 | 1 | DPL (27-29) | (SEQ ID No. 5) |
| 12F8E4 | 1 | DPL (27-29) | (SEQ ID No. 5) |
| 12H4E1 | 1 | EDDPLQ (25-30) | (SEQ ID No. 6) |
| 6E1B4 | 1 | EDDPLQ (25-30) | (SEQ ID No. 6) |

$^a$Amino acid sequence of the region for binding of Prodefensin-A6 to the antibody tested.
The numbers between parentheses correspond to the position of the epitope on the amino acid sequence of Prodefensin-A6, the numbering beginning at the initial methionine.

The epitopes recognized by the 1H8C9, 11B2C2, 13E7F3 and 11E8C9 antibodies could not be determined by the Spotscan technique, which indicates that they are not linear. The screening of the phage display peptide libraries made it possible to select 5, 3, 7 and 4 mimotopes (linear sequence mimicking an epitope) which react, respectively, with the 1H8C9, 11B2C2, 11E8C9 and 13E7F3 antibodies. The sequences of these mimotopes are given in FIG. 4. For each antibody, the sequences of the recognized or immunoreactive mimotopes were aligned in order to determine a concensus sequence, which is indicated in bold in FIG. 4, which represents the minimum sequence recognized by the antibody. It was not possible to find even one of these consensus sequences in the primary structure (or peptide sequence) of Prodefensin-A6. Thus, these consensus sequences correspond to residues dispersed over the primary structure of the protein but which share a proximity in its three-dimensional structure in order to form a conformational epitope.

9. Detection of the Prodefensin-A6 by Sandwich ELISA 9.1. Methodology

The Prodefensin-A6 was detected by sandwich immunoassay using, for example, the Vidas® ELISA automated system (bioMerieux). This type of test can also be carried out in a microplate, in an automated or manual manner. To do this, the ELISA assay was constructed using the reagents of the Vidas® HBs Ag Ultra kit (bioMerieux, Cat. No. 30315). The reagents were used as described in the corresponding information sheet (ref. 11728 D-FR-2005/05), with the following modifications:

1. Cones were sensitized with the nine capture antibodies to be tested, at a concentration of 10 µg/ml.
2. The content of the second well of the HBs Ag Ultra cartridge was replaced with 300 µl of revealing antibody to be tested (1H8C9 and 11E8C9) coupled to biotin, diluted to 1 µg/ml in the buffer (without goat serum) of the second well of the Vidas® HBs Ag Ultra kit.
3. The culture supernatant of 293Ts transfected with the pCMX-XL5-Prodefensin-A6 plasmid, containing secreted Prodefensin-A6, is added pure or diluted in PBS directly to the second well of the HBs Ag Ultra cartridge (50 µl).
4. The ELISA reaction was carried out using the Vidas® automated system and the HBs Ag Ultra protocol, of which the step of incubating the sample with the capture and revealing antibodies had been brought to 100 cycles.
5. The results were obtained in the form of crude values. The signal is in RFV, relative fluorescence value.

9.2. Results

Table 3 reproduces the reactivity of the various combinations of antibodies on a dilution to ½ of the culture supernatant of 293Ts transfected with the pCMX-XL5-Prodefensin-A6 plasmid and containing the native Prodefensin-A6 protein.

TABLE 3$^a$

| | Biotinylated detection antibody | |
|---|---|---|
| Capture antibody | 1H8C9 | 11E8C9 |
| 1H8C9 (epitope 2) | — | 43 |
| 11B2D2 (epitope 3) | 955* | 11 |
| 13E7F3 (epitope 5) | 1088* | 2881 |
| 11E8C9 (epitope 4) | 4015* | — |
| 6E1B4 (epitope 1) | 11646 | 3407 |
| 10C2G3 (epitope 1) | 11583 | 7420 |
| 12F3F2 (epitope 1) | 11481 | 6440 |
| 12F8E4 (epitope 1) | 11436 | 3064 |
| 12H4E1 (epitope 1) | 11868 | 11037 |

$^a$Signal in VIDAS sandwich immunoassay, in RFV (relative fluorescence unit).
*signal for supernatant assayed pure. The other supernatants were diluted to 1/2.

The results presented in Table 3 show that it is possible to detect Prodefensin-A6 using sandwich ELISAs based on various combinations of epitopes: for example, epitopes No. 5 and 4, epitopes No. 1 and 4, or else preferentially a combination of epitope 2 with any of the other epitopes identified (1, 3, 4, 5). Even more preferentially, epitope 2 is used for detection. On the other hand, the combination of epitopes No. 2 and 4 or else No. 3 and 4 do not make it possible to detect Prodefensin-A6.

A finer analysis of the reactivity of the antibodies directed against epitope 1, used for capture, and combined with the 1H8C9 clone, is presented in FIG. 5. The 12H4E1 clone is the best capture antibody, and in second position are the 10C2G3 and 12F3F2 clones. The lowest signals are obtained with the 6E1B4 and 12F8E4 antibodies. This result is very surprising since the 6E1B4 and 12H4E1 clones recognize the same minimum sequence.

Example 3

Serum Assays for the Tumour Markers

1. Patients and Specimens

Blood samples are collected from a network of eight clinical centres distributed throughout France, in the context of two Huriet-law protocols.

In order to obtain serum, the blood sample is taken on a dry tube. In order to obtain plasma, the blood sample is taken on an EDTA tube. After coagulation, the tube is centrifuged for 10 min at 1000 g, and the serum is removed, aliquoted and stored at −80° C. The tube of plasma is directly centrifuged for 10 min at 1000 g, and the plasma is removed, aliquoted and stored at −80° C. The samples are completely documented for the clinical history of the patients.

2. Serum Assay for the Prodefensin-A6 Tumour Marker

The Prodefensin-A6 precursor protein was assayed using the antibodies described in detail in example 2 and an ELISA assay using the Vidas® automated system (bioMérieux). To do this, the ELISA assay was constructed using the reagents of the Vidas® HBs Ag Ultra kit (bioMérieux, Cat. No. 30315). The reagents were used as described in the corresponding information sheet (ref. 11728 D-FR-2005/05), with the following modifications:

1. The cones were sensitized with the capture antibody 12H4E1 at a concentration of 15 μg/ml.

2. The content of the second well of the HBs Ag Ultra cartridge was replaced with 300 μl of the revealing antibody 1H8C9, coupled to biotin, diluted to 1 μg/ml in the buffer (without goat serum) of the second well of the Vidas® HBs Ag Ultra kit.

3. The serum or plasma samples (50 μL) were diluted directly in the second well of the HBs Ag Ultra cartridge.

4. The ELISA reaction was carried out using the Vidas® automated system and the HBs Ag Ultra protocol, of which the step of incubating the sample with the capture and revealing antibodies had been brought to 100 cycles.

5. The results were obtained in the form of crude values after subtraction of the background noise (reading of the substrate before reaction). A standard curve was established by assaying a range of concentrations of the synthetic Prodefensin-A6 peptide (SEQ ID No.1). The standard curve was plotted by reporting the concentration of the tumour marker along the x-axis and the signal read by Vidas® (RFV or Relative Fluorescence Value) along the y-axis. The concentration of tumour marker present in the body fluid to be assayed (blood, serum, plasma) was calculated by reporting the concentration corresponding to the RFV signal read by Vidas®.

The results of the serum Prodefensin-A6 assay in the patients by ELISA on a Vidas automated system are given in Table 4. The serum concentrations of Prodefensin-A6 are between 0 and 10 pg/ml in the patients having a colorectal adenocarcinoma (CRC+) and between 0 and 2 pg/ml in normal individuals (CRC−), which requires an extremely sensitive ELISA assay in order to be able to implement the invention in a biological fluid or remote sample. The only Prodefensin-A6 ELISA asssays which make it possible to achieve such a low limit of detection are based on the combination of antibodies which recognize epitopes 1 and 4. It is preferable to capture the Prodefensin-A6 via epitope 1. The combination which gives the most sensitive assay is that which was used here with the 12H4E1 antibody for capture and the 1H8C9 antibody for detection.

TABLE 4

| Pathological condition[a] | Patient identifier | Stage | TNM[b] | Age | Sex | Prodefensin-A6 (pg/mL) |
|---|---|---|---|---|---|---|
| IDD | CLSP046 | | | 43 | Male | 0.40 |
| IDD | CLSP049 | | | 30 | Female | 1.11 |
| IDD | CLSP051 | | | 47 | Female | 0.61 |
| IDD | CLSP056 | | | 23 | Female | 2.16 |
| IDD | CLSP065 | | | 41 | Female | 1.60 |
| IDD | CLSP084 | | | 34 | Female | 0.10 |
| IDD | CLSP134 | | | 59 | Male | 0.77 |
| IDD | CLSP135 | | | 47 | Female | 0.44 |
| IDD | CLSP137 | | | 35 | Female | 0.23 |
| IDD | CLSP151 | | | 55 | Male | 0.44 |
| IDD | CLSP152 | | | 36 | Male | 4.06 |
| CRC+ | CBSE011 | 0 | TisN0M0 | 76 | Male | 1.91 |
| CRC+ | CLSP059 | 0 | TisN0M0 | 72 | Male | 0.49 |
| CRC+ | CLSP104 | 0 | TisN0M0 | 48 | Male | 0.41 |
| CRC+ | CBSE001 | I | T1N0M0 | 69 | Female | 1.44 |
| CRC+ | CBSE016 | I | T1N0M0 | 74 | Male | 2.19 |
| CRC+ | CBSE022 | I | T1N0M0 | 78 | Male | 0.29 |
| CRC+ | CBSE025 | I | T2N0M0 | 81 | Female | 1.45 |
| CRC+ | CLSP047 | I | T1N0M0 | 76 | Female | 0.59 |
| CRC+ | CLSP062 | I | T2N0M0 | 83 | Male | 0.56 |
| CRC+ | CLSP067 | I | T2N0M0 | 61 | Male | 0.45 |
| CRC+ | CLSP080 | I | T2N0M0 | 74 | Female | 1.29 |
| CRC+ | CLSP085 | I | T2N0M0 | 74 | Female | 3.26 |
| CRC+ | CLSP086 | I | T2N0M0 | 61 | Male | 0.23 |
| CRC+ | CLSP093 | I | T2N0M0 | 71 | Male | 0.39 |
| CRC+ | CLSP100 | I | T3N0M0 | 53 | Male | 0.41 |
| CRC+ | CLSP118 | I | T2N0M0 | 60 | Female | 0.76 |
| CRC+ | CLSP145 | I | T1N0M0 | 71 | Male | 1.38 |
| CRC+ | CLSP146 | I | T2N0M0 | 55 | Female | 0.24 |
| CRC+ | CLSP150 | I | T2N0M0 | 61 | Male | 0.24 |
| CRC+ | CBSE004 | II | T3N0M0 | 85 | Male | 0.07 |
| CRC+ | CBSE017 | II | T3N0M0 | 74 | Male | 1.00 |
| CRC+ | CBSE018 | II | T4N0M0 | 82 | Male | 0.26 |
| CRC+ | CLSP043 | II | T3N0M0 | 75 | Male | 1.25 |
| CRC+ | CLSP060 | II | T4N0M0 | 84 | Male | 1.26 |
| CRC+ | CLSP069 | II | T3N0M0 | 46 | Male | 1.07 |
| CRC+ | CLSP075 | II | T3N0M0 | 65 | Male | 1.20 |
| CRC+ | CLSP087 | II | T3N0M0 | 75 | Male | 1.52 |
| CRC+ | CLSP088 | II | T3N0M0 | 88 | Female | 0.72 |
| CRC+ | CLSP096 | II | T3N0M0 | 79 | Female | 0.40 |
| CRC+ | CLSP105 | II | T3N0M0 | 73 | Male | 1.61 |
| CRC+ | CLSP107 | II | T3N0M0 | 79 | Male | 0.38 |
| CRC+ | CLSP110 | II | T3N0M0 | 67 | Female | 0.39 |
| CRC+ | CLSP113 | II | T3N0M0 | 50 | Male | 0.69 |
| CRC+ | CLSP115 | II | T3N0M0 | 65 | Female | 3.62 |
| CRC+ | CLSP117 | II | T3N0M0 | 78 | Female | 1.62 |
| CRC+ | CLSP119 | II | T3N0M0 | 78 | Male | 0.80 |
| CRC+ | CLSP122 | II | T3N0MX | 54 | Male | 0.81 |
| CRC+ | CLSP133 | II | T3N0M0 | 78 | Female | 0.83 |
| CRC+ | CLSP136 | II | T3N0M0 | 67 | Female | 0.22 |
| CRC+ | CLSP143 | II | T3N0M0 | 76 | Female | 1.25 |
| CRC+ | CLSP147 | II | T3N0M0 | 83 | Male | 0.77 |
| CRC+ | CLSP154 | II | T3N0M0 | 76 | Female | 0.86 |
| CRC+ | CLSP157 | II | T3N0 | 45 | Female | 0.42 |
| CRC+ | GHBD020 | II | T3N0M0 | 75 | Male | 1.01 |
| CRC+ | GHBD023 | II | T3N0M0 | 57 | Male | 0.23 |
| CRC+ | GHBD025 | II | T3N0M0 | 73 | Male | 0.73 |
| CRC+ | GHBD029 | II | T3N0M0 | 75 | Female | 2.22 |
| CRC+ | CBSE005 | III | T3N1M0 | 73 | Male | 4.27 |
| CRC+ | CBSE006 | III | T3N1M0 | 84 | Male | 9.24 |
| CRC+ | CBSE007 | III | T3N1M0 | 77 | Female | 2.02 |
| CRC+ | CBSE010 | III | T4N2M0 | 67 | Male | 9.17 |
| CRC+ | CBSE013 | III | T3N1M0 | 82 | Male | 4.50 |
| CRC+ | CBSE023 | III | T4N2M0 | 76 | Male | 2.04 |
| CRC+ | CLSP044 | III | T3N1M0 | 80 | Male | 0.47 |
| CRC+ | CLSP050 | III | T2N1M0 | 88 | Female | 2.18 |
| CRC+ | CLSP072 | III | T3N1M0 | 79 | Male | 2.17 |
| CRC+ | CLSP073 | III | T2N1M0 | 77 | Male | 1.59 |
| CRC+ | CLSP074 | III | T3N2M0 | 79 | Female | 0.64 |
| CRC+ | CLSP089 | III | T4N2M0 | 84 | Female | 0.81 |
| CRC+ | CLSP090 | III | T1N1M0 | 65 | Female | 1.47 |
| CRC+ | CLSP091 | III | T3N1M0 | 55 | Male | 0.29 |
| CRC+ | CLSP094 | III | T3N1M0 | 72 | Male | 0.47 |
| CRC+ | CLSP097 | III | T3N1M0 | 71 | Female | 0.74 |
| CRC+ | CLSP098 | III | T3N2M0 | 61 | Male | 0.69 |
| CRC+ | CLSP103 | III | T2N1MX | 60 | Male | 0.40 |
| CRC+ | CLSP106 | III | T4N2M0 | 85 | Female | 1.90 |
| CRC+ | CLSP121 | III | T3N2M0 | 76 | Male | 0.49 |
| CRC+ | CLSP123 | III | T4N1MX | 68 | Male | 1.81 |
| CRC+ | CLSP138 | III | T3N1MX | 78 | Male | 1.03 |
| CRC+ | CLSP141 | III | T3N1M0 | 70 | Male | 1.21 |
| CRC+ | CLSP144 | III | T3N1M0 | 52 | Female | 0.93 |
| CRC+ | CLSP153 | III | T3N2MX | 85 | Male | 5.09 |
| CRC+ | GHBD019 | III | T3N1M0 | 74 | Male | 0.92 |
| CRC+ | CBSE012 | IV | T4N3M1 | 37 | Female | 0.50 |
| CRC+ | CBSE019 | IV | T3N2M1 | 58 | Male | 1.52 |
| CRC+ | CBSE026 | IV | T4N1M1 | 72 | Male | 0.61 |

TABLE 4-continued

| Pathological condition[a] | Patient identifier | Stage | TNM[b] | Age | Sex | Pro-defensin-A6 (pg/mL) |
|---|---|---|---|---|---|---|
| CRC+ | CBSE027 | IV | T4N2M1 | 78 | Female | 1.04 |
| CRC+ | CLSP042 | IV | T3N2M1 | 56 | Male | 1.39 |
| CRC+ | CLSP057 | IV | T3N2M1 | 61 | Female | 0.27 |
| CRC+ | CLSP068 | IV | TXNXM1 | 60 | Female | 1.29 |
| CRC+ | CLSP079 | IV | T3N0M1 | 81 | Female | 0.81 |
| CRC+ | CLSP083 | IV | T3N1M1 | 67 | Female | 0.79 |
| CRC+ | CLSP095 | IV | T3N1M1 | 64 | Male | 0.65 |
| CRC+ | CLSP109 | IV | T3N1M1 | 60 | Male | 0.88 |
| CRC+ | CLSP132 | IV | T3N1M1 | 62 | Female | 2.80 |
| CRC+ | CLSP156 | IV | T4N0M1 | 59 | Male | 1.25 |
| CRC+ | CLSP159 | IV | T3N0M1 | 68 | Female | 0.89 |
| CRC+ | CLSP160 | IV | TXNXM1 | 70 | Male | 2.77 |
| CRC+ | CLSP161 | IV | T3N2M1 | 78 | Female | 0.64 |
| Adenoma | CLSP055 | | | 73 | Male | 0.55 |
| Adenoma | CLSP058 | | | 55 | Female | 0.58 |
| Adenoma | CLSP061 | | | 61 | Female | 0.62 |
| Adenoma | CLSP099 | | T0N0M0 | 62 | Male | 0.13 |
| Adenoma | CLSP116 | | | 63 | Male | 0.66 |
| Adenoma | CLSP120 | | | 56 | Female | 0.30 |
| Adenoma | CLSP142 | | T0 | 21 | Male | 1.77 |
| Adenoma | CLSP148 | | TisN0M0 | 50 | Male | 1.07 |
| Adenoma | CLSP149 | | T1N0M0 | 50 | Female | 1.69 |
| CRC− | N00656 | | | 47 | Female | 0.22 |
| CRC− | N006615 | | | 43 | Female | 0.45 |
| CRC− | N00664- | | | 44 | Male | 0.13 |
| CRC− | N006658 | | | 48 | Male | 0.46 |
| CRC− | N009901 | | | 52 | Male | 0.65 |
| CRC− | N011147 | | | 50 | Male | 0.87 |
| CRC− | N011155 | | | 51 | Male | 0.61 |
| CRC− | N011243 | | | 52 | Male | 0.33 |
| CRC− | N017218 | | | 44 | Female | 0.49 |
| CRC− | N017234 | | | 37 | Male | 0.47 |
| CRC− | N017250 | | | 48 | Female | 0.48 |
| CRC− | N017269 | | | 40 | Male | 0.82 |
| CRC− | N017365 | | | 44 | Female | 0.54 |
| CRC− | N017402 | | | 25 | Male | 0.65 |
| CRC− | N017410 | | | 37 | Male | 0.53 |
| CRC− | N018552 | | | 42 | Male | 0.33 |
| CRC− | N041082 | | | 58 | Male | 1.16 |
| CRC− | N041138 | | | 58 | Male | 0.97 |
| CRC− | N044703 | | | 54 | Male | 0.37 |
| CRC− | N045730 | | | 50 | Male | 0.57 |
| CRC− | N14397- | | | 58 | Male | 0.71 |
| CRC− | N143988 | | | 62 | Male | 0.49 |
| CRC− | N144358 | | | 61 | Female | 0.67 |
| CRC− | N146601 | | | 57 | Male | 0.81 |
| CRC− | N14661- | | | 61 | Female | 1.14 |
| CRC− | N146695 | | | 52 | Male | 0.91 |
| CRC− | N14813- | | | 57 | Male | 0.72 |
| CRC− | N148279 | | | 55 | Male | 1.04 |
| CRC− | N148340 | | | 51 | Male | 1.05 |
| CRC− | N314164 | | | 48 | Male | 1.00 |
| CRC− | N318050 | | | 56 | Male | 0.64 |
| CRC− | N318077 | | | 56 | Male | 1.02 |
| CRC− | N318368 | | | 60 | Male | 0.50 |
| CRC− | N318384 | | | 58 | Female | 0.69 |
| CRC− | N318421 | | | 60 | Female | 0.64 |
| CRC− | N325015 | | | 42 | Male | 0.44 |
| CRC− | N329630 | | | 59 | Male | 0.39 |
| CRC− | N370529 | | | 57 | Male | 0.40 |
| CRC− | N376461 | | | 58 | Male | 0.26 |
| CRC− | N376488 | | | 63 | Female | 0.22 |
| CRC− | N37663- | | | 62 | Male | 0.40 |
| CRC− | N376760 | | | 58 | Female | 0.57 |
| CRC− | N376912 | | | 64 | Female | 0.57 |
| CRC− | N418599 | | | 56 | Female | 0.23 |
| CRC− | N418687 | | | 28 | Female | 0.19 |
| CRC− | N418716 | | | 53 | Female | 0.65 |
| CRC− | N418740 | | | 54 | Male | 0.75 |
| CRC− | N418759 | | | 49 | Female | 0.84 |
| CRC− | N418804 | | | 54 | Female | 0.24 |
| CRC− | N440216 | | | 60 | Female | 0.40 |
| CRC− | N440478 | | | 60 | Female | 0.49 |
| CRC− | N440507 | | | 64 | Male | 1.02 |
| CRC− | N469775 | | | 36 | Male | 0.47 |
| CRC− | N491028 | | | 50 | Male | 0.59 |
| CRC− | N491191 | | | 52 | Female | 1.16 |
| CRC− | N491247 | | | 58 | Male | 0.35 |
| CRC− | N491386 | | | 58 | Male | 0.71 |
| CRC− | N491685 | | | 56 | Male | 0.52 |
| CRC− | N511463 | | | 52 | Female | 0.46 |
| CRC− | N511471 | | | 59 | Female | 0.68 |
| CRC− | N511498 | | | 55 | Female | 0.58 |
| CRC− | N518059 | | | 0 | Male | 0.69 |
| CRC− | N518518 | | | 58 | Female | 0.78 |
| CRC− | N518542 | | | 60 | Male | 0.81 |
| CRC− | N519086 | | | 59 | Male | 0.80 |
| CRC− | N527135 | | | 56 | Female | 0.39 |
| CRC− | N527450 | | | 56 | Female | 0.38 |
| CRC− | N557699 | | | 55 | Male | 1.40 |
| CRC− | N557701 | | | 57 | Male | 1.66 |
| CRC− | N557736 | | | 56 | Male | 0.41 |
| CRC− | N557760 | | | 60 | Male | 1.68 |
| CRC− | N593116 | | | 52 | Female | 0.29 |
| CRC− | N593167 | | | 53 | Male | 1.12 |
| CRC− | N593183 | | | 52 | Female | 0.25 |
| CRC− | N593255 | | | 51 | Male | 1.88 |
| CRC− | N593351 | | | 57 | Male | 1.34 |
| CRC− | N744056 | | | 51 | Male | 0.61 |
| CRC− | N748022 | | | 50 | Female | 0.33 |
| CRC− | N835966 | | | 45 | Male | 0.62 |
| CRC− | N836299 | | | 52 | Female | 1.13 |
| CRC− | N857704 | | | 52 | Female | 0.29 |
| CRC− | N858037 | | | 63 | Female | 1.15 |
| CRC− | N858248 | | | 62 | Male | 1.72 |
| CRC− | N862239 | | | 53 | Male | 0.24 |
| CRC− | N862298 | | | 63 | Male | 0.42 |
| CRC− | N862300 | | | 51 | Male | 1.81 |

[a]IDD = Inflammatory bowel diseases (Crohn's disease and Ulcerative colitis)
CRC+ = patients having colorectal cancer (adenocarcinoma),
CCR− = healthy individuals.
[b]TNM: stage of tissue invasion (T), lymph node invasion (N) and remote invasion (metastases, M)

The doses obtained for the patients analysed are reported in FIG. 6. It may be noted, in this figure and in Table 4, that 2, 2, 10 and 2 patients having respectively stage I, II, III or IV colorectal cancer show a clear increase in their amount of serum Prodefensin-A6, strictly above the highest value observed in the group of healthy individuals (1.88 pg/ml). In the adenoma group, no amount observed exceeds this value, while in the IDD group, there are 2.

Example 4

Use of the Serum Assays for the Tumour Markers in Combination

The applicant showed in example 3 that abnormally elevated amounts of Prodefensin-A6 precursor protein could be observed in the bloodstream of certain patients having colorectal cancer. Furthermore, the applicant showed in patent applications WO2009/024691, WO2009019365, WO2009019368, WO2009019369, WO2009019366, WO2009019370 and WO2009019367 that abnormally elevated or abnormally reduced amounts of other tumour markers, such as LEI, ezrin, aminoacylase-1, L-FABP, Apo A1, Apo A2, 1-plastin, beta2-microglobulin, CEA, CA19-9, testosterone, galectin-3, LDH-B, proteasome 20S, E-cadherin or regenerating islet-derived protein 3 alpha, otherwise known as pancreatitis associated protein (PAP1), could also be observed in the bloodstream of certain patients having colorectal cancer. The methods for assaying these tumour markers were described in the abovementioned patent applications. The method for assaying MIF was carried out with the human MIF Quantikine ELISA kit from R&D Systems (Cat No. DMF00) according to the producer's instructions.

Surprisingly, the increase or the decrease in the amount, in the blood, of two given markers is not systematically observed in the same patients. As a result, the combination of several tumour markers makes it possible to increase the number of patients identified as having colorectal cancer. Thus, a patient A may present an increse or a decrease in one or more tumour markers (group X), it being possible for said markers of group X to be normal in a patient B; in this same patient B, one or more other tumour markers (group Y) may be elevated or reduced, it being possible for said markers of group Y to be normal in patient A.

The various tumour markers assayed by the applicant may thus be combined by means of various mathematical algorithms well known to those skilled in the art. By way of illustration, and without this example being exhaustive in nature, the following method was carried out:

1. A threshold value was set for each tumour marker.
2. When the amount of the tumour marker in the blood was increased in the case of colorectal cancer, the amount in the blood, obtained for a given patient, was divided by its threshold value. When the amount of the tumour marker in the blood was decreased in the case of colorectal cancer, the amount in the blood, obtained for a given patient, was inverted and then multiplied by its threshold value.
3. When the "amount in the blood divided by threshold value" ratio was greater than 1, the ratio was multiplied by a coefficient, for example 10. The value thus obtained was named the "score", for the patient studied, for the tumour marker under consideration.
4. The scores obtained for various tumour markers were added, with them being weighted by a factor specific to each marker. In the case of the example below, all the weighting factors were set at 1.
5. The sum of the scores was divided by the total number of scores added and the value thus obtained was named the "total score".
6. The patient is diagnosed as having colorectal cancer when the total score of said patient is increased relative to a threshold score.

The total scores for a selection of 2, 3, 4, 5, 7 and 8 markers comprising Prodefensin-A6 are given in Table 5.

The combination of the Prodefensin-A6 and CEA tumour markers thus makes it possible to obtain, for the same group of 78 patients, increased total scores "$2^a$" in 41 patients having a colorectal adenocarcinoma, whereas assaying Prodefensin-A6 and CEA alone showed an increase, respectively, in 17 and 28 patients only.

The combination of the Prodefensin-A6 and CA19-9 tumour markers thus makes it possible to obtain, for the same group of 78 patients, increased total scores "$2^b$" in 28 patients having a colorectal adenocarcinoma, whereas assaying Prodefensin-A6 and CA19-9 alone showed an increase, respectively, in 17 and 15 patients only.

The combination of the Prodefensin-A6 and beta2-microglobulin tumour markers thus makes it possible to obtain, for the same group of 78 patients, increased total scores "$2^c$" in 49 patients having a colorectal adenocarcinoma, whereas assaying Prodefensin-A6 and beta2-microglobulin alone showed an increase, respectively, in 17 and 43 patients only.

The combination of the Prodefensin-A6 and L-FABP tumour markers thus makes it possible to obtain, for the same group of 78 patients, increased total scores "$2^d$" in 41 patients having a colorectal adenocarcinoma, whereas assaying Prodefensin-A6 and L-FABP alone showed an increase, respectively, in 17 and 35 patients only.

The combination of the Prodefensin-A6, CA19-9 and CEA tumour markers thus makes it possible to obtain, for the same group of 78 patients, increased total scores "$3^e$" in 46 patients having a colorectal adenocarcinoma, whereas assaying Prodefensin-A6, CA19-9 and CEA alone showed an increase, respectively, in 17, 15 and 28 patients only.

The combination of the Prodefensin-A6, beta2-microglobulin and CEA tumour markers thus makes it possible to obtain, for the same group of 78 patients, increased total scores "$3^f$" in 60 patients having a colorectal adenocarcinoma, whereas assaying Prodefensin-A6, beta2-microglobulin and CEA alone showed an increase, respectively, in 17, 43 and 28 patients only.

The combination of the Prodefensin-A6, beta2-microglobulin, CA19-9 and CEA tumour markers thus makes it possible to obtain, for the same group of 78 patients, increased total scores "$4^g$" in 63 patients having a colorectal adenocarcinoma, whereas assaying Prodefensin-A6, beta2-microglobulin, CA19-9 and CEA alone showed an increase, respectively, in 17, 43, 15 and 28 patients only.

The combination of the Prodefensin-A6, beta2-microglobulin, L-FABP and CEA tumour markers thus makes it possible to obtain, for the same group of 78 patients, increased total scores "$4^h$" in 69 patients having a colorectal adenocarcinoma, whereas asssaying Prodefensin-A6, beta2-microglobulin, L-FABP and CEA alone showed an increase, respectively, in 17, 43, 35 and 28 patients only.

The combination of the Prodefensin-A6, CA19-9, L-FABP and CEA tumour markers thus makes it possible to obtain, for the same group of 78 patients, increased total scores "$4^i$" in 59 patients having a colorectal adenocarcinoma, whereas asssaying Prodefensin-A6, CA19-9, L-FABP and CEA alone showed an increase, respectively, in 17, 15, 35 and 28 patients only.

The combination of the Prodefensin-A6, beta2-microglobulin, CA19-9, L-FABP and CEA tumour markers thus makes it possible to obtain, for the same group of 78 patients, increased total scores "$5^j$" in 71 patients having a colorectal adenocarcinoma, whereas assaying Prodefensin-A6, beta2-microglobulin, CA19-9, L-FABP and CEA alone showed an increased, respectively, in 17, 43, 15, 35 and 28 patients only.

The combination of the Prodefensin-A6, beta2-microglobulin, CA19-9, galectin-3, L-FABP, MIF and CEA tumour markers thus makes it possible to obtain, for the same group of 78 patients, increased total scores "$7^k$" in 74 patients having a colorectal adenocarcinoma, whereas assaying Prodefensin-A6, beta2-microglobulin, CA19-9, galectin-3, L-FABP, MIF and CEA alone showed an increase, respectively, in 17, 43, 15, 13, 35, 23 and 28 patients only.

The combination of the Prodefensin-A6, beta2-microglobulin, CA19-9, galectin-3, L-FABP, MIF, I-plastin and CEA tumour markers thus makes it possible to obtain, for the same group of 78 patients, increased total scores "$8^l$" in 75 patients having a colorectal adenocarcinoma, whereas assaying Prodefensin-A6, beta2-microglobulin, CA19-9, galectin-3, L-FABP, MIF, I-plastin and CEA alone showed an increase, respectively, in 17, 43, 15, 13, 35, 23, 3 and 28 patients only.

TABLE 5

| Pathological condition | Patient identifier | Score 2[a] | Score 2[b] | Score 2[c] | Score 2[d] | Score 3[e] | Score 3[f] | Score 4[g] | Score 4[h] | Score 4[i] | Score 5[j] | Score 7[k] | Score 8[l] |
|---|---|---|---|---|---|---|---|---|---|---|---|---|---|
| CRC− | N011155 | 0.32 | 0.32 | 0.32 | 0.32 | 0.32 | 0.32 | 0.32 | 0.32 | 0.32 | 0.32 | 0.32 | 0.32 |
| CRC− | N011243 | 0.18 | 0.18 | 0.18 | 0.14 | 0.18 | 0.18 | 0.18 | 0.14 | 0.14 | 0.14 | 0.14 | 0.14 |
| CRC− | N14661- | 0.61 | 0.61 | 0.61 | 0.39 | 0.61 | 0.61 | 0.61 | 0.39 | 0.39 | 0.39 | 0.39 | 0.39 |
| CRC− | N044703 | 0.20 | 0.20 | 0.20 | 0.21 | 0.20 | 0.20 | 0.20 | 0.21 | 0.21 | 0.21 | 0.21 | 0.21 |
| CRC− | N318050 | 0.34 | 0.34 | 0.34 | 0.31 | 0.34 | 0.34 | 0.34 | 0.31 | 0.31 | 0.31 | 0.31 | 0.31 |
| CRC− | N418599 | 0.12 | 0.12 | 0.12 | 0.23 | 0.12 | 0.12 | 0.12 | 0.23 | 0.23 | 0.23 | 0.23 | 0.23 |
| CRC− | N017410 | 0.28 | 0.28 | 0.28 | 0.27 | 0.28 | 0.28 | 0.28 | 0.27 | 0.27 | 0.27 | 0.27 | 0.27 |
| CRC− | N329630 | 0.21 | 0.21 | 0.21 | 0.33 | 0.21 | 0.21 | 0.21 | 0.33 | 0.33 | 0.33 | 0.33 | 0.33 |
| CRC− | N045730 | 0.30 | 0.30 | 0.30 | 0.32 | 0.30 | 0.30 | 0.30 | 0.32 | 0.32 | 0.32 | 0.32 | 0.32 |
| CRC− | N593116 | 0.15 | 0.15 | 0.15 | 0.27 | 0.15 | 0.15 | 0.15 | 0.27 | 0.27 | 0.27 | 0.27 | 0.27 |
| CRC− | N018552 | 0.18 | 0.18 | 0.18 | 0.27 | 0.18 | 0.18 | 0.18 | 0.27 | 0.27 | 0.27 | 0.27 | 0.27 |
| CRC− | N017218 | 0.26 | 0.26 | 0.26 | 0.38 | 0.26 | 0.26 | 0.26 | 0.38 | 0.38 | 0.38 | 0.38 | 0.38 |
| CRC− | N011147 | 0.46 | 0.46 | 0.46 | 0.43 | 0.46 | 0.46 | 0.46 | 0.43 | 0.43 | 0.43 | 0.43 | 0.43 |
| CRC− | N017365 | 0.29 | 0.29 | 0.29 | 0.33 | 0.29 | 0.29 | 0.29 | 0.33 | 0.33 | 0.33 | 0.33 | 0.33 |
| CRC− | N440216 | 0.21 | 0.21 | 0.21 | 0.33 | 0.21 | 0.21 | 0.21 | 0.33 | 0.33 | 0.33 | 0.33 | 0.33 |
| CRC− | N376912 | 0.30 | 0.30 | 0.30 | 0.38 | 0.30 | 0.30 | 0.30 | 0.38 | 0.38 | 0.38 | 0.38 | 0.38 |
| CRC− | N527450 | 0.20 | 0.20 | 0.20 | 0.34 | 0.20 | 0.20 | 0.20 | 0.34 | 0.34 | 0.34 | 0.34 | 0.34 |
| CRC− | N748022 | 0.18 | 0.18 | 0.18 | 0.26 | 0.18 | 0.18 | 0.18 | 0.26 | 0.26 | 0.26 | 0.26 | 0.26 |
| CRC− | N593183 | 0.13 | 0.13 | 0.13 | 0.32 | 0.13 | 0.13 | 0.13 | 0.32 | 0.32 | 0.32 | 0.32 | 0.32 |
| CRC− | N009901 | 0.35 | 0.35 | 0.35 | 0.46 | 0.35 | 0.35 | 0.35 | 0.46 | 0.46 | 0.46 | 0.46 | 0.46 |
| CRC− | N017269 | 0.44 | 0.44 | 0.44 | 0.49 | 0.44 | 0.44 | 0.44 | 0.49 | 0.49 | 0.49 | 0.49 | 0.49 |
| CRC− | N376461 | 0.14 | 0.14 | 0.14 | 0.37 | 0.14 | 0.14 | 0.14 | 0.37 | 0.37 | 0.37 | 0.37 | 0.37 |
| CRC− | N862300 | 0.96 | 0.96 | 0.96 | 0.77 | 0.96 | 0.96 | 0.96 | 0.77 | 0.77 | 0.77 | 0.77 | 0.77 |
| CRC− | N376488 | 0.12 | 0.12 | 0.12 | 0.42 | 0.12 | 0.12 | 0.12 | 0.42 | 0.42 | 0.42 | 0.42 | 0.42 |
| CRC− | N017234 | 0.25 | 0.25 | 0.25 | 0.47 | 0.25 | 0.25 | 0.25 | 0.47 | 0.47 | 0.47 | 0.47 | 0.47 |
| CRC− | N527135 | 0.21 | 0.21 | 0.21 | 0.44 | 0.21 | 0.21 | 0.21 | 0.44 | 0.44 | 0.44 | 0.44 | 0.44 |
| CRC− | N440478 | 0.26 | 0.26 | 0.26 | 0.44 | 0.26 | 0.26 | 0.26 | 0.44 | 0.44 | 0.44 | 0.44 | 0.44 |
| CRC− | N017402 | 0.35 | 0.35 | 0.35 | 0.56 | 0.35 | 0.35 | 0.35 | 0.56 | 0.56 | 0.56 | 0.56 | 0.56 |
| CRC− | N491191 | 0.62 | 0.62 | 0.60 | 0.62 | 0.62 | 0.60 | 0.60 | 0.60 | 0.62 | 0.60 | 0.55 | 0.55 |
| CRC− | N835966 | 0.33 | 0.33 | 0.56 | 0.25 | 0.33 | 0.56 | 0.56 | 0.43 | 0.25 | 0.43 | 0.45 | 0.45 |
| CRC− | N017250 | 0.21 | 0.22 | 0.26 | 0.29 | 0.20 | 0.21 | 0.20 | 0.25 | 0.23 | 0.23 | 0.23 | 0.23 |
| CRC− | N144358 | 0.36 | 0.36 | 0.49 | 0.28 | 0.36 | 0.49 | 0.49 | 0.39 | 0.28 | 0.39 | 0.40 | 0.40 |
| CRC− | N143988 | 0.26 | 0.26 | 0.51 | 0.33 | 0.26 | 0.51 | 0.51 | 0.47 | 0.33 | 0.47 | 0.48 | 0.48 |
| CRC− | N511498 | 0.30 | 0.23 | 0.51 | 0.35 | 0.25 | 0.44 | 0.37 | 0.43 | 0.29 | 0.37 | 0.34 | 0.33 |
| CRC− | N318384 | 0.44 | 0.19 | 0.49 | 0.31 | 0.30 | 0.50 | 0.38 | 0.44 | 0.29 | 0.35 | 0.37 | 0.33 |
| CRC− | N148340 | 0.32 | 0.33 | 0.62 | 0.54 | 0.24 | 0.44 | 0.35 | 0.46 | 0.32 | 0.39 | 0.42 | 0.39 |
| CRC− | N491386 | 0.20 | 0.20 | 0.48 | 0.44 | 0.14 | 0.32 | 0.25 | 0.37 | 0.23 | 0.30 | 0.33 | 0.29 |
| CRC− | N518518 | 0.49 | 0.29 | 0.59 | 0.48 | 0.38 | 0.59 | 0.48 | 0.57 | 0.42 | 0.49 | 0.44 | 0.39 |
| CRC− | N518542 | 0.32 | 0.22 | 0.57 | 0.22 | 0.22 | 0.45 | 0.34 | 0.34 | 0.16 | 0.27 | 0.28 | 0.29 |
| CRC− | N858248 | 0.61 | 0.63 | 0.87 | 0.72 | 0.52 | 0.68 | 0.60 | 0.65 | 0.53 | 0.59 | 0.55 | 0.48 |
| CRC− | N491247 | 0.35 | 0.19 | 0.42 | 0.35 | 0.30 | 0.46 | 0.39 | 0.47 | 0.36 | 0.42 | 0.43 | 0.39 |
| CRC− | N148279 | 0.38 | 0.35 | 0.70 | 0.46 | 0.30 | 0.53 | 0.44 | 0.49 | 0.32 | 0.42 | 0.44 | 0.40 |
| CRC− | N418687 | 0.26 | 0.06 | 0.45 | 0.23 | 0.18 | 0.44 | 0.33 | 0.42 | 0.22 | 0.34 | 0.41 | 0.36 |
| CRC− | N857704 | 0.22 | 0.33 | 0.44 | 0.22 | 0.32 | 0.39 | 0.42 | 0.37 | 0.31 | 0.39 | 0.46 | 0.41 |
| CRC− | N593255 | 0.65 | 0.54 | 0.97 | 0.72 | 0.46 | 0.74 | 0.58 | 0.67 | 0.45 | 0.55 | 0.50 | 0.43 |
| CRC− | N862298 | 0.37 | 0.15 | 0.22 | 0.22 | 0.27 | 0.37 | 0.27 | 0.37 | 0.27 | 0.27 | 0.41 | 0.33 |
| CRC− | N318421 | 0.58 | 0.21 | 0.67 | 0.47 | 0.41 | 0.72 | 0.56 | 0.69 | 0.46 | 0.57 | 0.56 | 0.49 |
| CRC− | N511471 | 0.29 | 0.21 | 0.53 | 0.47 | 0.22 | 0.43 | 0.33 | 0.46 | 0.31 | 0.38 | 0.38 | 0.36 |
| CRC− | N325015 | 0.40 | 0.48 | 0.50 | 0.33 | 0.51 | 0.52 | 0.58 | 0.50 | 0.49 | 0.55 | 0.54 | 0.47 |
| CRC− | N146695 | 0.27 | 0.30 | 0.54 | 0.46 | 0.22 | 0.38 | 0.32 | 0.39 | 0.27 | 0.34 | 0.36 | 0.32 |
| CRC− | N318077 | 0.47 | 0.32 | 0.64 | 0.59 | 0.35 | 0.56 | 0.44 | 0.58 | 0.42 | 0.48 | 0.51 | 0.46 |
| CRC− | N858037 | 0.40 | 0.32 | 0.71 | 0.50 | 0.28 | 0.53 | 0.41 | 0.49 | 0.30 | 0.40 | 0.47 | 0.42 |
| CRC− | N511463 | 0.16 | 0.20 | 0.46 | 0.29 | 0.16 | 0.33 | 0.29 | 0.34 | 0.20 | 0.30 | 0.43 | 0.40 |
| CRC− | N593167 | 0.45 | 0.62 | 0.59 | 0.47 | 0.51 | 0.49 | 0.53 | 0.46 | 0.47 | 0.50 | 0.50 | 0.55 |
| CRC− | N557736 | 0.57 | 0.14 | 0.41 | 0.23 | 0.40 | 0.58 | 0.45 | 0.50 | 0.36 | 0.41 | 0.41 | 0.39 |
| CRC− | N314164 | 0.36 | 0.46 | 0.58 | 0.56 | 0.37 | 0.45 | 0.43 | 0.48 | 0.42 | 0.46 | 0.54 | 0.47 |
| CRC− | N862239 | 0.31 | 0.29 | 0.44 | 0.24 | 0.36 | 0.46 | 0.46 | 0.43 | 0.36 | 0.44 | 0.46 | 0.40 |
| CRC− | N491685 | 0.26 | 0.17 | 0.64 | 0.42 | 0.20 | 0.51 | 0.40 | 0.52 | 0.29 | 0.43 | 0.49 | 0.44 |
| CRC− | N518059 | 0.27 | 0.22 | 0.55 | 0.58 | 0.20 | 0.42 | 0.34 | 0.52 | 0.35 | 0.43 | 0.47 | 0.48 |
| CRC− | N519086 | 0.31 | 0.32 | 0.56 | 0.52 | 0.28 | 0.44 | 0.38 | 0.48 | 0.36 | 0.43 | 0.43 | 0.45 |
| CRC− | N37663- | 0.33 | 0.61 | 0.55 | 0.35 | 0.55 | 0.52 | 0.64 | 0.51 | 0.54 | 0.61 | 0.62 | 0.55 |
| CRC− | N440507 | 0.43 | 0.28 | 0.76 | 0.54 | 0.30 | 0.61 | 0.47 | 0.59 | 0.36 | 0.48 | 0.53 | 0.46 |
| CRC− | N376760 | 0.65 | 0.52 | 0.53 | 0.43 | 0.68 | 0.69 | 0.70 | 0.65 | 0.65 | 0.67 | 0.64 | 0.59 |
| CRC− | N469775 | 0.24 | 0.17 | 0.50 | 0.39 | 0.20 | 0.41 | 0.33 | 0.44 | 0.28 | 0.37 | 0.47 | 0.41 |
| CRC− | N491028 | 0.26 | 0.20 | 0.54 | 0.35 | 0.20 | 0.43 | 0.34 | 0.42 | 0.25 | 0.35 | 0.44 | 0.39 |
| CRC− | N146601 | 0.51 | 0.42 | 0.63 | 0.48 | 0.47 | 0.61 | 0.56 | 0.59 | 0.49 | 0.55 | 0.62 | 0.54 |
| CRC− | N557701 | 0.55 | 0.68 | 0.83 | 0.75 | 0.52 | 0.63 | 0.59 | 0.63 | 0.55 | 0.59 | 0.57 | 0.50 |
| CRC− | N557760 | 0.56 | 0.56 | 0.80 | 0.95 | 0.45 | 0.60 | 0.51 | 0.70 | 0.58 | 0.61 | 0.58 | 0.56 |
| CRC− | N557699 | 0.60 | 0.72 | 0.82 | 0.56 | 0.63 | 0.70 | 0.70 | 0.62 | 0.57 | 0.63 | 0.63 | 0.61 |
| CRC− | N593351 | 0.76 | 0.48 | 0.63 | 0.59 | 0.59 | 0.68 | 0.58 | 0.63 | 0.56 | 0.55 | 0.55 | 0.61 |
| CRC− | N744056 | 0.30 | 0.48 | 0.47 | 0.28 | 0.42 | 0.41 | 0.47 | 0.36 | 0.37 | 0.42 | 0.49 | 0.42 |
| CRC+ | CBSE011 | 5.13 | 5.12 | 12.17 | 5.43 | 3.45 | 8.15 | 6.13 | 6.29 | 2.76 | 5.05 | 6.17 | 5.30 |
| CRC+ | CLSP059 | 0.35 | 0.18 | 0.44 | 5.71 | 0.27 | 0.44 | 0.35 | 3.12 | 2.99 | 2.51 | 3.45 | 3.04 |
| CRC+ | CLSP104 | 0.27 | 7.10 | 0.44 | 0.48 | 4.85 | 0.40 | 3.80 | 0.49 | 3.82 | 3.19 | 5.63 | 4.96 |
| CRC+ | CBSE001 | 0.77 | 0.77 | 0.77 | 10.28 | 0.77 | 0.77 | 0.77 | 10.28 | 10.28 | 10.28 | 10.28 | 10.28 |
| CRC+ | CBSE016 | 19.26 | 5.83 | 12.92 | 6.18 | 12.85 | 17.57 | 13.18 | 13.35 | 9.81 | 10.69 | 9.02 | 7.73 |
| CRC+ | CBSE022 | 0.20 | 0.08 | 8.62 | 0.38 | 0.14 | 5.83 | 4.38 | 4.53 | 0.26 | 3.62 | 6.91 | 5.93 |

TABLE 5-continued

| Pathological condition | Patient identifier | Score 2[a] | Score 2[b] | Score 2[c] | Score 2[d] | Score 3[e] | Score 3[f] | Score 4[g] | Score 4[h] | Score 4[i] | Score 5[j] | Score 7[k] | Score 8[l] |
|---|---|---|---|---|---|---|---|---|---|---|---|---|---|
| CRC+ | CBSE025 | 0.72 | 0.50 | 8.93 | 0.87 | 0.55 | 6.18 | 4.69 | 4.87 | 0.65 | 3.94 | 5.58 | 4.80 |
| CRC+ | CLSP047 | 0.29 | 0.17 | 5.46 | 0.37 | 0.20 | 3.73 | 2.80 | 2.90 | 0.26 | 2.33 | 1.84 | 1.66 |
| CRC+ | CLSP062 | 0.37 | 5.28 | 6.47 | 0.40 | 3.67 | 4.46 | 5.91 | 3.47 | 2.88 | 4.83 | 5.23 | 4.66 |
| CRC+ | CLSP067 | 0.21 | 0.14 | 0.54 | 7.28 | 0.16 | 0.42 | 0.33 | 3.90 | 3.70 | 3.13 | 2.40 | 2.16 |
| CRC+ | CLSP080 | 0.40 | 0.46 | 5.77 | 0.69 | 0.35 | 3.89 | 2.97 | 3.89 | 0.35 | 2.97 | 2.19 | 1.88 |
| CRC+ | CLSP085 | 8.75 | 8.75 | 9.14 | 9.00 | 5.89 | 6.15 | 4.65 | 4.78 | 4.58 | 3.86 | 2.95 | 2.61 |
| CRC+ | CLSP086 | 168.1 | 0.24 | 0.35 | 0.31 | 112.2 | 112.3 | 84.30 | 84.34 | 84.29 | 67.54 | 48.35 | 42.34 |
| CRC+ | CLSP093 | 0.24 | 0.26 | 0.42 | 8.93 | 0.26 | 0.37 | 0.36 | 4.69 | 4.61 | 3.81 | 2.85 | 2.52 |
| CRC+ | CLSP100 | 0.44 | 0.19 | 6.86 | 7.48 | 0.35 | 4.79 | 3.63 | 7.28 | 3.95 | 5.86 | 4.32 | 3.79 |
| CRC+ | CLSP118 | 0.21 | 0.22 | 0.63 | 0.44 | 0.15 | 0.42 | 0.33 | 0.44 | 0.23 | 0.36 | 0.40 | 2.32 |
| CRC+ | CLSP145 | 0.51 | 0.42 | 7.10 | 0.78 | 0.38 | 4.83 | 3.65 | 3.83 | 0.49 | 3.09 | 2.41 | 2.11 |
| CRC+ | CLSP146 | 0.17 | 0.23 | 0.36 | 7.47 | 0.22 | 0.31 | 0.32 | 3.94 | 3.87 | 3.22 | 3.99 | 3.50 |
| CRC+ | CBSE004 | 0.37 | 0.27 | 7.18 | 0.18 | 0.41 | 5.02 | 3.89 | 3.85 | 0.39 | 3.18 | 9.53 | 8.19 |
| CRC+ | CBSE017 | 17.51 | 0.36 | 7.89 | 0.74 | 11.73 | 16.76 | 12.61 | 12.80 | 9.03 | 10.28 | 8.72 | 7.47 |
| CRC+ | CBSE018 | 0.19 | 0.17 | 0.42 | 0.26 | 0.19 | 0.36 | 0.32 | 0.36 | 0.24 | 0.33 | 2.80 | 2.40 |
| CRC+ | CLSP043 | 0.54 | 0.56 | 5.38 | 0.66 | 0.51 | 3.72 | 2.90 | 3.72 | 0.51 | 2.90 | 4.01 | 3.45 |
| CRC+ | CLSP060 | 0.64 | 0.66 | 8.88 | 6.69 | 0.65 | 6.13 | 4.76 | 7.77 | 3.66 | 6.35 | 5.39 | 4.66 |
| CRC+ | CLSP087 | 0.59 | 0.45 | 7.11 | 0.66 | 0.43 | 4.87 | 3.67 | 3.78 | 0.45 | 3.04 | 2.32 | 2.03 |
| CRC+ | CLSP088 | 13.90 | 7.95 | 0.67 | 5.87 | 14.44 | 9.58 | 11.07 | 10.03 | 13.67 | 11.13 | 8.01 | 7.01 |
| CRC+ | CLSP096 | 19.94 | 0.29 | 8.65 | 0.44 | 13.42 | 18.99 | 14.34 | 14.41 | 10.23 | 11.60 | 8.42 | 7.37 |
| CRC+ | CLSP105 | 23.90 | 0.88 | 7.46 | 0.73 | 16.23 | 20.62 | 15.69 | 15.61 | 12.32 | 12.67 | 10.82 | 9.47 |
| CRC+ | CLSP107 | 0.44 | 0.47 | 0.36 | 5.91 | 0.54 | 0.47 | 0.54 | 3.26 | 3.31 | 2.75 | 2.07 | 1.83 |
| CRC+ | CLSP113 | 0.31 | 0.29 | 0.49 | 8.43 | 0.28 | 0.41 | 0.36 | 4.43 | 4.33 | 3.59 | 2.66 | 2.33 |
| CRC+ | CLSP115 | 9.90 | 9.72 | 18.17 | 26.81 | 6.66 | 12.29 | 9.27 | 17.81 | 13.59 | 14.29 | 11.93 | 10.44 |
| CRC+ | CLSP117 | 0.75 | 0.57 | 8.98 | 7.36 | 0.60 | 6.20 | 4.72 | 8.12 | 3.92 | 6.55 | 6.25 | 5.48 |
| CRC+ | CLSP119 | 0.22 | 0.26 | 7.33 | 5.92 | 0.18 | 4.89 | 3.69 | 6.52 | 2.99 | 5.24 | 3.94 | 3.47 |
| CRC+ | CLSP122 | 0.66 | 0.40 | 0.68 | 0.47 | 0.56 | 0.75 | 0.65 | 0.69 | 0.55 | 0.62 | 3.60 | 3.15 |
| CRC+ | CLSP136 | 0.26 | 0.25 | 0.47 | 0.48 | 0.31 | 0.45 | 0.43 | 0.55 | 0.44 | 0.52 | 0.62 | 0.56 |
| CRC+ | CLSP143 | 7.99 | 0.40 | 0.80 | 0.82 | 5.37 | 5.64 | 4.26 | 4.47 | 4.27 | 3.60 | 2.69 | 2.37 |
| CRC+ | CLSP147 | 0.39 | 0.22 | 8.75 | 0.48 | 0.27 | 5.96 | 4.48 | 4.60 | 0.34 | 3.69 | 4.34 | 3.81 |
| CRC+ | CLSP154 | 9.94 | 0.43 | 6.34 | 0.49 | 6.76 | 10.70 | 8.13 | 8.16 | 5.20 | 6.60 | 4.93 | 4.31 |
| CRC+ | GHBD020 | 0.32 | 0.38 | 5.61 | 0.76 | 0.29 | 3.78 | 2.89 | 3.08 | 0.46 | 2.51 | 1.93 | 1.72 |
| CRC+ | GHBD025 | 0.27 | 0.25 | 6.97 | 0.46 | 0.21 | 4.69 | 3.55 | 3.65 | 0.29 | 2.94 | 2.29 | 2.00 |
| CRC+ | GHBD029 | 5.94 | 6.09 | 6.28 | 6.27 | 4.08 | 4.21 | 3.25 | 3.34 | 3.24 | 2.74 | 2.09 | 1.82 |
| CRC+ | CBSE005 | 11.39 | 11.65 | 17.84 | 18.52 | 7.78 | 11.91 | 9.07 | 12.51 | 9.42 | 10.12 | 12.87 | 11.28 |
| CRC+ | CBSE006 | 24.67 | 24.68 | 49.15 | 24.98 | 16.52 | 24.67 | 16.52 | 16.71 | 12.59 | 12.59 | 12.59 | 10.10 |
| CRC+ | CBSE007 | 5.49 | 5.45 | 10.74 | 25.72 | 3.71 | 5.49 | 3.71 | 17.23 | 12.96 | 12.96 | 12.96 | 10.38 |
| CRC+ | CBSE010 | 30.57 | 73.65 | 30.99 | 32.35 | 53.22 | 24.78 | 43.22 | 22.56 | 43.90 | 37.76 | 34.94 | 29.99 |
| CRC+ | CBSE013 | 12.31 | 17.52 | 20.52 | 18.49 | 11.91 | 13.91 | 13.20 | 13.69 | 12.19 | 13.17 | 12.77 | 10.95 |
| CRC+ | CBSE023 | 5.78 | 5.68 | 5.84 | 5.83 | 4.02 | 4.13 | 3.22 | 3.30 | 3.22 | 2.74 | 2.42 | 2.11 |
| CRC+ | CLSP044 | 103.9 | 0.25 | 0.53 | 0.29 | 69.37 | 69.55 | 52.23 | 52.25 | 52.11 | 41.85 | 30.04 | 26.32 |
| CRC+ | CLSP050 | 5.97 | 5.86 | 13.93 | 11.14 | 4.03 | 9.40 | 7.09 | 9.73 | 5.70 | 7.81 | 7.77 | 6.84 |
| CRC+ | CLSP072 | 11.33 | 14.86 | 14.32 | 11.06 | 13.61 | 13.25 | 14.48 | 12.58 | 12.85 | 13.70 | 9.96 | 8.73 |
| CRC+ | CLSP073 | 0.67 | 14.22 | 7.20 | 6.00 | 9.65 | 4.96 | 10.62 | 6.51 | 10.02 | 10.73 | 7.76 | 6.81 |
| CRC+ | CLSP074 | 0.29 | 0.41 | 6.82 | 0.66 | 0.36 | 4.63 | 3.59 | 3.71 | 0.51 | 3.07 | 2.31 | 2.07 |
| CRC+ | CLSP089 | 25.65 | 0.62 | 9.83 | 0.41 | 17.37 | 23.51 | 17.84 | 17.73 | 13.13 | 14.35 | 10.39 | 9.11 |
| CRC+ | CLSP091 | 5.55 | 0.27 | 0.39 | 6.43 | 3.83 | 3.91 | 3.03 | 6.11 | 6.05 | 4.96 | 3.71 | 3.26 |
| CRC+ | CLSP094 | 6.67 | 0.36 | 0.25 | 0.31 | 4.61 | 6.67 | 4.61 | 4.57 | 3.54 | 3.54 | 2.89 | 2.44 |
| CRC+ | CLSP097 | 0.31 | 0.30 | 0.64 | 0.55 | 0.27 | 0.50 | 0.42 | 0.55 | 0.38 | 0.48 | 0.46 | 0.40 |
| CRC+ | CLSP106 | 5.05 | 5.13 | 12.36 | 11.50 | 3.42 | 8.24 | 6.22 | 9.40 | 5.78 | 7.55 | 5.53 | 4.84 |
| CRC+ | CLSP121 | 0.22 | 0.23 | 0.51 | 0.41 | 0.21 | 0.40 | 0.35 | 0.44 | 0.30 | 0.39 | 1.93 | 1.69 |
| CRC+ | CLSP123 | 0.63 | 0.62 | 9.03 | 14.97 | 0.51 | 6.12 | 4.66 | 11.83 | 7.63 | 9.52 | 11.26 | 9.85 |
| CRC+ | CLSP138 | 9.60 | 0.30 | 8.82 | 0.56 | 6.42 | 12.10 | 9.09 | 9.22 | 4.96 | 7.39 | 5.43 | 4.76 |
| CRC+ | CLSP141 | 0.43 | 0.38 | 0.63 | 10.19 | 0.32 | 0.49 | 0.40 | 5.30 | 5.18 | 4.27 | 3.31 | 2.90 |
| CRC+ | CLSP153 | 33.40 | 23.59 | 21.96 | 29.87 | 28.97 | 27.88 | 25.93 | 29.08 | 29.89 | 27.28 | 19.56 | 17.12 |
| CRC+ | GHBD019 | 7.06 | 0.24 | 0.68 | 0.60 | 4.71 | 5.00 | 3.75 | 3.93 | 3.71 | 3.14 | 2.34 | 2.08 |
| CRC+ | CBSE012 | 5.81 | 12.11 | 0.47 | 0.30 | 11.85 | 4.10 | 9.06 | 3.16 | 8.98 | 7.32 | 6.19 | 5.30 |
| CRC+ | CBSE019 | 6.40 | 0.63 | 0.88 | 7.05 | 4.42 | 4.58 | 3.55 | 6.76 | 6.64 | 5.50 | 4.71 | 4.04 |
| CRC+ | CBSE026 | 195.7 | 119.8 | 8.71 | 6.43 | 210.2 | 136.2 | 161.9 | 105.3 | 160.8 | 132.1 | 95.87 | 83.92 |
| CRC+ | CBSE027 | 175.0 | 0.55 | 5.36 | 5.79 | 175.0 | 120.0 | 120.0 | 92.78 | 120.3 | 92.78 | 68.71 | 61.25 |
| CRC+ | CLSP042 | 153.8 | 0.76 | 5.43 | 8.15 | 102.8 | 105.9 | 79.62 | 83.31 | 80.98 | 66.81 | 50.00 | 43.77 |
| CRC+ | CLSP057 | 15.32 | 0.19 | 0.40 | 10.84 | 10.30 | 10.44 | 7.89 | 13.21 | 13.11 | 10.62 | 12.94 | 12.80 |
| CRC+ | CLSP068 | 337.0 | 120.0 | 5.60 | 7.64 | 304.0 | 228.2 | 231.0 | 174.8 | 232.0 | 187.7 | 138.3 | 121.2 |
| CRC+ | CLSP079 | 0.43 | 25.92 | 0.59 | 0.60 | 25.92 | 0.59 | 17.53 | 0.65 | 17.54 | 13.34 | 9.16 | 7.91 |
| CRC+ | CLSP083 | 0.37 | 0.46 | 0.46 | 0.54 | 0.41 | 0.42 | 0.43 | 0.48 | 0.47 | 0.48 | 0.44 | 0.39 |
| CRC+ | CLSP095 | 150.8 | 0.59 | 0.59 | 5.56 | 100.8 | 100.8 | 75.81 | 78.29 | 78.29 | 62.80 | 46.47 | 40.69 |
| CRC+ | CLSP109 | 0.47 | 9.79 | 0.63 | 34.00 | 9.79 | 0.63 | 6.79 | 22.93 | 29.04 | 21.97 | 17.37 | 14.96 |
| CRC+ | CLSP132 | 7.74 | 7.84 | 15.99 | 17.61 | 5.42 | 10.86 | 8.34 | 13.23 | 9.15 | 10.74 | 9.52 | 8.36 |
| CRC+ | CLSP156 | 45.79 | 24.26 | 8.49 | 0.73 | 46.47 | 35.97 | 38.94 | 27.17 | 35.05 | 31.31 | 28.46 | 24.92 |
| CRC+ | CLSP159 | 67.36 | 33.80 | 6.71 | 0.66 | 67.28 | 49.22 | 53.70 | 37.13 | 50.67 | 43.13 | 32.70 | 28.61 |
| CRC+ | CLSP160 | 7.86 | 7.49 | 7.73 | 42.10 | 5.32 | 5.48 | 4.17 | 21.48 | 21.36 | 17.23 | 12.46 | 10.90 |
| CRC+ | CLSP161 | 18.00 | 0.52 | 8.72 | 0.61 | 12.23 | 17.70 | 13.45 | 13.49 | 9.40 | 10.94 | 7.99 | 6.99 |
| Threshold | | 0.96 | 0.96 | 0.97 | 0.95 | 0.96 | 0.96 | 0.96 | 0.77 | 0.77 | 0.77 | 0.77 | 0.77 |
| Specificity (%) | | 100 | 100 | 100 | 100 | 100 | 100 | 100 | 100 | 100 | 100 | 100 | 100 |

TABLE 5-continued

| Pathological condition | Patient identifier | Score $2^a$ | Score $2^b$ | Score $2^c$ | Score $2^d$ | Score $3^e$ | Score $3^f$ | Score $4^g$ | Score $4^h$ | Score $4^i$ | Score $5^j$ | Score $7^k$ | Score $8^l$ |
|---|---|---|---|---|---|---|---|---|---|---|---|---|---|
| Sensitivity (%) | | 52.56 | 35.90 | 62.82 | 89.13 | 58.97 | 76.92 | 80.77 | 88.46 | 75.64 | 91.03 | 94.87 | 96.15 |
| CRC+ above the threshold | | 41 | 28 | 49 | 41 | 46 | 60 | 63 | 69 | 59 | 71 | 74 | 75 |

Score $2^a$: combination of CEA and Prodefensin-A6
Score $2^b$: combination of CA19-9 and Prodefensin-A6
Score $2^c$: combination of beta2-microglobulin and Prodefensin-A6
Score $2^d$: combination of L-FABP and Prodefensin-A6
Score $3^e$: combination of CEA, CA19-9 and Prodefensin-A6
Score $3^f$: combination of CEA, beta2-microglobulin and Prodefensin-A6
Score $4^g$: combination of CEA, beta2-microglobulin, CA19-9 and Prodefensin-A6
Score $4^h$: combination of CEA, beta2-microglobulin, L-FABP and Prodefensin-A6
Score $4^i$: combination of CEA, CA19-9, L-FABP and Prodefensin-A6
Score $5^j$: combination of CEA, beta2-microglobulin, CA19-9, L-FABP and Prodefensin-A6
Score $7^k$: combination of CEA, beta2-microglobulin, CA19-9, galectin-3, Prodefensin-A6, L-FABP and MIF
Score $8^l$: combination of CEA, beta2-microglobulin, CA19-9, Prodefensin-A6, galectin-3, L-FABP, MIF and I-plastin
CRC+ = patients having colorectal cancer (adenocarcinoma), CRC− = healthy individuals.

Example 5

Detection of the Tumour Markers by Means of the LC-MRM-MS Technique

1. Methodology

In order to be able to decrease the detection limit to a few ng/ml, an improved MRM-MS method was used. The successive steps of this method are: 1) immunodepletion of the abundant proteins, 2) trypsin digestion, 3) SPE (solid-phase extraction) fractionation of the peptides, 4) liquid chromatography (LC) coupled to MRM-MS.

The setting up was carried out on spike samples by adding the Prodefensin-A6 synthetic peptide (SEQ ID No.1).

Immunodepletion. The depletion of the abundant proteins in the serum was carried out using the commercial Vivapure anti-HSA kit from Vivascience. Alternatively, the Proteoextract Albumin/IgG kit from Calbiochem and the Aurum™ serum Protein Minikit from Bio-Rad were also used. It is also possible to produce the specific resins in the laboratory, by coupling a monoclonal antibody directed against the protein to be depleted, to a CNBr-activated Sepharose 4B resin (Amersham Bioscience), according to the producer's instructions.

Enzymatic digestion. The depleted serum samples are denatured in a 6M urea solution buffered with 10 mM of Tris, pH 8, and containing 30 mM of dithiothreitol, for 40 minutes at 40° C., and then alkylated with 50 mM iodoacetamide, at ambient temperature for 40 minutes, in the dark. They are diluted six-fold in water, and the trypsin digestion is then carried out at 37° C. overnight, using an enzyme/substrate ratio of 1/30 (Promega). The digestion is stopped by adding formic acid at a final concentration of 0.5%. The digested samples are desalified by solid-phase extraction (SPE) using the Oasis HLB 3 cc reverse-phase cartridges (60 mg) (Waters). After application of the sample, the cartridges are washed with 1 ml of formic acid at 0.1%, and then the elution is carried out with a methanol/water mixture (80/20 v/v) containing 0.1% of formic acid. The eluates are dried under vacuum.

SPE fractionation. The dry samples are taken up in 1 ml of acetate buffer and loaded onto Oasis MCX (mixed cation exchange) 60 mg mixed cartridges (hydrophobic and cation exchange) (Waters) pre-equilibrated in acetate buffer and methanol. The cartridges are washed with 1 ml of acetate buffer and 1 ml of methanol. The peptides of to interest (Table 6) are eluted with 1 ml of a methanol/acetate buffer mixture (50/50 v/v). The pH of the acetate buffer is chosen according to the isoelectric point of the peptide of interest. The eluates are dried under vacuum, and dissolved in 200 µl of a solution of acetonitrile/water (3/97 v/v) containing 0.1% of formic acid. A 50 µl aliquot was injected into the LC coupled to an MS-MS system.

Liquid chromatography and mass spectrometry. The LC-MS analysis was carried out on an HP 1100 series high pressure chromatographic system (HPLC) with a binary pump and injector (Agilent Technologies), coupled to a mass spectrometer, either a Sciex API 2000 triple quadripole or a Sciex API 4000 Qtrap (hybrid triple quadripole-ion trap MS) (MDS Sciex) for better sensitivity. The LC separation was carried out on a $C_{18}$ Symmetry column (Waters), at an elution flow rate of 300 µl/min (eluent A=0.1% formic acid in water, eluent B=0.1% formic acid in acetonitrile, linear gradient of 5% B to 50% B in 25 min, then of 50% B to 100% B in 3 min) The MS analysis is carried out in the positive ionization mode at a voltage of 5500 V, applied as a needle voltage, enabling ionization in the source. The instrument verification and the data acquisition are carried out with the Analyst 1.4.1 software. The nebulizing gas (air) and curtain gas (nitrogen) flows are 30 and 20 psi, respectively. The Turbo V™ ion source is adjusted to 400° C., the auxiliary nitrogen flow to 40 psi. The MRM transitions recorded for each peptide are reproduced in Table 6. The collision energy (CE), the declustering potential (DP) and the collision cell exit potential (CXP) are optimized for each of the MRM transitions selected.

2. Results

The list of theoretical MRM transitions of the sequence SEQ ID No.1 was generated using the MIDAS (MRM-initiated Detection and Sequencing) software. This list comprises all the double-charged or triple-charged parent ions of the theoretical tryptic peptides in a mass range of from 800 to 3000 Da and all the possible ion fragments of y or b type. For each protein, each possible transition was tested in order to determine the most sensitive and most specific transitions. The result of this selection is reproduced in Table 6. An example of optimization of the SPE step for transition 727/556 of the peptide EPLQAEDDPLQAK (SEQ ID No.30) is given in FIG. 7. The MCX chromatographic separation was carried out at various pHs, the pH selected for the rest of the experiments being the pH which makes it possible to obtain the highest area of the peak.

Furthermore, using a heavy peptide of AQUA type (Sigma) or alternatively a heavy recombinant protein that will serve as an assay standard, it is possible to quantify, in an absolute manner, the tumour marker of interest in a complex biological medium.

TABLE 6

Prodefensin-A6

| Sequence (SEQ ID No.) | pI | Q1 | Q3 | DP | CE | CXP |
|---|---|---|---|---|---|---|
| EPLQAEDDPLQAK (SEQ ID No. 30) | 3.57 | 727.4 | 556.4 | 50 | 40 | 28 |
| | | | 218.2 | 50 | 35 | 8 |
| | | | 915.4 | 50 | 30 | 25 |
| | | | 986.4 | 50 | 35 | 27 |
| AYEADAQEQR (SEQ ID No. 31) | 3.93 | 590.8 | 746.4 | 100 | 30 | 11 |
| | | | 817.4 | 100 | 30 | 18 |
| | | | 631.3 | 100 | 30 | 11 |
| | | | 560.3 | 100 | 30 | 11 |
| | | | 946.4 | 100 | 35 | 20 |

LITERATURE REFERENCES

1: J. D. Potter, 1999, J Natl Cancer Inst, 91, 916-32
2: J. Faivre, 2001, Epidemiologic et dépistage du cancer colorectal [Colorectal cancer epidemiology and screening], publisher Springer
3: D. E. Jones and C. L. Bevins, 1992, J Biol Chem, 23216-23225
4: C. L. Bevins et al., 1996, Genomics, 95-106
5: I. Lawrance et al., 2001, Hum Mol Gen, 445-456
6: M. J. Nam et al., 2005, J Biol Chem, 8260-8265
7: E. Remold-O'Donnell et al., 1992, Proc Natl Acad Sci USA, 89, 563-5639
8: J. Cooley et al., 2001, Biochemistry, 15762-15770
9: M. Algrain et al., 1993, J Cell Biol, 120, 129-139
10: W. G. Jiang and S. Hiscox, 1996, Anticancer Res, 16, 861-865
11: S. Hiscox and W. G. Jiang, 1999, J Cell Sci, 112, 3081-3090
12: T. Xiao et al., 2005, Mol Cell Proteomics, 4, 1480-1486
13: M. Anders and W. Dekant, 1994, Advances in Pharmacology, 431-448
14: K. Lorentz et al., 1975, Clinica Chimica Acta, 263-269
15: K. Lorentz and B. Flatter, 1975, Clinica Chimica Acta, 271-274
16: R. M. Cook et al., 1993, J Biol Chem, 17010-17017
17: Y. E. Miller et al., 1989, J Clin Invest, 2120-2124
18: S. Balabanov et al., 2001, Eur J Biochem, 5977-5980
19: E. Chan et al., 1985, J Biol Chem, 260, 2629-2632
20: R. Das et al., 2001, Clin Cancer Res, 7, 1706-1715
21: J. Stulik et al., 2001, Electrophoresis, 22, 3019-3025
22: T. Yamazaki et al., 1999, J Surg Oncol, 72, 83-87
23: D. A. Sweetser et al., 1987, J Biol Chem, 266, 16060-16071
24: M. Pelsers et al., 2003, Clin Biochem, 36, 529-535
25: R. Xiao, et al., 2005, Molecular Cancer, 4, 1-17
26: E. E. Niederkofler et al., 2003, J Lipid Res, 44, 630-639
27: G. L. Horan, 2006, Clinical Chemistry, 52(7), 1223-1237
28: J. Y. Engwegen et al., 2006, World J Gastroenterol, 12(10), 1536-1544
29: Z. Zhang et al., 2004, Cancer Research, 64, 5882-5890
30: H. Hachem et al., 1986, J Chem Clin Biochem, 24, 161-166
31: C. S. Lin, et al., 1993, J Biol Chem, 268, 2781-92
32: V. Delanote et al., 2005, Acta Pharama Sinica, 769-779
33: A. P. Arrigo et al., 1988, Nature, 331, 192-194
34: T. Lavabre-Bertrand et al., 2001, Cancer, 92, 2493-2500
35: S, Nakahara et al., 2005, Apoptosis, 10, 267-275
36: I. Iurisci et al., 2000, Clin Can Res, 6, 1389-1393
37: M. K. Schwartz, 2006, Clin Chim Acta, 1992, 77-82
38: D. J. McCool et al., 1999, Biochem J, 593-600
39: J. L. Iovanna et al., 1994, Gastroenterology, 106, 728-734
40: Y. Motoo et al., 1999, Dig Dis Sci, 44, 1142-1147
41: M. Herlyn et al., 1979, Proc Natl Acad Sci USA, 76, 1438-1442
42: A. Armstrong and S. Eck, 2003, Cancer Biol Ther, 2, 320-325
43: D. Herlyn et al., 1982, Proc Natl Acad Sci USA, 79, 4761-4765
44: H. Abe et al., 2002, J Immunol Methods, 270, 227-233
45: V. Barak et al., 2004, Clin Biochem, 37, 529-540
46: H. Kim et al., 2006, Ann Clin Lab Sci, 36, 294-298
47: F. Roca et al., 2006, J Surg Oncol, 151-160
48: C. H. Damsky et al., 1983, Cell, 455-466
49: M. Katayama et al., 1994, Br J Cancer, 580-585
50: C. Willmanns et al., 2004, Clin Exp Metastasis, 75-78
51: P. Gold and S. Freedman, 1965, J Exp Med, 467-481
52: M. Duffy, 2001, Clin Chem, 624-630
53: Y. Kim et al., 2003, Ann Clin Lab Sci, 32-38
54: J. L. Magnani et al., 1983, Cancer Research, 43, 5489-5492
55: J. Holmgren et al., 1984, Br Med J (Clin. Re. Ed.), 288, 1479-1482
56: T. L. Klug et al., 1986, Int J Cancer, 38, 6661-669
57: P. Kuusela et al., 1991, Br J Cancer, 63, 636-640
58: M. Holland et al., 1993, Medicina (B. Aires), 53(2), 117-23
59: F. Model et al., July 2006, World Congress on Gastrointestinal Cancer, "Detection of Methylated DNA in Plasma from Colorectal Cancer Patients and Controls by Real-Time PCR Analysis of Septin 9"
60: M. P. Ebert et al., 2006, Gastroentrology, 131(5), 1418-1430
61: C. Bianco et al., 2006, Clin Cancer Res, 12, 5158-5164
62: Wilson et al., 2005, Gastroenterology, 129: 1485-1503
63: Lee et al., 2008, Am. J. Clin. Pathol., 129: 772-779
64: P. D. Hardt et al., 2004, Br J Cancer, 91(5): 980-984
65: E. Sagiv et al., 2008, Cancer Res, 68(8): 2803-2812
66: E.S Leman et al., 2007, Cancer Res, 67(12): 5600-5605
67: M. Jambon et al., 2005, Structural bioinformatics, 21(20): 3929-3930
68: R A. Bauer et al., 2008, Nucleic Acids Research, 36: 47-54
69: R. Yasumatsu et al., 2006, Am J Physiol Lung Cell Mol Physiol 291, L619-L627
70: J. Chevalier et al., 1997, J Histochem Cytochem, 45, 481-491
71: S. Patterson, 2000, Physiological Genomics 2, 59-65
72: L. J. Kricka et al., 1999, Clinical Chemistry, 45(4), 453-458
73: S. Tyagi and F. R. Kramer, 1996, Nature Biotech, 14, 303-308
74: T. F. Imperiale et al., 2004, N Engl J Med, 351(26), 2704-2714
75: D. A. Ahlquist et al., 2000, Gastroenterology, 119, 1219-1227
76: I. H. Wong, 2006, Methods Mol Biol, 336, 33-46
77: M. P. Ebert et al., 2005, Neoplasia, 7(8), 771-778
78: C. Lofton-Day et al., 2007, AACR Annual Meeting 2007, Los Angeles, U.S.A., Poster no LB-165, Clinical case-control study in plasma shows that the DNA methylation biomarker, Septin-9, detects 70% of stage I-Ill colorectal cancer patients 79: P. Métézeau et al., La cytométrie en flux pour l'étude de la cellule normale or pathologique [Flow cytometry for studying the normal or pathological cell) (Volume I), publisher Medsi-MacGraw-Hill 80: J. Mathieu et al, 2006, Fonctions cellulaires et métabolisme [Cell functions and metabolism]. In: (coordinators: Ronot X. et al.). La cytométrie en flux [Flow cytometry]. Tec & Doc, 255-298. ISBN 978-2-7430-0898-7

81: G. Köhler and C. Milstein, 1975, Nature, 256, 495-497

82: G. Köhler and C. Milstein, 1976, Eur J Immunol, 6, 511-519

---

The invention claimed is:

1. An in vitro method for diagnosing colorectal cancer using a biological sample obtained from a patient suspected of having colorectal cancer, comprising:
   assaying for the level of the Prodefensin-A6 protein present in the biological sample using at least one antibody or antibody fraction specific for the Prodefensin-A6 protein; and
   determining whether the level of the Prodefensin-A6 protein is indicative of the patient having colorectal cancer, wherein the level of the Prodefensin-A6 protein is assayed by detecting any of the signal peptide or the propeptide of the Prodefensin-A6 protein, whether as part of the intact Prodefensin-A6 protein or a fragment thereof, to the exclusion of the mature Defensin-A6 protein or fragments of the mature Defensin-A6 protein.

2. The method of claim 1, wherein the biological sample is a sample remote from any colorectal tumor.

3. The method of claim 1, wherein the level of the Prodefensin-A6 protein is assayed by detecting the propeptide of the Prodefensin-A6 protein.

4. The method of claim 1, wherein the level of the Prodefensin-A6 protein is assayed using at least one monoclonal antibody specific for the propeptide.

5. The method of claim 1, wherein the level of the Prodefensin-A6 protein is assayed using at least one monoclonal antibody that recognizes an epitope including an amino acid sequence selected from the group consisting of the amino acid sequences of SEQ ID NOS: 4-6.

6. The method of claim 1, wherein the level of the Prodefensin-A6 protein is assayed using at least one monoclonal antibody that recognizes an epitope including the amino acid sequence of $X_1 X_2 X_3 X_4 X_5 X_6 X_7 X_8 R$ (SEQ ID NO: 7), in which $X_1$ is V or L, $X_2$ is T or L, $X_3$ is P, S or C, $X_4$ is P or S, $X_5$ is W or T, $X_6$ is A, Q, M, C or E, $X_7$ is I, E or D and $X_8$ is F, Y, S or L.

7. The method of claim 1, wherein the level of the Prodefensin-A6 protein is assayed using at least one monoclonal antibody that recognizes an epitope including the amino acid sequence of $X_1 X_2 X_3 X_4 X_5 X_6 HX_7$ (SEQ ID NO: 13), in which $X_1$ is S or T, $X_2$ is C or absent, $X_3$ is T, L or E, $X_4$ is H or R, $X_5$ is I, F or E, $X_6$ is G or V and $X_7$ is C or N.

8. The method of claim 1, wherein the level of the Prodefensin-A6 protein is assayed using at least one monoclonal antibody that recognizes an epitope including the amino acid sequence of $X_1 HPX_2 X_3 X_4 X_5 X_6 X_7$ (SEQ ID NO: 17), in which $X_1$ is P or W, $X_2$ is W or E, $X_3$ is S, A, Q or W, $X_4$ is M, L, R or P, $X_5$ is H, F, W or G, $X_6$ is V or A and $X_7$ is I or V.

9. The method of claim 1, wherein the level of the Prodefensin-A6protein is assayed using at least one monoclonal antibody that recognizes an epitope including the amino acid sequence of $X_1 HX_2 X_3 X_4 X_5$ (SEQ ID NO: 22), in which $X_1$ is Y or N, $X_2$ is E, D or Q, $X_3$ is T, N, R, M or K, $X_4$ is W, H or F and $X_5$ is P or G.

10. The method of claim 1, wherein the level of the Prodefensin-A6 protein is assayed using at least one monoclonal antibody that recognizes an epitope including an amino acid sequence selected from the group consisting of the amino acid sequences of SEQ ID NOS: 8-12, 14-16, 18-21, and 23-29.

11. The method of claim 1, further comprising assaying for at least one other tumor marker selected from the group consisting of leukocyte elastase inhibitor, ezrin, aminoacylase 1, liver fatty acid-binding protein, intestinal fatty acid-binding protein, apolipoprotein AI, apolipoprotein AII, I-plastin, beta2-microglobulin, proteasome 20S, galectin-3, L-lactate dehydrogenase chain B, calreticulin, regenerating islet-derived protein 3 alpha, tumour-associated calcium signal transducer 1, keratin type II cytoskeletal 8, keratin type I cytoskeletal 18, keratin type I cytoskeletal 19, epithelial cadherin, CEA, villin, CA19-9, CA 242, CA 50, CA 72-2, testosterone, TIMP-1, cripto-1, protein disulphide isomerase, intelectin-1, cytokeratin 20, translationally-controlled tumour protein, (Pro)defensin-A5, MIF, pyruvate kinase M2-PK, calgranulin C, CD24, CCSA-3, CCSA-4, methylated DNA in the blood, specific alterations in fecal DNA fragments, and fecal human haemoglobin.

12. The method of claim 1, further comprising assaying for a member selected from the group consisting of:
(i) L-FABP;
(ii) CA19-9 and CEA;
(iii) beta2-microglobulin and CEA;
(iv) beta2-microglobulin, CA19-9 and CEA;
(v) beta2-microglobulin, L-FABP and CEA;
(vi) L-FABP, CA19-9 and CEA;
(vii) beta2-microglobulin, CA19-9 and CEA;
(viii) beta2-microglobulin, CA19-9, L-FABP and CEA;
(ix) beta2-microglobulin, CA19-9, galectin-3, L-FABP, MIF and CEA; and
(x) beta2-microglobulin, CA19-9, galectin-3, L-FABP, MIF, I-plastin and CEA.

13. An in vitro method for providing screening, diagnosis, therapeutic follow-up, prognosis, or relapse diagnosis of colorectal cancer using a biological sample obtained from a patient in need thereof, comprising:
assaying for the level of the Prodefensin-A6 protein present in the biological sample using at least one antibody or antibody fraction specific for the Prodefensin-A6 protein; and
determining whether the level of the Prodefensin-A6 protein is indicative of the presence, regression, or progression of colorectal cancer in the patient, wherein the level of the Prodefensin-A6 protein is assayed by detecting any of the signal peptide or the propeptide of the Prodefensin-A6 protein, whether as part of the intact Prodefensin-A6 protein or a fragment thereof, to the exclusion of the mature Defensin-A6 protein or fragments of the mature Defensin-A6 protein.

14. The method of claim 13, wherein the biological sample is a sample remote from any colorectal tumor.

15. The method of claim 13, wherein the level of the Prodefensin-A6 protein is assayed by detecting the propeptide of the Prodefensin-A6 protein.

16. The method of claim 13, wherein the level of the Prodefensin-A6 protein is assayed using at least one monoclonal antibody specific for the propeptide.

17. The method of claim 13, wherein the level of the Prodefensin-A6 protein is assayed using at least one monoclonal antibody that recognizes an epitope including an amino acid sequence selected from the group consisting of the amino acid sequences of SEQ ID NOS: 4-6.

18. The method of claim 13, wherein the level of the Prodefensin-A6 protein is assayed using at least one monoclonal antibody that recognizes an epitope including the amino acid sequence of $X_1 X_2 X_3 X_4 X_5 X_6 X_7 X_8 R$ (SEQ ID NO: 7), in which $X_i$ is V or L, $X_2$ is T or L, $X_3$ is P, S or C, $X_4$ is P or S, $X_5$ is W or T, $X_6$ is A, Q, M, C or E, $X_7$ is 1, E or D and $X_8$ is F, Y, S or L.

19. The method of claim 13, wherein the level of the Prodefensin-A6 protein is assayed using at least one monoclonal antibody that recognizes an epitope including the amino acid sequence of $X_1 X_2 X_3 X_4 X_5 X_6 HX_7$ (SEQ ID NO: 13), in which $X_1$ is S or T, $X_2$ is C or absent, $X_3$ is T, L or E, $X_4$ is H or R, $X_5$ iS I, F or E, $X_6$ is G or V and $X_7$ is C or N.

20. The method of claim 13, wherein the level of the Prodefensin-A6 protein is assayed using at least one monoclonal antibody that recognizes an epitope including the amino acid sequence of $X_1$ PHX$_2 X_3 X_4 X_5 X_6 X_7$ (SEQ ID NO: 17), in which $X_1$ is P or W, $X_2$ iS W or E, $X_3$ iS S, A, Q or W, $X_4$ is M, L, R or P, $X_5$ is H, F, W or G, $X_6$ is V or A and $X_7$ iS I or V.

21. The method of claim 13, wherein the level of the Prodefensin-A6 protein is assayed using at least one monoclonal antibody that recognizes an epitope including the amino acid sequence of $X_1 HX_2 X_3 X_4 X_5$ (SEQ ID NO: 22), in which $X_1$ is Y or N, $X_2$ is E, D or Q, $X_3$ is T, N, R, M or K, $X_4$ iS W, H or F and $X_5$ iS P or G.

22. The method of claim 13, wherein the level of the Prodefensin-A6 protein is assayed using at least one monoclonal antibody that recognizes an epitope including an amino acid sequence selected from the group consisting of the amino acid sequences of SEQ ID NOS: 8-12, 14-16, 18-21, and 23-29.

23. The method of claim 1, wherein the level of the Prodefensin-A6 protein is assayed by an automated system.

24. The method of claim 13, wherein the level of the Prodefensin-A6 protein is assayed by an automated system.

25. A method of determining the level of the Prodefensin-A6 protein in a biological sample comprising assaying for the level of the Prodefensin-A6 protein present in the biological sample using at least one antibody or antibody action specific for the Prodefensin-A6 protein,
wherein the level of the Prodefensin-A6 protein is assayed by detecting any of the signal peptide or the propeptide of the Prodefensin-A6 protein, whether as part of the intact Prodefensin-A6 protein or a fragment thereof, to the exclusion of the mature Defensin-A6 protein or fragments of the mature Defensin-A6 protein.

26. The method of claim 25, wherein the biological sample is a sample remote from any colorectal tumor.

27. The method of claim 25, wherein the level of the Prodefensin-A6protein is assayed by detecting the propeptide of the Prodefensin-A6 protein.

* * * * *

SEQUENCE LISTING

```
<160> NUMBER OF SEQ ID NOS: 31

<210> SEQ ID NO 1
<211> LENGTH: 81
<212> TYPE: PRT
<213> ORGANISM: human

<400> SEQUENCE: 1

Glu Pro Leu Gln Ala Glu Asp Asp Pro Leu Gln Ala Lys Ala Tyr Glu
1               5                   10                  15

Ala Asp Ala Gln Glu Gln Arg Gly Ala Asn Asp Gln Asp Phe Ala Val
            20                  25                  30

Ser Phe Ala Glu Asp Ala Ser Ser Ser Leu Arg Ala Leu Gly Ser Thr
        35                  40                  45

Arg Ala Phe Thr Cys His Cys Arg Arg Ser Cys Tyr Ser Thr Glu Tyr
    50                  55                  60

Ser Tyr Gly Thr Cys Thr Val Met Gly Ile Asn His Arg Phe Cys Cys
65                  70                  75                  80

Leu

<210> SEQ ID NO 2
<211> LENGTH: 46
<212> TYPE: PRT
<213> ORGANISM: human

<400> SEQUENCE: 2

Glu Pro Leu Gln Ala Glu Asp Asp Pro Leu Gln Ala Lys Ala Tyr Glu
1               5                   10                  15

Ala Asp Ala Gln Glu Gln Arg Gly Ala Asn Asp Gln Asp Phe Ala Val
            20                  25                  30

Ser Phe Ala Glu Asp Ala Ser Ser Ser Leu Arg Ala Leu Gly
        35                  40                  45

<210> SEQ ID NO 3
<211> LENGTH: 43
<212> TYPE: PRT
<213> ORGANISM: human

<400> SEQUENCE: 3

Ala Glu Asp Asp Pro Leu Gln Ala Lys Ala Tyr Glu Ala Asp Ala Gln
1               5                   10                  15

Glu Gln Arg Gly Ala Asn Asp Gln Asp Phe Ala Val Ser Phe Ala Glu
            20                  25                  30

Asp Ala Ser Ser Ser Leu Arg Ala Leu Gly Ser
        35                  40

<210> SEQ ID NO 4
<211> LENGTH: 2
<212> TYPE: PRT
<213> ORGANISM: human

<400> SEQUENCE: 4

Asp Pro
1
```

```
<210> SEQ ID NO 5
<211> LENGTH: 3
<212> TYPE: PRT
<213> ORGANISM: human

<400> SEQUENCE: 5

Asp Pro Leu
1

<210> SEQ ID NO 6
<211> LENGTH: 6
<212> TYPE: PRT
<213> ORGANISM: human

<400> SEQUENCE: 6

Glu Asp Asp Pro Leu Gln
1               5

<210> SEQ ID NO 7
<211> LENGTH: 9
<212> TYPE: PRT
<213> ORGANISM: artificial sequence
<220> FEATURE:
<223> OTHER INFORMATION: epitope
<220> FEATURE:
<221> NAME/KEY: MISC_FEATURE
<222> LOCATION: (1)..(1)
<223> OTHER INFORMATION: V ou L
<220> FEATURE:
<221> NAME/KEY: MISC_FEATURE
<222> LOCATION: (2)..(2)
<223> OTHER INFORMATION: T ou L
<220> FEATURE:
<221> NAME/KEY: MISC_FEATURE
<222> LOCATION: (3)..(3)
<223> OTHER INFORMATION: P, S ou C
<220> FEATURE:
<221> NAME/KEY: MISC_FEATURE
<222> LOCATION: (4)..(4)
<223> OTHER INFORMATION: P ou S
<220> FEATURE:
<221> NAME/KEY: MISC_FEATURE
<222> LOCATION: (5)..(5)
<223> OTHER INFORMATION: W ou T
<220> FEATURE:
<221> NAME/KEY: MISC_FEATURE
<222> LOCATION: (6)..(6)
<223> OTHER INFORMATION: A, Q, M, C ou E
<220> FEATURE:
<221> NAME/KEY: MISC_FEATURE
<222> LOCATION: (7)..(7)
<223> OTHER INFORMATION: I, E ou D
<220> FEATURE:
<221> NAME/KEY: MISC_FEATURE
<222> LOCATION: (8)..(8)
<223> OTHER INFORMATION: F, Y, S ou L

<400> SEQUENCE: 7

Xaa Xaa Xaa Xaa Xaa Xaa Xaa Xaa Arg
1               5

<210> SEQ ID NO 8
<211> LENGTH: 12
<212> TYPE: PRT
<213> ORGANISM: artificial sequence
<220> FEATURE:
<223> OTHER INFORMATION: epitope

<400> SEQUENCE: 8

Asn Tyr Val Thr Pro Pro Trp Ala Ile Phe Arg His
```

```
1               5              10
```

<210> SEQ ID NO 9
<211> LENGTH: 12
<212> TYPE: PRT
<213> ORGANISM: artificial sequence
<220> FEATURE:
<223> OTHER INFORMATION: epitope

<400> SEQUENCE: 9

```
Trp Thr Gly Val Leu Ser Pro Thr Gln Glu Tyr Arg
1               5                   10
```

<210> SEQ ID NO 10
<211> LENGTH: 12
<212> TYPE: PRT
<213> ORGANISM: artificial sequence
<220> FEATURE:
<223> OTHER INFORMATION: epitope

<400> SEQUENCE: 10

```
Ser His Leu Thr Pro Pro Trp Met Asp Tyr Arg Val
1               5                   10
```

<210> SEQ ID NO 11
<211> LENGTH: 12
<212> TYPE: PRT
<213> ORGANISM: artificial sequence
<220> FEATURE:
<223> OTHER INFORMATION: epitope

<400> SEQUENCE: 11

```
Val Met Ala Val Thr Cys Ser Thr Cys Asp Ser Arg
1               5                   10
```

<210> SEQ ID NO 12
<211> LENGTH: 12
<212> TYPE: PRT
<213> ORGANISM: artificial sequence
<220> FEATURE:
<223> OTHER INFORMATION: epitope

<400> SEQUENCE: 12

```
Leu Thr Pro Pro Thr Glu Asp Leu Arg Pro Pro Asp
1               5                   10
```

<210> SEQ ID NO 13
<211> LENGTH: 8
<212> TYPE: PRT
<213> ORGANISM: artificial sequence
<220> FEATURE:
<223> OTHER INFORMATION: epitope
<220> FEATURE:
<221> NAME/KEY: MISC_FEATURE
<222> LOCATION: (1)..(1)
<223> OTHER INFORMATION: S ou T
<220> FEATURE:
<221> NAME/KEY: MISC_FEATURE
<222> LOCATION: (2)..(2)
<223> OTHER INFORMATION: C ou absent
<220> FEATURE:
<221> NAME/KEY: MISC_FEATURE
<222> LOCATION: (3)..(3)
<223> OTHER INFORMATION: T, L ou E
<220> FEATURE:
<221> NAME/KEY: MISC_FEATURE
<222> LOCATION: (4)..(4)
<223> OTHER INFORMATION: H ou R
<220> FEATURE:
<221> NAME/KEY: MISC_FEATURE

```
<222> LOCATION: (5)..(5)
<223> OTHER INFORMATION: I, F ou E
<220> FEATURE:
<221> NAME/KEY: MISC_FEATURE
<222> LOCATION: (6)..(6)
<223> OTHER INFORMATION: V ou G
<220> FEATURE:
<221> NAME/KEY: MISC_FEATURE
<222> LOCATION: (8)..(8)
<223> OTHER INFORMATION: C ou N

<400> SEQUENCE: 13

Xaa Xaa Xaa Xaa Xaa Xaa His Xaa
1               5

<210> SEQ ID NO 14
<211> LENGTH: 12
<212> TYPE: PRT
<213> ORGANISM: artificial sequence
<220> FEATURE:
<223> OTHER INFORMATION: epitope

<400> SEQUENCE: 14

Tyr Gly Asn His Ser Cys Thr His Ile Gly His Cys
1               5                   10

<210> SEQ ID NO 15
<211> LENGTH: 12
<212> TYPE: PRT
<213> ORGANISM: artificial sequence
<220> FEATURE:
<223> OTHER INFORMATION: epitope

<400> SEQUENCE: 15

Gly Pro Ser Tyr Thr Cys Leu His Phe Gly His Cys
1               5                   10

<210> SEQ ID NO 16
<211> LENGTH: 12
<212> TYPE: PRT
<213> ORGANISM: artificial sequence
<220> FEATURE:
<223> OTHER INFORMATION: epitope

<400> SEQUENCE: 16

Thr Glu Arg Glu Val His Asn Trp Phe Pro Phe His
1               5                   10

<210> SEQ ID NO 17
<211> LENGTH: 9
<212> TYPE: PRT
<213> ORGANISM: artificial sequence
<220> FEATURE:
<223> OTHER INFORMATION: epitope
<220> FEATURE:
<221> NAME/KEY: MISC_FEATURE
<222> LOCATION: (1)..(1)
<223> OTHER INFORMATION: P ou W
<220> FEATURE:
<221> NAME/KEY: MISC_FEATURE
<222> LOCATION: (4)..(4)
<223> OTHER INFORMATION: W ou E
<220> FEATURE:
<221> NAME/KEY: MISC_FEATURE
<222> LOCATION: (5)..(5)
<223> OTHER INFORMATION: S, A, Q ou W
<220> FEATURE:
<221> NAME/KEY: MISC_FEATURE
<222> LOCATION: (6)..(6)
<223> OTHER INFORMATION: M, L, R ou P
<220> FEATURE:
```

```
<221> NAME/KEY: MISC_FEATURE
<222> LOCATION: (7)..(7)
<223> OTHER INFORMATION: H, F, W ou G
<220> FEATURE:
<221> NAME/KEY: MISC_FEATURE
<222> LOCATION: (8)..(8)
<223> OTHER INFORMATION: V ou A
<220> FEATURE:
<221> NAME/KEY: MISC_FEATURE
<222> LOCATION: (9)..(9)
<223> OTHER INFORMATION: V ou I

<400> SEQUENCE: 17

Xaa His Pro Xaa Xaa Xaa Xaa Xaa
1               5

<210> SEQ ID NO 18
<211> LENGTH: 12
<212> TYPE: PRT
<213> ORGANISM: artificial sequence
<220> FEATURE:
<223> OTHER INFORMATION: epitope

<400> SEQUENCE: 18

Tyr Pro His Pro Trp Ser Met His Val Ile Arg Ala
1               5                   10

<210> SEQ ID NO 19
<211> LENGTH: 12
<212> TYPE: PRT
<213> ORGANISM: artificial sequence
<220> FEATURE:
<223> OTHER INFORMATION: epitope

<400> SEQUENCE: 19

Thr Thr Thr Pro His Pro Trp Ala Leu Phe Ala Val
1               5                   10

<210> SEQ ID NO 20
<211> LENGTH: 12
<212> TYPE: PRT
<213> ORGANISM: artificial sequence
<220> FEATURE:
<223> OTHER INFORMATION: epitope

<400> SEQUENCE: 20

Thr Pro His Pro Trp Gln Arg Trp Val Val Tyr Ser
1               5                   10

<210> SEQ ID NO 21
<211> LENGTH: 12
<212> TYPE: PRT
<213> ORGANISM: artificial sequence
<220> FEATURE:
<223> OTHER INFORMATION: epitope

<400> SEQUENCE: 21

Glu Asp Val Leu Arg Trp His Pro Glu Trp Pro Gly
1               5                   10

<210> SEQ ID NO 22
<211> LENGTH: 6
<212> TYPE: PRT
<213> ORGANISM: artificial sequence
<220> FEATURE:
<223> OTHER INFORMATION: epitope
<220> FEATURE:
<221> NAME/KEY: MISC_FEATURE
<222> LOCATION: (1)..(1)
```

```
<223> OTHER INFORMATION: Y ou N
<220> FEATURE:
<221> NAME/KEY: MISC_FEATURE
<222> LOCATION: (3)..(3)
<223> OTHER INFORMATION: E, D ou Q
<220> FEATURE:
<221> NAME/KEY: MISC_FEATURE
<222> LOCATION: (4)..(4)
<223> OTHER INFORMATION: T, N, R, M ou K
<220> FEATURE:
<221> NAME/KEY: MISC_FEATURE
<222> LOCATION: (5)..(5)
<223> OTHER INFORMATION: W, H ou F
<220> FEATURE:
<221> NAME/KEY: MISC_FEATURE
<222> LOCATION: (6)..(6)
<223> OTHER INFORMATION: P ou G

<400> SEQUENCE: 22

Xaa His Xaa Xaa Xaa Xaa
1               5

<210> SEQ ID NO 23
<211> LENGTH: 12
<212> TYPE: PRT
<213> ORGANISM: artificial sequence
<220> FEATURE:
<223> OTHER INFORMATION: epitope

<400> SEQUENCE: 23

Tyr His Glu Thr Trp Pro Pro Lys Ser Ala Gln Leu
1               5                   10

<210> SEQ ID NO 24
<211> LENGTH: 12
<212> TYPE: PRT
<213> ORGANISM: artificial sequence
<220> FEATURE:
<223> OTHER INFORMATION: epitope

<400> SEQUENCE: 24

Tyr His Asp Asn Trp Pro Gln Pro Ser Arg Ser Trp
1               5                   10

<210> SEQ ID NO 25
<211> LENGTH: 12
<212> TYPE: PRT
<213> ORGANISM: artificial sequence
<220> FEATURE:
<223> OTHER INFORMATION: epitope

<400> SEQUENCE: 25

Gln His Asn His Gln Arg His Gly Ala Met Gly Ala
1               5                   10

<210> SEQ ID NO 26
<211> LENGTH: 12
<212> TYPE: PRT
<213> ORGANISM: artificial sequence
<220> FEATURE:
<223> OTHER INFORMATION: epitope

<400> SEQUENCE: 26

Tyr His Asp Met Trp Pro Met Ser Gly Arg Met Ala
1               5                   10

<210> SEQ ID NO 27
<211> LENGTH: 12
<212> TYPE: PRT
```

```
<213> ORGANISM: artificial sequence
<220> FEATURE:
<223> OTHER INFORMATION: epitope

<400> SEQUENCE: 27

Tyr His Asp Asn Trp Pro Pro Leu Asn Gly Ala Arg
1               5                   10

<210> SEQ ID NO 28
<211> LENGTH: 12
<212> TYPE: PRT
<213> ORGANISM: artificial sequence
<220> FEATURE:
<223> OTHER INFORMATION: epitope

<400> SEQUENCE: 28

Tyr His Asp Met Trp Pro Ala Ile Gln Leu Ser Pro
1               5                   10

<210> SEQ ID NO 29
<211> LENGTH: 12
<212> TYPE: PRT
<213> ORGANISM: artificial sequence
<220> FEATURE:
<223> OTHER INFORMATION: epitope

<400> SEQUENCE: 29

Tyr His Glu Lys Phe Pro Gly Pro Val Val Leu Pro
1               5                   10

<210> SEQ ID NO 30
<211> LENGTH: 13
<212> TYPE: PRT
<213> ORGANISM: human

<400> SEQUENCE: 30

Glu Pro Leu Gln Ala Glu Asp Pro Leu Gln Ala Lys
1               5                   10

<210> SEQ ID NO 31
<211> LENGTH: 10
<212> TYPE: PRT
<213> ORGANISM: human

<400> SEQUENCE: 31

Ala Tyr Glu Ala Asp Ala Gln Glu Gln Arg
1               5                   10
```